(12) United States Patent
Scheinberg et al.

(10) Patent No.: US 10,239,952 B2
(45) Date of Patent: Mar. 26, 2019

(54) ANTI-WT1/HLA BI-SPECIFIC ANTIBODY

(71) Applicants: MEMORIAL SLOAN-KETTERING CANCER CENTER, New York, NY (US); EUREKA THERAPEUTICS, INC., Emeryville, CA (US)

(72) Inventors: David Scheinberg, New York, NY (US); Jingyi Xiang, Walnut Creek, CA (US); Tao Dao, New York, NY (US); Su Yan, State College, PA (US); Cheng Liu, Oakland, CA (US)

(73) Assignees: Memorial Sloan Kettering Cancer Center, New York, NY (US); Eureka Therapeutics, Inc., Emeryville, CA (US)

( * ) Notice: Subject to any disclaimer, the term of this patent is extended or adjusted under 35 U.S.C. 154(b) by 0 days.

(21) Appl. No.: 15/034,782

(22) PCT Filed: Nov. 7, 2014

(86) PCT No.: PCT/US2014/064621
§ 371 (c)(1),
(2) Date: May 5, 2016

(87) PCT Pub. No.: WO2015/070061
PCT Pub. Date: May 14, 2015

(65) Prior Publication Data
US 2016/0280796 A1     Sep. 29, 2016

Related U.S. Application Data

(60) Provisional application No. 62/037,875, filed on Aug. 15, 2014, provisional application No. 61/901,310, filed on Nov. 7, 2013.

(51) Int. Cl.
*A61K 39/00* (2006.01)
*C07K 16/32* (2006.01)
*C07K 16/28* (2006.01)

(52) U.S. Cl.
CPC ........ *C07K 16/32* (2013.01); *A61K 2039/505* (2013.01); *C07K 16/2809* (2013.01); *C07K 2317/31* (2013.01); *C07K 2317/34* (2013.01); *C07K 2317/622* (2013.01); *C07K 2317/73* (2013.01)

(58) Field of Classification Search
None
See application file for complete search history.

(56) References Cited

U.S. PATENT DOCUMENTS

| | | | | |
|---|---|---|---|---|
| 8,076,459 | B2 * | 12/2011 | Hofmeister | C07K 16/2803 424/133.1 |
| 9,074,000 | B2 * | 7/2015 | Scheinberg | C07K 16/2833 |
| 9,540,448 | B2 * | 1/2017 | Scheinberg | C07K 16/2833 |
| 2009/0022738 | A1 * | 1/2009 | Hofmeister | |
| 2009/0252683 | A1 * | 10/2009 | Kischel | C07K 16/2809 424/9.2 |
| 2017/0088630 | A1 * | 3/2017 | Scheinberg | C07K 16/2833 |

FOREIGN PATENT DOCUMENTS

| | | |
|---|---|---|
| JP | 2007-537714 A | 12/2007 |
| JP | 2014-512812 A | 5/2014 |
| WO | WO-1994/028027 A1 | 12/1994 |
| WO | WO-2005/040220 A1 | 5/2005 |
| WO | WO-2012/135854 A2 | 10/2012 |
| WO | WO2012135854 | * 10/2012 |

OTHER PUBLICATIONS

Almagro & Fransson, Frontiers in Bioscience 2008; 13:1619-33.*
De Genst et al., Developmental and Comparative Immunology, 2006, 30:187-98.*
Ward et al., Nature, 1989, 341:544-546.*
Barthelemy et al., Journal of Biological Chemistry, 2008, 283:3639-3654.*
Choi et al., 2011, Molecular BioSystems, 2011, 7:3327-334.*
Griffiths et al., The EMBO Journal, 1993, 12:725-734.*
Klimka et al., British Journal of Cancer, 2000, 83:252-260.*
Beiboer et al., Journal of Molecular Biology, 2000, 296:833-849.*
Aigner et al., T lymphocytes can be effectively recruited for ex vivo and in vivo lysis of AML blasts by a novel CD33/CD3-bispecific BITE antibody construct. *Leukemia*, 27(5): 1107-15 (2013).
Bird et al., Single-chain antigen-binding proteins. *Science*, 242: 423-6 (1988).
Brischwein et al., Strictly target cell-dependent activation of T cells by bispecific single-chain antibody constructs of the BiTE class. *J. immunother.* 30(8): 798-807 (2007).
Cheever et al., The prioritization of cancer antigens: a national cancer institute pilot project for the acceleration of translational research. *Clin. Cancer Res.* 15(17): 5323-37 (2009).

(Continued)

*Primary Examiner* — Julie Wu
(74) *Attorney, Agent, or Firm* — Foley & Lardner LLP

(57) ABSTRACT

Disclosed herein is a bi-specific form of a T cell receptor mimic (TCRm) mAb with reactivity to human immune effector cell antigen and a WT1 peptide/HLA-A epitope. This antibody selectively bound to leukemias and solid tumor cells expressing WT1 and HLA-A as well as activated resting human T cells to release interferon-(IFN-γ) and to kill the target cancer cells in vitro. Importantly, the antibody mediated autologous T cell proliferation and directed potent cytotoxicity against fresh ovarian cancer cells. Therapeutic activity in vivo of the antibody was demonstrated in NOD SCID SCID Yc*(NSG) mice with three different human cancers expressing WT1/HLA-A2 including disseminated Ph+ acute lymphocytic leukemia (ALL), disseminated acute myeloid leukemia, and peritoneal mesothelioma. In both of the leukemia xenograft models, mice that received the antibody and T cells also showed longer survival and delayed limb paralysis. Also provided are methods for stimulating a primary T cell response comprising stimulating cytotoxic T cells against a first tumor antigen and a secondary T cell response comprising stimulating effector T cells and/or memory T cells against a first tumor antigen and/or against a second tumor antigen using the bi-specific antibodies described herein.

8 Claims, 37 Drawing Sheets

Specification includes a Sequence Listing.

(56) References Cited

OTHER PUBLICATIONS

Corbiere et al., Antigen spreading contributes to MAGE vaccination-induced regression of melanoma metastases. *Cancer Res.* 71(4): 1253-62 (2011).

Dao et al., Targeting the intracellular WT1 oncogene product with a therapeutic human antibody. *Sci. Transl. Med.* 5(176):176ra133 (2013).

Doubrovina et al., Adoptive immunotherapy with unselected or EBV-specific T cells for biopsy-proven EBV+ lymphomas after allogeneic hematopoietic cell transplantation. *Blood*, 119(11): 2644-55 (2012).

Doubrovina et al., Mapping of novel peptides of WT-1 and presenting HLA alleles that induce epitope-specific HLA-restricted T cells with cytotoxic activity against WT-1(+) leukemias. *Blood.* 120(8): 1633-46 (2012).

Evans et al., Design of nonpeptidal ligands for a peptide receptor: cholecystokinin antagonists. *J. Med. Chem.* 30:1229-39 (1987).

Fan et al., Improving the efficiency of CHO cell line generation using glutamine synthetase gene knockout cells. *Biotechnol. Bioeng.* 109(4): 1007-15 (2012).

Fauchere, *Adv. Drug Res.* 15:29 (1986).

Frankel et al., Targeting T cells to tumor cells using bispecific antibodies. *Curr. Opin. Chem. Biol.* 17(3): 385-92 (2013).

Gaiger et al., WT1-specific serum antibodies in patients with leukemia. *Clin. Cancer Res.* 7(Suppl. 3): 761s-5s (2001).

Gillmore et al., Detection of Wilms' tumor antigen--specific CTL in tumor-draining lymph nodes of patients with early breast cancer. *Clin. Cancer Res.* 12(1): 34-42 (2006).

Gluzman et al., SV40-transformed simian cells support the replication of early SV40 mutants. *Cell*, 23: 175-82 (1981).

Hilchey et al., Rituximab immunotherapy results in the induction of a lymphoma idiotype-specific T-cell response in patients with follicular lymphoma: support for a "vaccinal effect" of rituximab. *Blood*, 113(16): 3809-12 (2009).

Huston et al., Protein engineering of antibody binding sites: recovery of specific activity in an anti-digoxin single-chain Fv analogue produced in *Escherichia coli. Proc. Natl. Acad. Sci. USA*, 85: 5879-83 (1988).

Keilholz et al., A clinical and immunological phase 2 trail of Wilms tumor gene product 1 (WT1) peptide vaccination in patients with AML and MDS. *Blood*, 113(26): 6541-8 (2009).

Konig, Interactions between MHC molecules and co-receptors of the TCR. *Curr. Opin. Immunol.* 14(1):75-83 (2002).

Krug et al., WT1 peptide vaccinations induce CD4 and CD8 T cell immune responses in patients with mesothelioma and non-small cell lung cancer. *Cancer Immunol. Immunother.* 59:1467-79 (2010).

Maslak et al., Vaccination with synthetic analog peptides derived from WT1 oncoprotein induces T-cell responses in patients with complete remission from acute myeloid leukemia. *Blood.* 2010;116(2):171-9.

May et al., Peptide epitopes from the Wilms' tumor 1 oncoprotein stimulate CD4+ and CD8+ T cells that recognize and kill human maliganant tumor cells. *Clin. Cancer Res.*13(15 Pt 1): 4547-55 (2007).

McMahan et al., A novel IL-1 receptor, cloned from B cells by mammalian expression, is expressed in many cell types. *EMBO J.* 10: 2821-32 (1991).

Menssen et al., Presence of Wilms' tumor gene (wt1) transcripts and the WT1 nuclear protein in the majority of human acute leukemias. *Leukemia*, 9(6): 1060-7 (1995).

Morris et al., Generation of tumor-specific T-cell therapy. *Blood Rev.* 20: 61-9 (2006).

Nagorsen et al., Blinatumomab: a historical perspective. *Pharmacol. Ther.* 136(3): 334-42 (2012).

Nagorsen et al., Immunomodulatory therapy of cancer with T cell-engaging BiTE antibody blinatumomab. *Exp. CellRes.*317(9): 1255-60 (2011).

Oji et al., Expression of the Wilms' tumor gene WT1 in solid tumors and its involvement in tumor cell growth. *Jpn. J. Cancer Res.* 90(2):194-204 (1999).

Oka et al., Induction of WT1 (Wilms' tumor gene)-specific cytotoxic T lymphocytes by WT1 peptide vaccine and the resultant cancer regression. *Proc. Natl. Acad. Sci. USA*, 101(38): 13885-90 (2004).

Oka et al., WT1 peptide cancer vaccine for patients with hematopoietic malignancies and solid cancers. ScientificWorldJournal, 7: 649-65 (2007).

Pankov et al., A bi-specific T cell engaging monoclonal antibody (mAb) derived from a TCR-like Mab specific for WT1/HLA-A0201 (ESK-BiTE) shows a potent activity against human AML and Ph+ ALL in mouse models. *Blood*, 122(21): 2521 (2013).

Pritchard-Jones et al., The candidate Wilms' tumour gene is involved in genitourinary development. *Nature*, 346(6280): 194-7 (1990).

Rizo et al., Constrained peptides: models of bioactive peptides and protein substructures. *Ann. Rev. Biochem.* 61: 387-418 (1992).

Spiess et al., Bispecific antibodies with natural architecture produced by co-culture of bacteria expressing two distinct half-antibodies. *Nat. Biotechnol.* 31(8): 753-8 (2013).

Veber et al., The design of metabolically-stable peptide analogs. *Trends Neurosci.* 8: 392 (1985).

Ward et al., Binding activities of a repertoire of single immunoglobulin variable domains secreted from *Escherichia coli. Nature*, 341: 544-6 (1989).

\* cited by examiner

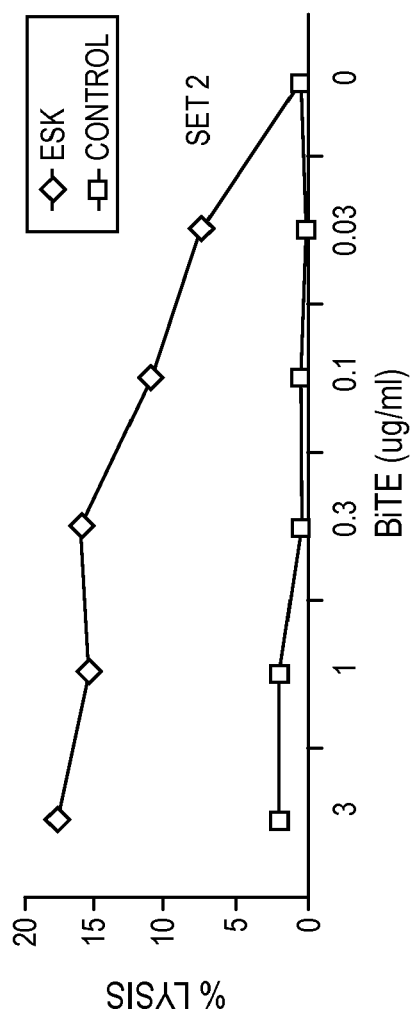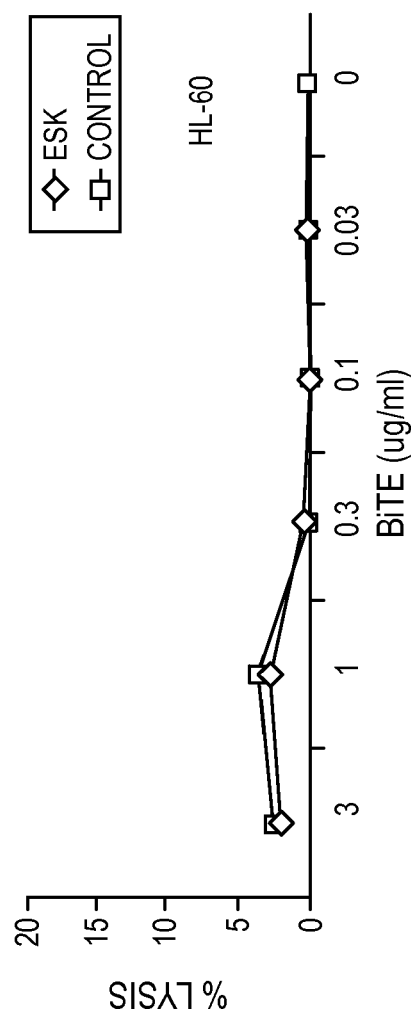
FIGURE 2A
FIGURE 2B

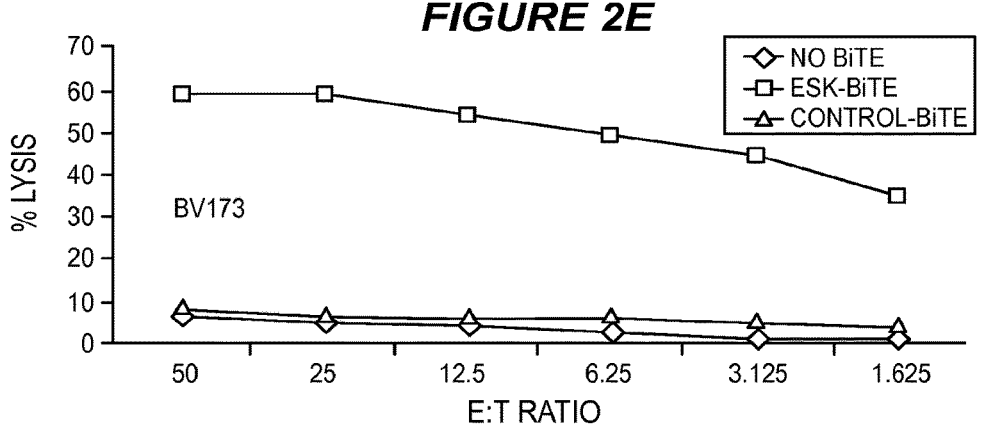
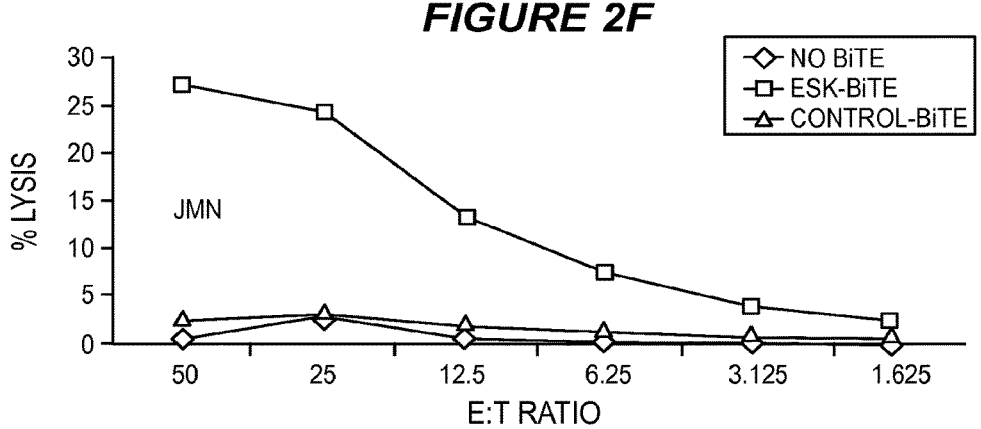
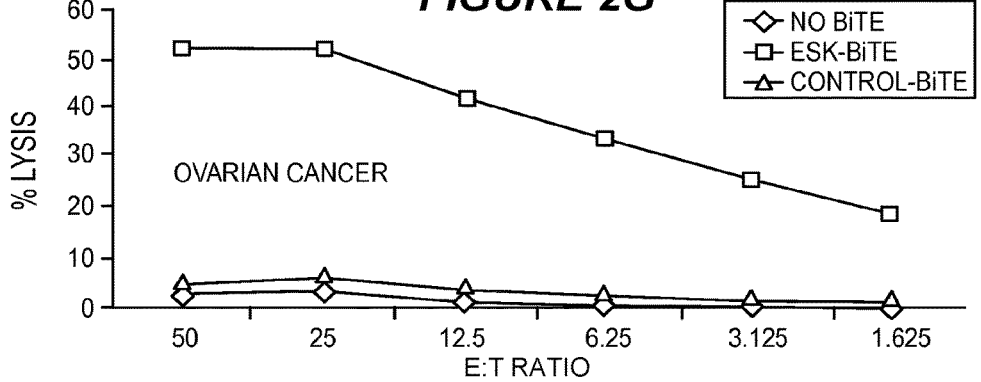

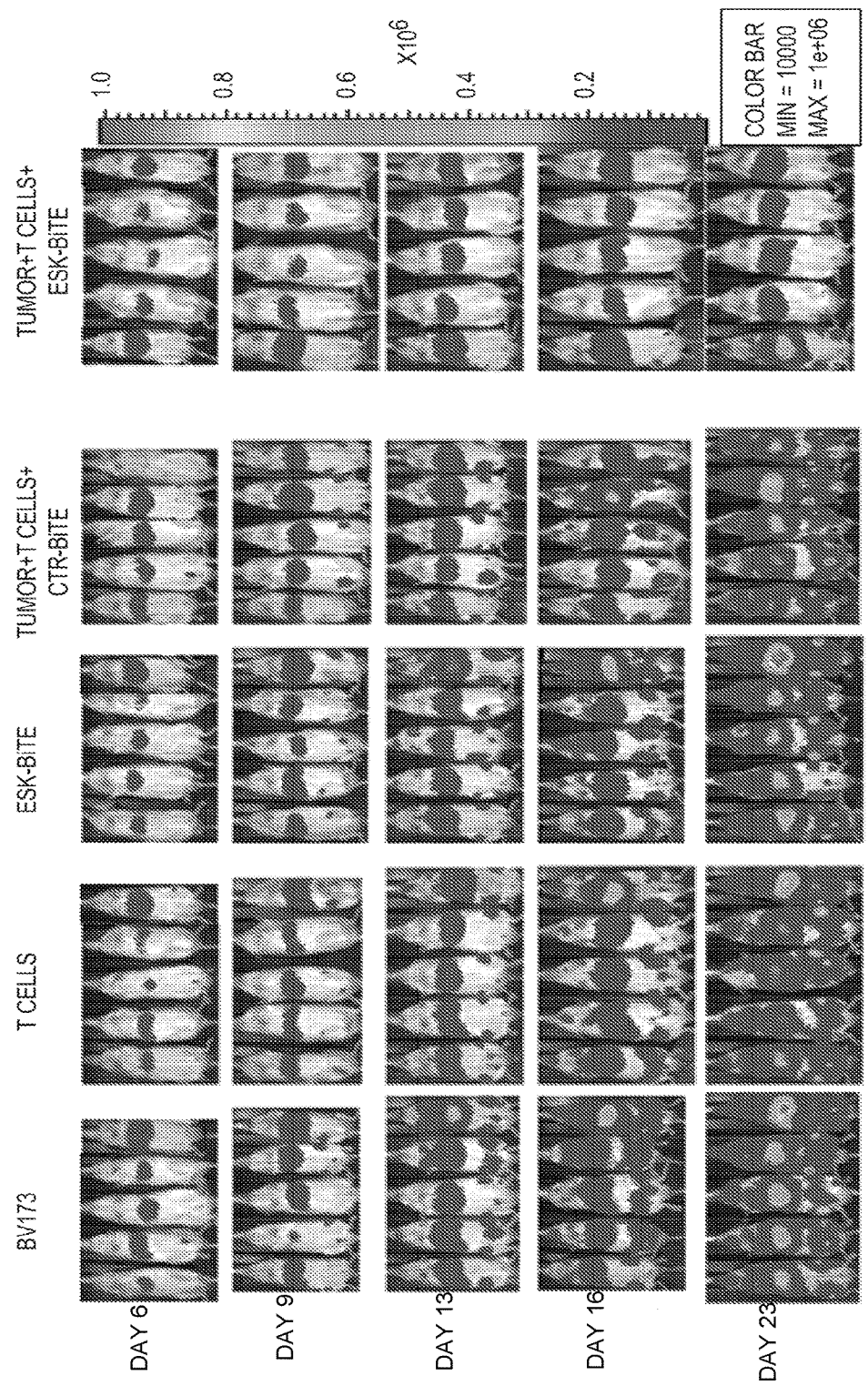

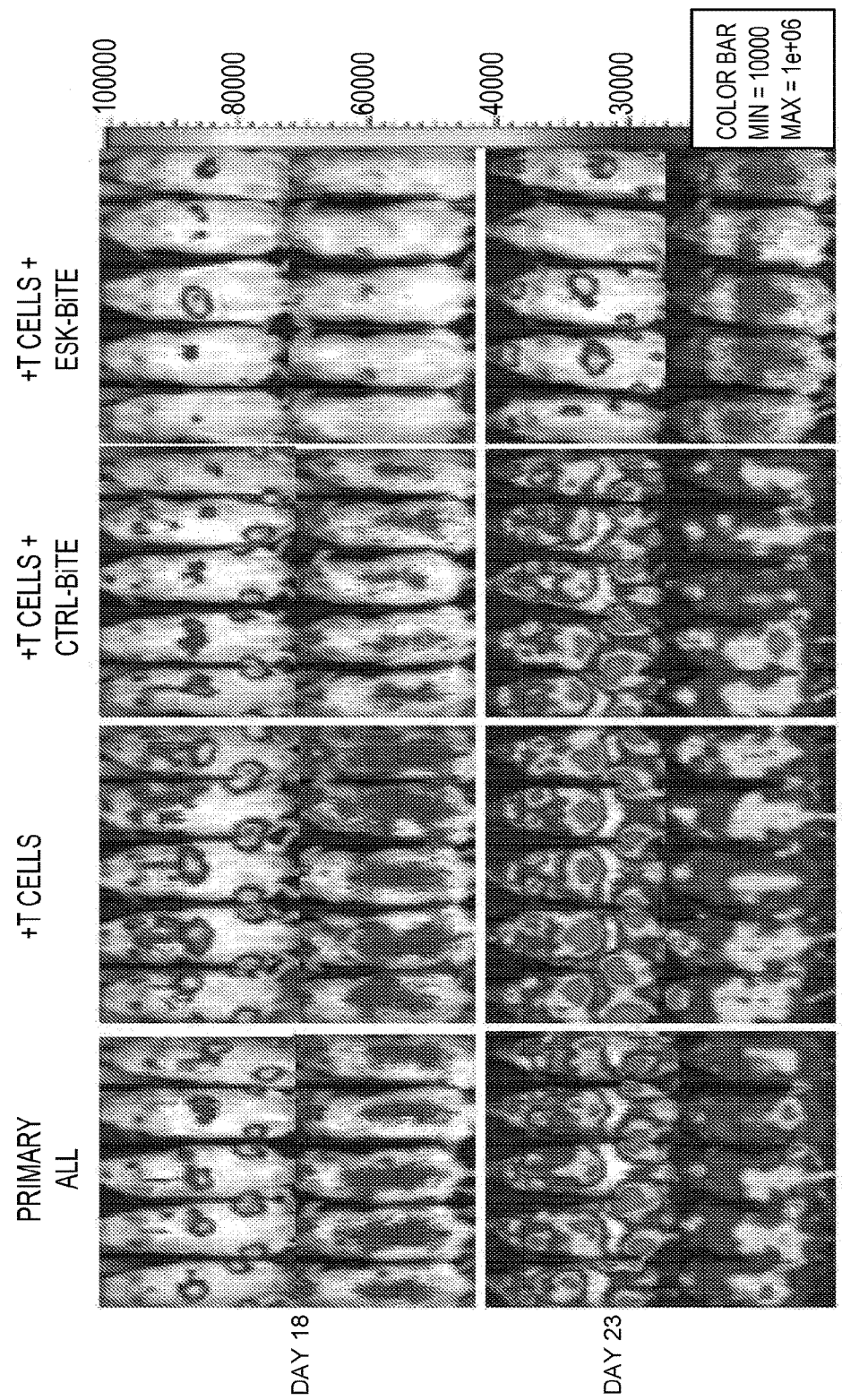

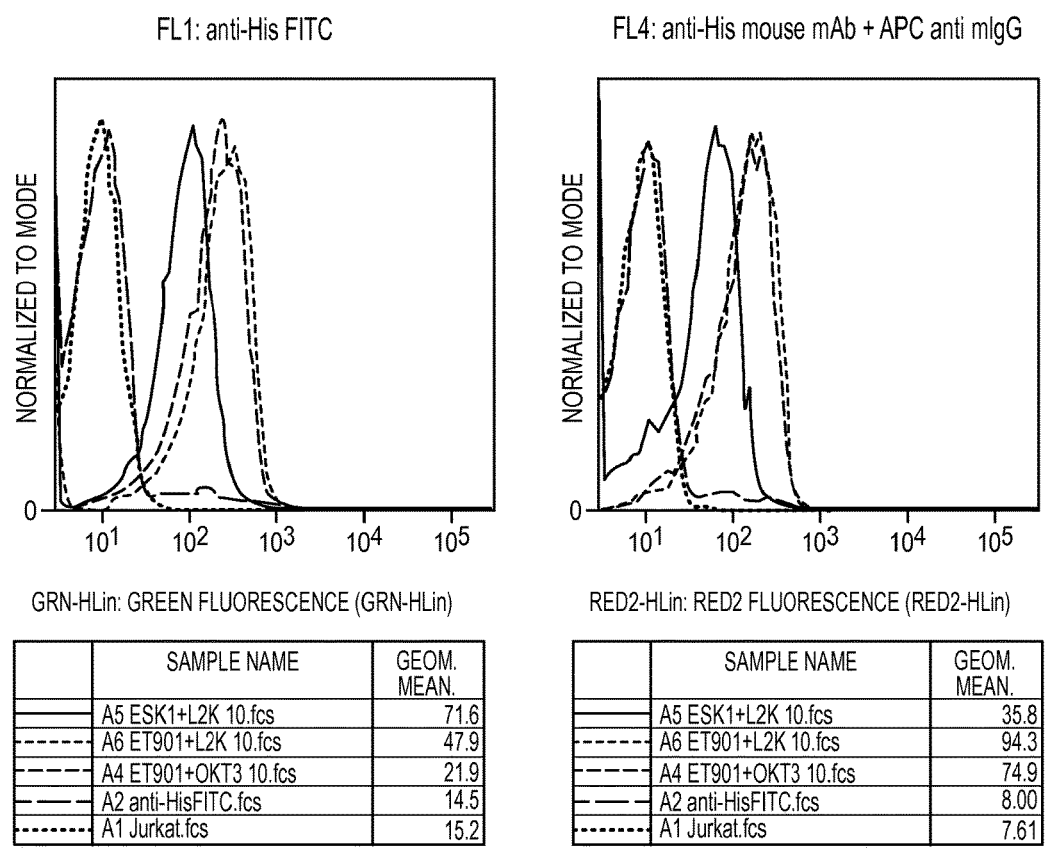

FIGURE 10

ESK1-T BITE AA SEQUENCE

MGWSCIILFLVATATGQAVVTQPPSASGTPGQRVTISCSGSSSNIGSNTVNWYQ
QVPGTAPKLLIYSNNQRPSGVPDRFSGSKSGTSASLAISGLQSEDEADYYCAAW
DDSLNGWVFGGGTKLTVLGSRGGGGSGGGGSGGGGSLEMAQMQLVQSGAE
VKEPGESLRISCKGSGYSFTNFWISWVRQMPGKGLEWMGRVDPGYSYSTYSPS
FQGHVTISADKSTSTAYLQWNSLKASDTAMYYCARVQYSGYYDWFDPWGQG
TLVTVSSGGGGSDVQLVQSGAEVKKPGASVKVSCKASGYTFTRYTMHWVRQA
PGQGLEWIGYINPSRGYTNYADSVKGRFTITTDKSTSTAYMELSSLRSEDTATYYC
ARYYDDHYCLDYWGQGTTVTVSSGEGTSTGSGGSGGSGGADDIVLTQSPATLS
LSPGERATLSCRASQSVSYMNWYQQKPGKAPKRWIYDTSKVASGVPARFSGSG
SGTDYSLTINSLEAEDAATYYCQQWSSNPLTFGGGTKVEIKHHHHHH**

Signal Peptide ESK1 Light chain variable region linker1 ESK1 heavy chain variable region linker2 L2K heavy chain variable region linker3 L2K light chain variable region Histag Lanes:

1. ESK1/OKT3 (2 µg, Reduced)
2. 901/OKT3 (2 µg, Reduced)
3. SeeBlue Plus Pre-Stained Standard
4. ESK1/OKT3 (2 µg, Non-Reduced)
5. 901/OKT3 (2 µg, Non-Reduced)

| | Tris-Glycine | Tricine | NuPAGE® MES | NuPAGE® MOPS |
|---|---|---|---|---|
| Myosin | 250 | 210 | 188 | 191 |
| Phosphorylase | 148 | 105 | 98 | 97 |
| BSA | 98 | 78 | 62 | 64 |
| Glutamic Dehydrogenase | 64 | 55 | 49 | 51 |
| Alcohol Dehydrogenase | 50 | 45 | 38 | 39 |
| Carbonic Anhydrase | 36 | 34 | 28 | 28 |
| Myoglobin Red | 22 | 17 | 17 | 19 |
| Lysozyme | 16 | 16 | 14 | 14 |
| Aprotinin | 6 | 7 | 6 | n/a |
| Insulin, B Chain | 4 | 4 | 3 | n/a |

NuPAGE® NOVEX® Bis-Tris 4-12% Gel

| | RETENTION (mL) | AREA (AU*mL) | HEIGHT (m/AU) |
|---|---|---|---|
| ESK1 | 3.5 | 1.12 | 1.89 |
| ESK1/OKT3 | 5.66 | 6.52 | 6.45 |

|  | RETENTION (mL) | AREA (AU*mL) | HEIGHT (m/AU) |
|---|---|---|---|
| ESK1 | 3.35 | 17.3 | 31.5 |
| OKT3 | 7.04 | 13.8 | 13.9 |

|  | RETENTION (mL) | AREA (AU*mL) | HEIGHT (mAU) |
|---|---|---|---|
| 901 | 4.59 | 0.98 | 1.33 |
| 901/OKT3 | 6.01 | 7.87 | 7.73 |

|  | RETENTION (mL) | AREA (AU*mL) | HEIGHT (mAU) |
|---|---|---|---|
| 901 | 4.59 | 16.9 | 26.5 |
| OKT3 | 7.07 | 15.8 | 15.5 |

OVARIAN CANCER

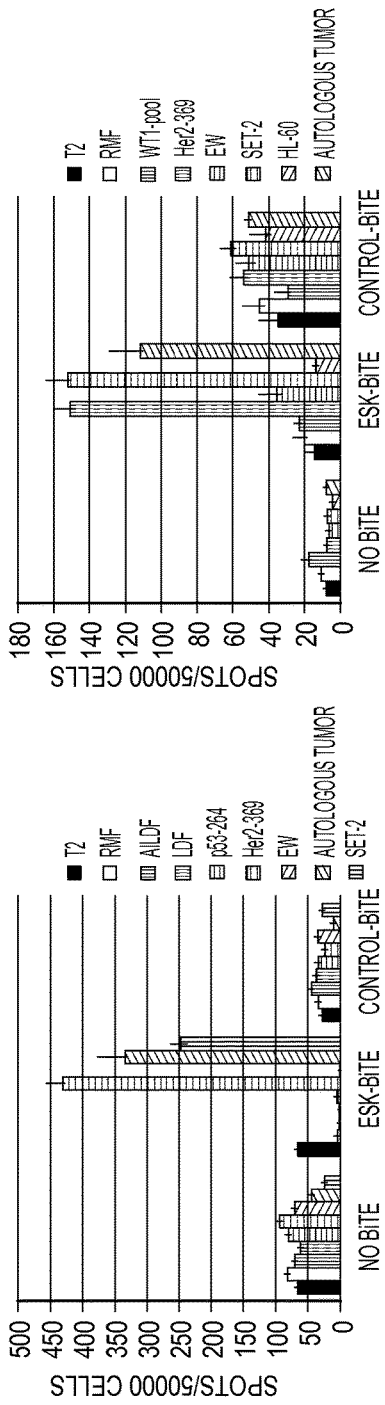
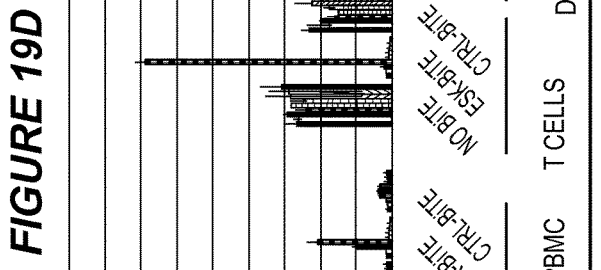
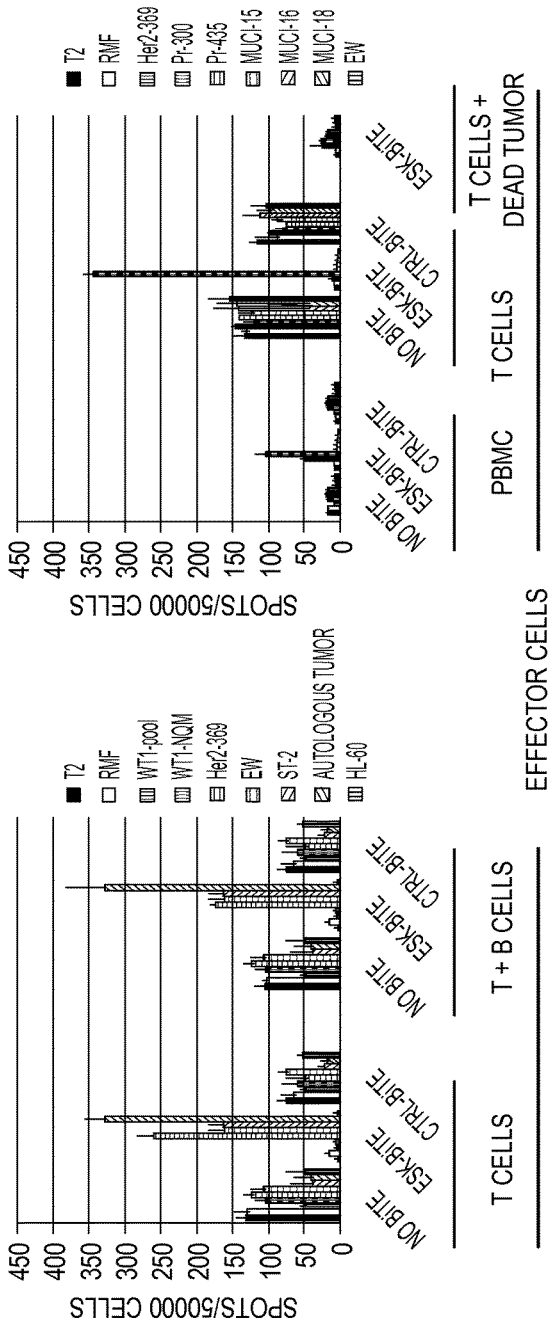

ANTI-WT1/HLA BI-SPECIFIC ANTIBODY

CROSS-REFERENCE TO RELATED APPLICATIONS

The benefit under 35 U.S.C. § 119(e) of U.S. Provisional Patent Application Ser. No. 61/901,310 filed Nov. 7, 2013, and U.S. Provisional Patent Application Ser. No. 62/037,875 filed Aug. 15, 2014 is hereby claimed, and the disclosures of both priority documents are incorporated herein by reference in their entirety.

This application contains subject matter that is related to the subject matter of U.S. Provisional Application No. 61/470,635, filed Apr. 1, 2011, and U.S. Provisional Application No. 61/491,392, filed May 31, 2011 and U.S. Non-Provisional application Ser. No. 14/008,447, filed Sep. 27, 2013, entitled "T-Cell Receptor Like Antibodies Specific for WT1 Peptides" and commonly assigned U.S. Provisional Application No. 61/798,563, entitled "Antibodies to Cytosolic Peptides" filed Mar. 15, 2013; the contents of each are hereby incorporated by reference in their entirety.

STATEMENT OF RIGHTS UNDER FEDERALLY-SPONSORED RESEARCH

This invention was made with government support under grant number CA023766 and CA055349 awarded by the National Institutes of Health. The government has certain rights in the invention.

SEQUENCE LISTING

This application contains, as a separate part of the disclosure, a sequence listing in computer-readable form (Filename: 48317_SeqListing.txt; Created: Nov. 7, 2014; Size: 93,841 bytes), which is hereby incorporated by reference in its entirety into the present application.

TECHNICAL FIELD

The present invention relates generally to antibodies against cytosolic proteins. More particularly, the invention relates to antibodies against Wilm's tumor oncogene protein (WT1), specifically bi-specific antibodies that recognize a WT1 peptide in conjunction with a major histocompatibility antigen, as well as an antigen displayed on the surface of an immune effector cell.

BACKGROUND OF THE INVENTION

The development of therapeutic T cell receptor-like monoclonal antibodies (TCRm mAbs), that recognize peptide fragments of key intracellular proteins in the context of MHC class I molecules, is emerging as a new approach to target intracellular tumor-specific antigens (Ags). Most tumor-specific Ags are intracellular proteins, inaccessible to classical mAb therapy. These proteins are degraded, processed and displayed by MHC class I molecules as peptide/MHC complexes, that are recognized by the TCR of cytotoxic T lymphocytes (CTLs). Consequently, numerous approaches aiming at triggering T cell responses toward the low density of tumor-specific peptide/MHC complexes have been attempted, with limited success. Wilms' tumor protein (WT1) is a well-validated human tumor-specific Ag for T cell immunotherapy. WT1 is over-expressed in a wide range of human hematopoietic malignancies, leukemia stem cells, and diverse solid tumors. In normal adult tissue, the protein has limited and low expression, which makes it an ideal cancer-specific target (Gessler et al. *Nature.* 1990; 346 (6280):194-197; Menssen et al. *Leukemia.* 1995; 9(6):1060-1067; Oji et al. *Jpn J Cancer Res.* 1999; 90(2):194-204). Both WT1 epitope-specific T cells and antibodies to WT1 whole protein have been detected in patients with hematopoietic malignancies and solid tumors, indicating that WT1 is a highly immunogenic antigen (Gaiger et al. *Clinical cancer research: an official journal of the American Association for Cancer Research.* 2001; 7(3 Suppl):761s-5s; Gillmore et al. *Clinical cancer research: an official journal of the American Association for Cancer Research.* 2006; 12(1):34-42). Furthermore, a correlation between graft-versus-leukemia and detectable WT1-specific CTLs was observed after allogeneic stem cell transplantation, further demonstrating the therapeutic activity of these T cells.

A WT1-derived peptide fragment, RMFPNAPYL (RMF; SEQ ID NO: 1), is the best studied and most validated epitope for CD8 T cell recognition in the context of HLA-A0201 molecule. The RMF epitope has been widely used in peptide vaccines or as the target of adoptively transferred CD8 T cells expanded ex vivo from patients with acute myeloid leukemia (AML), myeloid dysplastic syndrome (MDS) and various solid tumors. These studies demonstrated the immunogenicity of the peptide epitope, which was associated with clinical responses in some patients (Krug et al. *Cancer Immunol Immunother.* 2010; 59(1467-1479); Maslak et al. *Blood.* 2010; 116(2):171-9; Keilholz et al. *Blood.* 2009; 113(26):6541-8; Oka et al. *ScientificWorldJournal.* 2007; 7:649-65; Oka et al. *Proceedings of the National Academy of Sciences of the United States of America.* 2004; 101(38):13885-90; Letsch et al. and Keilholz, U., editor. *Associate for Immunotherapy of Cancer: Cancer Immunotherapy—2nd Annual Meeting;* 2004; Mainz, Germany).

Despite the significant progress in T cell immunotherapy, objective clinical responses are still rarely seen. Inefficiency of T cell-based therapies has been attributed to low TCR affinities, limited in vivo potent cytotoxic responses against high tumor burdens, the lack of effector cell persistence, tolerance to self-tumor Ags, and the immunosuppression by T-regulatory (T-reg) cells and cytokines (Morris et al. *Blood Reviews* 2006; 20: 61-69; Konnig R. *Curr Opin Immunol* 2002: 14 (1) 75-83). To develop a different approach to targeting this important epitope of WT1, a fully human TCRm mAb specific for the RMF/HLA-A0201 complex was generated. The mAb showed potent therapeutic activity against WT1-expressing leukemia and solid tumors, both in vitro and in vivo, via antibody-dependent cellular cytotoxicity (ADCC) (Dao et al. *Sci Transl Med.* 2013; 5(176): 176ra133).

ADCC depends on the presence of natural killer (NK) cells, macrophages, neutrophils and other immune-effector cells, that can be extremely heterogeneous in patients with leukemias or cancers, especially after therapy. An alternative and effective approach to mediate mAb cytolytic therapy is to use T cells as the effector cells. T cells are among the most potent cytotoxic cells and account for the largest number of circulating cytotoxic cells. Recent approaches that add mAb specificity to T cells, such as adoptively transferring T cells engineered with antibody-based chimeric antigen receptors (known as CARs) and bi-specific mAbs with dual specificities for tumor Ags and CD3 T cells, have emerged as efficient strategies to re-direct polyclonal human T cells to well-defined tumor-associated Ags. Bi-specific antibody constructs are designed to cross link the surface Ag on cancer cells to the TCR/CD3 complex on T cells. The molecules can redirect both CD4 and CD8 T cells to kill tumor cells in a serial fashion that is independent of the cells' intrinsic Ag-specific TCR recognition, co-stimulatory molecules, and HLA expression on tumor cells. It also avoids vaccination, cytokine administration or ex vivo expansion and infusion of Ag-specific, patient-derived T cells (Frankel and Baeuerle. *Current opinion in chemical biology.* 2013; 17(3):385-92; Brischwein et al. *Journal of immunotherapy.* 2007; 30(8):798-807; Nagorsen et al. *Pharmacology & therapeutics.* 2012; 136(3):334-42; Aigner et al. *Leukemia.* 2013; 27(5):1107-15; Spiess et al. *Nature biotechnology.* 2013; 31(8):753-8; Nagorsen and Baeuerle. *Experimental cell research.* 2011; 317(9):1255-60). The bi-specific t-cell engager (BITE®) antibody Blinatumomab (Amgen, Thousand Oaks, Calif.), specific for the pan B-cell Ag CD19 and the CD3e signaling chain of the TCR, is FDA approved for the treatment of non-Hodgkin's lymphoma and acute lymphocytic leukemia (ALL).

SUMMARY OF THE INVENTION

The bi-specific antibodies that have been described previously are all directed to well-known, high density cell surface Ags that are not tumor-specific. The present disclosure provides bi-specific antibodies derived from a TCRm mAb, designated ESK. The ESK-bi-specific antibody was able to selectively bind WT1/HLA-A0201 positive tumor cells and showed potent therapeutic activity in multiple human cancer models by redirecting human T cell cytotoxicity. Redirection of the T cell population to the cancer was demonstrated by dual target and effector cell tracking and imaging. The TCRm mAb bi-specific antibodies described herein are a potent therapeutic agent targeting a widely-expressed low density intracellular tumor-specific Ag, e.g., WT1. The bi-specific antibodies described herein are also capable of inducing a secondary T cell response specific for antigens other than WT1.

In one aspect, the invention relates to a recombinant antibody comprising a first antigen-binding portion that specifically binds to a WT1 peptide complexed with a major histocompatibility complex antigen such as HLA-A2 and can, therefore, bind to a WT1/HLA-A2$^+$ cell even when WT1 is present at low density. The antibody further comprises a second antigen-binding portion that specifically binds to a surface antigen on an immune effector cell, for example, CD3, and can, therefore, also bind the immune effector cell.

In one aspect, the invention relates to a recombinant antibody, wherein said recombinant antibody comprises: (i) a first antigen-binding portion comprising: (A) a heavy chain (HC) variable region comprising HC-CDR1, HC-CDR2 and HC-CDR3; and a light chain (LC) variable region comprising LC-CDR1, LC-CDR2 and LC-CDR3, comprising amino acid sequences as set forth in Tables 1-6; (B) a VH and a VL comprising first and second amino acid sequences as set forth in Tables 1-6; or (C) a scFv comprising an amino acid sequence as set forth in Tables 1-6; and (ii) a second antigen-binding portion comprising an amino acid sequence as set forth in Table 7. In one embodiment, the recombinant antibody comprises the amino acid sequence shown in FIG. 10 (SEQ ID NO: 110).

In another aspect, the invention relates to a nucleic acid that encodes a recombinant bi-specific antibody disclosed herein.

In a related aspect, the invention relates to pharmaceutical compositions comprising the recombinant bi-specific antibody and a pharmaceutically acceptable excipient. In another aspect, the invention relates to pharmaceutical compositions comprising a nucleic acid encoding the recombinant bi-specific antibody and a pharmaceutically acceptable excipient.

In yet another aspect, the invention relates to a method for killing a WT1$^+$ cell, said method comprising contacting the WT1$^+$ cell with an antibody having specificity for the amino acid sequence of SEQ ID NO: 1 and a cytotoxic T cell. In some embodiments, the cytotoxic T cell is an autologous cell.

In yet another related aspect, the invention relates to a method of treatment of a subject having a WT1-positive disease, the method comprising administering to the subject a therapeutically effective amount of a recombinant bi-specific antibody described herein. In one embodiment, the method further comprises administering to the subject CD3$^+$ cytotoxic T cells that are autologous. In one embodiment, the wT1-positive disease is a chronic leukemia or acute leukemia or WT1$^+$ cancer, for example, chronic myelocytic leukemia, multiple myeloma (MM), acute lymphoblastic leukemia (ALL), acute myeloid/myelogenous leukemia (AML), myelodysplastic syndrome (MDS), mesothelioma, ovarian cancer, gastrointestinal cancers, breast cancer, prostate cancer or glioblastoma.

In one aspect, the invention relates to a recombinant bi-specific antibody comprising a first antigen-binding portion comprising one of: (A) a single chain variable fragment (scFV) comprising an amino acid sequence selected from the group consisting of SEQ ID NOS: 18, 36, 54, 72, 90, 108, and 132; or (B) a heavy chain variable domain (VH) and a light chain variable domain (VL), wherein the VH and VL, respectively, comprise amino acid sequences selected from the group consisting of SEQ ID NOS: (i) 14 and 16; (ii) 32 and 34; (iii) 50 and 52; (iv) 68 and 70; (v) 86 and 88; (vi) 104 and 106; (vii) 128 and 130; or (C) (i) the following three VH complementarity determining regions (CDRs): (a) a VH CDR1 comprising the amino acid sequence selected from the group consisting of SEQ ID NOS: 2, 20, 38, 56, 74, 92 and 116; and (b) a VH CDR2 comprising an amino acid sequence selected from the group consisting of SEQ ID NOS: 3, 21, 39, 57, 75, 93 and 117; and (c) a VH CDR3 comprising an amino acid sequence selected from the group consisting of SEQ ID NOS: 4, 22, 40, 58, 76, 94 and 118; and (ii) the following three VL CDRs: (a) a VL CDR1 comprising an amino acid sequence selected from the group consisting of SEQ ID NOS: 8, 26, 44, 62, 80, 98, and 122; and (b) a VL CDR2 comprising an amino acid sequence selected from the group consisting of SEQ ID NOS: 9, 27, 45, 63, 81, 99, and 123; and (c) a VL CDR3 comprising an amino acid sequence selected from the group consisting of SEQ ID NOS: 10, 28, 46, 64, 82, 100, and 124. The recombinant bi-specific antibody further comprises a second antigen-binding portion comprising (A) a scFV comprising the amino acid sequence set forth in SEQ ID NO: 113; or (B) a heavy chain variable domain (VH) and a light chain variable domain (VL), wherein the VH and VL, respectively, comprise the amino acid sequences set forth in SEQ ID NOS: 112 and 111 or SEQ ID NOS: 134 and 136.

In another aspect, the invention provides a method of stimulating a primary T cell response and a secondary T cell response in a subject comprising administering a composition comprising a recombinant antibody, said recombinant antibody comprising a first antigen-binding portion and second antigen-binding portion, wherein said first antigen-binding portion specifically binds to a first tumor antigen and said second antigen-binding portion specifically binds to an immune effector cell surface antigen, wherein the primary T cell response comprises stimulating cytotoxic T cells against the first tumor antigen, and wherein the secondary T cell response comprises stimulating effector T cells and/or memory T cells against the first tumor antigen and/or against a second tumor antigen. In one aspect, the secondary T cell response does not require antigen presenting cells or co-stimulatory molecules. In another aspect, the secondary T cell response comprises stimulating effector T cells and/or memory T cells against the second tumor antigen. In one aspect, the second tumor antigen is a non-WT1-RMF tumor antigen.

In yet another aspect, the invention provides a method of producing effector T cells and/or memory T cells against a tumor antigen comprising activating a T cell with a recombinant bi-specific antibody disclosed herein. The effector T cells and/or memory T cells may be produced in vivo or ex vivo. In one aspect, the effector T cells and/or memory T cells are produced against a non-WT1-RMF tumor antigen, for example, HER2-neu.

The foregoing summary is not intended to define every aspect of the invention, and other features and advantages of the present disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

BRIEF DESCRIPTION OF THE DRAWINGS

FIG. 9 shows the results of a FACS binding analysis comparing binding of ESK1-L2K bi-specific antibody with ET901+L2K bi-specific antibody and ET901+OKT3 bi-specific antibody.

FIG. 10 shows the amino acid sequence (SEQ ID NO: 110) of an embodiment of a bi-specific antibody comprising a scFv that specifically binds to WT1/HLA-A2 and a scFv that specifically binds to Cd3.

DETAILED DESCRIPTION OF THE INVENTION

Figure 1A:
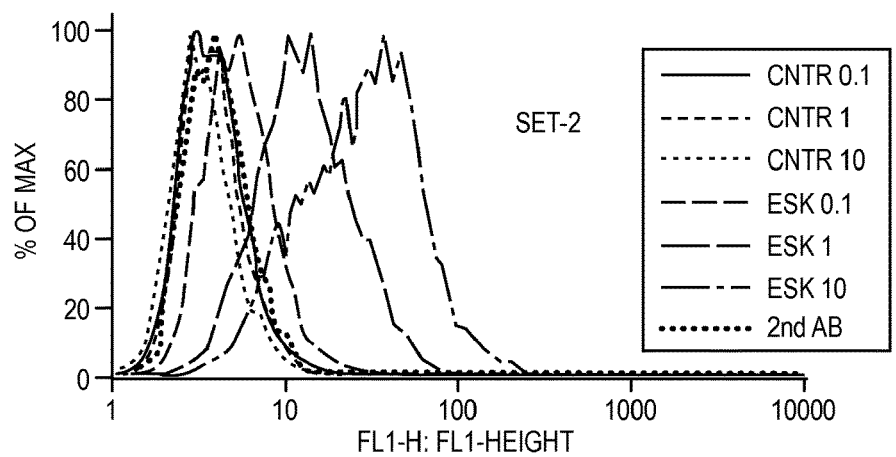
FIG. 1 shows selective binding of one embodiment of an ESK bi-specific antibody to tumor cells and human T cells measured by flow cytometry. SET-2 (1A), HL-60 (1B) or purified human CD3 T cells (1C) were stained with ESK-bi-specific antibody or control at concentrations of 10 µg/ml, 1 µg/ml or 0.1 µg/ml, followed by secondary mAb specific for His tag conjugated to FITC. ESK-bi-specific antibody showed selective binding to SET-2 cells at the concentrations of 10 µg/ml, 1 µg/ml and 0.1 µg/ml. The control secondary mAb alone and control bi-specific antibody at indicated concentrations did not bind to the cells. None of ESK nor control bi-specific antibodies bound to HL-60 at all the concentrations tested. For resting human T cells, ESK-bi-specific antibody showed a weaker binding than the control bi-specific antibody. Median fluorescence intensity (MFI) for ESK-bi-specific antibody: 91.4, 41 and 13.2 at concentration of 10 µg/ml, 1 µg/ml and 0.1 µg/ml, respectively. For control bi-specific antibody: 188, 153 and 26.2 at concentrations of 10 µg/ml, 1 µg/ml and 0.1 µg/ml, respectively. (1D) ESK-bi-specific antibody induce IFN-γ secretion in the presence of WT1+/HLA-A0201+ tumor cells. Human T cells and SET-2 cells at a 15:1 ratio were incubated with or without ESK-bi-specific antibody or control bi-specific antibody at a concentration of 3 µp/ml, 1 µp/ml, 0.3 µp/ml, 0.1 µp/ml, or 0.03 µp/ml for overnight. The supernatants were collected and IFN-γ release was measured by ELISA kit. The cultures of T cells alone or T cells with SET-2 cells, plus control bi-specific antibody did not show any detectable IFN-γ. Their values were therefore subtracted from the data shown. The data show the average of duplicate culture and represent one of two similar experiments.

All publications, patents and other references cited herein are incorporated by reference in their entirety into the present disclosure. Subject matter incorporated by reference is not considered to be an alternative to any claim limitations, unless otherwise explicitly indicated.

Unless otherwise defined herein, scientific and technical terms used in connection with the present invention shall have the meanings that are commonly understood by those of ordinary skill in the art. Further, unless otherwise required by context, singular terms shall include pluralities, and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. In practicing the present invention, many conventional techniques in immunology are used, which are within the skill of the ordinary artisan. These techniques are described in greater detail in, for example, "Current Protocols in Immunology" (John E. Coligan et al., eds., John Wiley & Sons, Inc. 1991 and periodic updates); Recombinant Antibodies for Immunotherapy, Melvyn Little, ed. Cambridge University Press 2009. The contents of these references and other references containing standard protocols, widely known to and relied upon by those of skill in the art, including manufacturers' instructions and dosage information, are hereby incorporated by reference as part of the present disclosure.

The following abbreviations are used throughout the application and are generally intended to be interpreted consistently with the meaning of the terms as known in the art:

Ab: Antibody
ADCC: Antibody-dependent cellular cytotoxicity
ALL: Acute lymphocytic leukemia
AML: Acute myeloid leukemia
BiTE: Bi-specific T-cell engager
CDC: Complement dependent cytotoxicity
CMC: Complement mediated cytotoxicity
CDR: Complementarity determining region (see also HVR below)
CL: Constant domain of the light chain
CH1: 1st constant domain of the heavy chain
CH1, 2, 3: 1st, 2nd and 3rd constant domains of the heavy chain
CH2, 3: 2nd and 3rd constant domains of the heavy chain
CHO: Chinese hamster ovary
CML: chronic myelogenous leukemia; also referred to as chronic myelocytic leukemia and chronic myeloid leukemia
CTL: Cytotoxic T cell
E:T Ratio: Effector:Target ratio
Fab: Antibody binding fragment
FACS: Fluorescence-activated cell sorting
FBS: Fetal bovine serum
FR: Framework region
GVHD: Graft-versus-host disease
HC: Heavy chain
HLA: Human leukocyte antigen
HVR-H: Hypervariable region-heavy chain (see also CDR)
HVR-L: Hypervariable region-light chain (see also CDR)
Ig: Immunoglobulin
KD: Dissociation constant
$k_{off}$: Dissociation rate
$k_{on}$: Association rate
MHC: Major histocompatibility complex
MM: Multiple myeloma
scFv: Single-chain variable fragment
$V_H$: Variable heavy chain includes heavy chain hypervariable region and heavy chain variable framework region
$V_L$: Variable light chain includes light chain hypervariable region and light chain variable framework region
WT1: Wilms tumor protein 1

In the description that follows, terms used herein are intended to be interpreted consistently with the meaning of those terms as they are known to those of skill in the art. The definitions provided herein below are meant to clarify, but not limit, the terms defined.

As used herein, "administering" and "administration" refer to the application of an active ingredient to the body of a subject.

"Antibody" and "antibodies" as those terms are known in the art refer to antigen binding proteins of the immune system. The term "antibody" as referred to herein includes whole, full length antibodies having an antigen-binding region, and any fragment thereof in which the "antigen-binding portion" or "antigen-binding region" is retained, or single chains, for example, single chain variable fragment (scFv), thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant (CH) region. The heavy chain constant region is comprised of three domains, CH1, CH2 and CH3. Each light chain is comprised of a light chain variable region (abbreviated herein as VL) and a light chain constant CL region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" or "antigen-binding region" of an antibody, as used herein, refers to that region or portion of the antibody that binds to the antigen and which confers antigen specificity to the antibody; fragments of antigen-binding proteins, for example, antibodies includes one or more fragments of an antibody that retain the ability to specifically bind to an antigen (e.g., an peptide/HLA complex). It has been shown that the antigen-binding function of an antibody can be performed by fragments of a full-length antibody. Examples of antigen-binding fragments encompassed within the term "antibody fragments" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., 1989 *Nature* 341:544-546), which consists of a VH domain; and an isolated complementarity determining region (CDR).

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules. These are known as single chain Fv (scFv); see e.g., Bird et al., 1988 *Science* 242:423-426; and Huston et al., 1988 *Proc. Natl. Acad. Sci.* 85:5879-5883. These antibody fragments are obtained using conventional techniques known to those of skill in the art, and the fragments are screened for utility in the same manner as are intact antibodies.

As used herein, the term "effective amount" means that amount of a compound or therapeutic agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The present disclosure provides compositions and methods of treatment relating to recombinant bi-specific antibodies. In one aspect, the invention provides a method of stimulating a primary T cell response and a secondary T cell response in a subject comprising administering a composition comprising a recombinant antibody, said recombinant antibody comprising a first antigen-binding portion and second antigen-binding portion, wherein said first antigen-binding portion specifically binds to a first tumor antigen and said second antigen-binding portion specifically binds to an immune effector cell surface antigen, wherein the primary T cell response comprises stimulating cytotoxic T cells against the first tumor antigen, and wherein the secondary T cell response comprises stimulating effector T cells and/or memory T cells against the first tumor antigen and/or against a second tumor antigen. In one aspect, the first tumor antigen is WT1/HLA and the second tumor antigen is a nont-WT1-RMF tumor antigen. In a related aspect, the invention provides a method of producing effector T cells and/or memory T cells against a tumor antigen, optionally a non-WT1-RMF tumor antigen such as HER2-neu. The methods of the present disclosure may further comprise administering an immune effector cell, for example, a cytotoxic cell such as a CD3+ cytotoxic T cell. Through the production of effector T cells, e.g., cytotoxic T cells, and/or memory T cells against a tumor antigen, the bi-specific antibodies of the present disclosure are thus able to achieve a vaccinal effect against tumor cells and can be used to generate cells for use in adoptive T cell therapy.

In another aspect, the present invention provides an improved anti-WT1 antibody useful for killing WT1 positive cells. The improved anti-WT1 antibody is a bi-specific antibody with a first antigen binding portion that specifically binds WT1 when it is presented in a histocompatibility-restricted fashion with HLA and a second antigen-binding portion that specifically binds to a cell surface antigen on the surface of an immune effector cell, for example, CD3 and, therefore, is able to engage immune effector cells, for example, CD3$^+$ T cells (i.e., cytotoxic T cells). In one aspect, a recombinant antibody or derivative or fragment thereof according to the present disclosure comprises: (i) a first antigen-binding portion comprising: (A) a heavy chain (HC) variable region comprising HC-CDR1, HC-CDR2 and HC-CDR3; and a light chain (LC) variable region comprising LC-CDR1, LC-CDR2 and LC-CDR3, comprising amino acid sequences set forth in Tables 1-6; (B) a VH and a VL comprising first and second amino acid sequences as set forth in Tables 1-6; or (C) an scFv comprising an amino acid sequence as set forth in Tables 1-6; and (ii) a second antigen-binding portion comprising an amino acid sequence set forth in Table 7. In one aspect, the first antigen binding portion and/or second antigen binding portion is an antibody fragment. Examples of antibody fragments include, but are not limited to, a Fab fragment; a monovalent fragment consisting of the VL, VH, CL and CH1 domains; a F(ab)2 fragment; a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment; an isolated CDR; and a scFv.

In one embodiment, the bi-specific antibody has a first binding portion with a variable heavy chain region comprising the amino acid sequence of SEQ ID NO: 50 and a variable light chain region comprising the amino acid sequence SEQ ID NO: 52 or a scFv with the amino acid sequence of SEQ ID NO: 54. Furthermore, the bi-specific antibody has a second binding portion comprising an L2K heavy chain variable region comprising the amino acid sequence of SEQ ID NO: 112 and an L2K light chain variable region comprising the amino acid sequence of SEQ ID NO: 111.

In other embodiments, the WT1/HLA binding portion of the bi-specific anti-WT1 antibody of the invention comprises one or more of the amino acid sequences (scFv, VH and VL regions or CDRs) listed in Tables 1-6 or 8.

In the sequences that follow in Tables 1-7, bolded text indicates a linker sequence between hypervariable heavy and light chain sequences.

In some embodiments, the antibody comprises a histidine tag for purification. In some embodiments, the antibody comprises a signal peptide and one or more linkers comprising glycine and serine residues.

TABLE 1

Antigen WT1
Peptide RMFPNAPYL (SEQ ID NO: 1)

| CDRs: | 1 | 2 | 3 |
|---|---|---|---|
| VH | GGTFSSYAIS (SEQ ID NO: 2) | GIIPIFGTANYAQKFQG (SEQ ID NO: 3) | RIPPYYGMDV (SEQ ID NO: 4) |
| DNA | ggaggcaccttcagc agctatgctatcagc (SEQ ID NO: 5) | gggatcatccctatc tttggtacagcaaac tacgcacagaagttc cagggc (SEQ ID NO: 6) | cggattcccccgtac tacggtatggacgtc (SEQ ID NO: 7) |
| VL | SGSSSNIGSNYVY (SEQ ID NO: 8) | RSNQRPS (SEQ ID NO: 9) | AAWDDSLNGVV (SEQ ID NO: 10) |
| DNA | tctggaagcagctcc aacatcggaagtaat tatgtatac (SEQ ID NO: 11) | aggagtaatcagcgg ccctca (SEQ ID NO: 12) | gcagcatgggatgac agcctgaatggtgtg gta (SEQ ID NO: 13) |
| Full VH | QVQLVQSGAEVKKPGSSVKVSCKASGGTFSSYAISWVRQ APGQGLEWMGGIIPIFGTANYAQKFQGRVTITADESTST AYMELSSLRSEDTAVYYCARRIPPYYGMDVWGQGTTVTV SS (SEQ ID NO: 14) | | |
| DNA | caggtgcagctggtgcagtctggggctgaggtgaagaag cctgggtcctcggtgaaggtctcctgcaaggcttctgga ggcaccttcagcagctatgctatcagctgggtgcgacag gcccctggacaagggcttgagtggatgggagggatcatc cctatctttggtacagcaaactacgcacagaagttccag ggcagagtcacgattaccgcggacgaatccacgagcaca gcctacatggagctgagcagcctgagatctgaggacacg gccgtgtattactgtgcgagacggattcccccgtactac ggtatggacgtctgggggccaagggaccacggtcaccgtc tcctca (SEQ ID NO: 15) | | |
| Full VL | QTVVTQPPSASGTPGQRVTISCSGSSSNIGSNYVYWYQQ LPGTAPKLLIYRSNQRPSGVPDRFSGSKSGTSASLAISG PRSVDEADYYCAAWDDSLNGVVFGGGTKLTVLG (SEQ ID NO: 16) | | |
| DNA | cagactgtggtgactcagccaccctcagcgtctgggacc cccgggcagagggtcaccatctcttgttctggaagcagc tccaacatcggaagtaattatgtatactggtaccaacag ctcccaggaacggcccccaaactcctcatctataggagt aatcagcggccctcaggggtccctgaccgattctctggc tccaagtctggcacctcagcctccctggccatcagtggg ccccggtccgtggatgaggctgattattactgtgcagca tgggatgacagcctgaatggtgtggtattcggcggaggg accaagctgaccgtcctaggt (SEQ ID NO: 17) | | |
| scFv | QTVVTQPPSASGTPGQRVTISCSGSSSNIGSNYVYWYQQ LPGTAPKLLIYRSNQRPSGVPDRFSGSKSGTSASLAISG PRSVDEADYYCAAWDDSLNGVVFGGGTKLTVLGSRGGGG SGGGGSGGGGSLEMAQVQLVQSGAEVKKPGSSVKVSCKAS GGTFSSYAISWVRQAPGQGLEWMGGIIPIFGTANYAQKF QGRVTITADESTSTAYMELSSLRSEDTAVYYCARRIPPY YGMDVWGQGTTVTVSS (SEQ ID NO: 18) | | |

TABLE 1-continued

Antigen WT1
Peptide RMFPNAPYL (SEQ ID NO: 1)

| CDRs: | 1 | 2 | 3 |
|---|---|---|---|

| DNA | cagactgtggtgactcagccaccctcagcgtctgggacc |
|---|---|
| | cccgggcagagggtcaccatctcttgttctggaagcagc |
| | tccaacatcggaagtaattatgtatactggtaccaacag |
| | ctcccaggaacggccccaaactcctcatctataggagt |
| | aatcagcggccctcaggggtccctgaccgattctctggc |
| | tccaagtctggcacctcagcctccctggccatcagtggg |
| | ccccggtccgtggatgaggctgattattactgtgcagca |
| | tgggatgacagcctgaatggtgtggtattcggcggaggg |
| | accaagctgaccgtcctaggttctagaggtggtggtggt |
| | agcggcggcggcggctctggtggtggatcctcgagatg |
| | gcccaggtgcagctggtgcagtctggggctgaggtgaag |
| | aagcctgggtcctcggtgaaggtctcctgcaaggcttct |
| | ggaggcaccttcagcagctatgctatcagctgggtgcga |
| | caggcccctggacaagggcttgagtggatgggagggatc |
| | atccctatctttggtacagcaaactacgcacagaagttc |
| | cagggcagagtcacgattaccgcggacgaatccacgagc |
| | acagcctacatggagctgagcagcctgagatctgaggac |
| | acggccgtgtattactgtgcgagacggattccccgtac |
| | tacggtatggacgtctggggccaagggaccacggtcacc |
| | gtctcctca (SEQ ID NO: 19) |

TABLE 2

Antigen WT1 (Ext002 #5)
Peptide RMFPNAPYL (SEQ ID NO: 1)

| CDRs: | 1 | 2 | 3 |
|---|---|---|---|
| VH | GDSVSSNSAAWN (SEQ ID NO: 20) | RTYYGSKWYNDYAVS VKS (SEQ ID NO: 21) | GRLGDAFDI (SEQ ID NO: 22) |
| DNA | ggggacagtgtctct agcaacagtgctgct tggaac (SEQ ID NO: 23) | aggacatactacggg tccaagtggtataat gattatgcagtatct gtgaaaagt (SEQ ID NO: 24) | ggtcgcttaggggat gctttgatatc (SEQ ID NO: 25) |
| VL | RASQSISSYN (SEQ ID NO: 26) | AASSLQS (SEQ ID NO: 27) | QQSYSTPLT (SEQ ID NO: 28) |
| DNA | cgggcaagtcagagc attagcagctattta aat (SEQ ID NO: 29) | gctgcatccagtttg caaagt (SEQ ID NO: 30) | caacagagttacagt acccctctcact (SEQ ID NO: 31) |
| Full VH | QVQLQQSGPGLVKPSQTLSLTCAISGDSVSSNSAAWNWI RQSPSRGLEWLGRTYYGSKWYNDYAVSVKSRITINPDTS KNQFSLQLNSVTPEDTAVYYCARGRLGDAFDIWGQGTMV TVSS (SEQ ID NO: 32) | | |
| DNA | caggtacagctgcagcagtcaggtccaggactggtgaag ccctcgcagaccctctcactcacctgtgccatctccggg gacagtgtctctagcaacagtgctgcttggaactggatc aggcagtccccatcgagaggccttgagtggctgggaagg acatactacgggtccaagtggtataatgattatgcagta tctgtgaaaagtcgaataaccatcaacccagacacatcc aagaaccagttctccctgcagctgaactctgtgactccc gaggacacggctgtgtattactgtgcaagaggtcgctta ggggatgcttttgatatctggggccaagggacaatggtc accgtctcttca (SEQ ID NO: 33) | | |
| Full VL | DIQMTQSPSSLSASVGDRVTITCRASQSISSYLNWYQQK PGKAPKLLIYAASSLQSGVPSRFSGSGSGTDFTLTISSL QPEDFATYYCQQSYSTPLTFGGGTKVDIKR (SEQ ID NO: 34) | | |
| DNA | gacatccagatgacccagtctccatcctccctgtctgca tctgtaggagacagagtcaccatcacttgccgggcaagt cagagcattagcagctatttaaattggtatcagcagaaa ccagggaaagcccctaagctcctgatctatgctgcatcc | | |

TABLE 2-continued

Antigen WT1 (Ext002 #5)
Peptide RMFPNAPYL (SEQ ID NO: 1)

| CDRs: | 1 | 2 | 3 |
|---|---|---|---| agtttgcaaagtggggtcccatcaaggttcagtggcagt
ggatctgggacagatttcactctcaccatcagcagtctg
caacctgaagattttgcaacttactactgtcaacagagt
tacagtacccctctcactttcggcggagggaccaaagtg
gatatcaaacgt (SEQ ID NO: 35)

scFv DIQMTQSPSSLSASVGDRVTITCRASQSISSYLNWYQQK
PGKAPKLLIYAASSLQSGVPSRFSGSGSGTDFTLTISSL
QPEDFATYYCQQSYSTPLTFGGGTKVDIKR**SRGGGGSGG
GGSGGGGSLEMA**QVQLQQSGPGLVKPSQTLSLTCAISGD
SVSSNSAAWNWIRQSPSRGLEWLGRTYYGSKWYNDYAVS
VKSRITINPDTSKNQFSLQLNSVTPEDTAVYYCARGRLG
DAFDIWGQGTMVTVSS (SEQ ID NO: 36)

DNA gacatccagatgacccagtctccatcctccctgtctgca
tctgtaggagacagagtcaccatcacttgccgggcaagt
cagagcattagcagctatttaaattggtatcagcagaaa
ccagggaaagcccctaagctcctgatctatgctgcatcc
agtttgcaaagtggggtcccatcaaggttcagtggcagt
ggatctgggacagatttcactctcaccatcagcagtctg
caacctgaagattttgcaacttactactgtcaacagagt
tacagtacccctctcactttcggcggagggaccaaagtg
gatatcaaacgt**tctagaggtggtggtggtagcggcggc
ggcggctctggtggtggtggatccctcgagatggcc**cag
gtacagctgcagcagtcaggtccaggactggtgaagccc
tcgcagaccctctcactcacctgtgccatctccggggac
agtgtctctagcaacagtgctgcttggaactggatcagg
cagtccccatcgagaggccttgagtggctgggaaggaca
tactacgggtccaagtggtataatgattatgcagtatct
gtgaaaagtcgaataaccatcaacccagacacatccaag
aaccagttctccctgcagctgaactctgtgactcccgag
gacacggctgtgtattactgtgcaagaggtcgcttaggg
gatgcttttgatatctggggccaagggacaatggtcacc
gtctcttca (SEQ ID NO: 37)

TABLE 3

Antigen WT1 (Ext002 #13)
Peptide RMFPNAPYL (SEQ ID NO: 1)

| CDRs: | 1 | 2 | 3 |
|---|---|---|---|
| VH | GYSFTNFWIS (SEQ ID NO: 38) | RVDPGYSYSTYSPSF QG (SEQ ID NO: 39) | VQYSGYYDWFDP (SEQ ID NO: 40) |
| DNA | ggatacagcttcacc aacttctggatcagc (SEQ ID NO: 41) | agggttgatcctggc tactcttatagcacc tacagcccgtccttc caaggc (SEQ ID NO: 42) | gtacaatatagtggc tactatgactggttc gacccc (SEQ ID NO: 43) |
| VL | SGSSSNIGSNTVN (SEQ ID NO: 44) | SNNQRPS (SEQ ID NO: 45) | AAWDDSLNGWV (SEQ ID NO: 46) |
| DNA | tctggaagcagctcc aacatcggaagtaat actgtaaac (SEQ ID NO: 47) | agtaataatcagcgg ccctca (SEQ ID NO: 48) | gcagcatgggatgac agcctgaatggttgg gtg (SEQ ID NO: 49) |
| Full VH | QMQLVQSGAEVKEPGESLRISCKGSGYSFTNFWISWVRQMPGKGLEW MGRVDPGYSYSTYSPSFQGHVTISADKSTSTAYLQWNSLKASDTAMY YCARVQYSGYYDWFDPWGQGTLVTVSS (SEQ ID NO: 50) | | |
| DNA | cagatgcagctggtgcagtccggagcagaggtgaaagagcccgggga gtctctgaggatctcctgtaagggttctggatacagcttcaccaact tctggatcagctgggtgcgccagatgccgggaaaggcctggagtgg atgggagaggttgatcctggctactcttatagcacctacagcccgtc cttccaaggccacgtcaccatctcagctgacaagtctaccagcactg | | |

TABLE 3-continued

Antigen WT1 (Ext002 #13)
Peptide RMFPNAPYL (SEQ ID NO: 1)

| CDRs: | 1 | 2 | 3 |
|---|---|---|---| cctacctgcagtggaacagcctgaaggcctcggacaccgccatgtat
tactgtgcgagagtacaatatagtggctactatgactggttcgaccc
ctggggccagggaaccctggtcaccgtctcctca
(SEQ ID NO: 51)

Full VL
QAVVTQPPSASGTPGQRVTISCSGSSSNIGSNTVNWYQQVPGTAPKL
LIYSNNQRPSGVPDRFSGSKSGTSASLAISGLQSEDEADYYCAAWDD
SLNGWVFGGGTKLTVLG (SEQ ID NO: 52)

DNA
caggctgtggtgactcagccaccctcagcgtctgggaccccgggca
gagggtcaccatctcttgttctggaagcagctccaacatcggaagta
atactgtaaactggtaccagcaggtcccaggaacggcccccaaactc
ctcatctatagtaataatcagcgggccctcagggggtccctgaccgatt
ctctggctccaagtctggcacctcagcctccctggccacagtgggc
tccagtctgaggatgaggctgattattactgtgcagcatgggatgac
agcctgaatggttgggtgttcggcggagggaccaagctgaccgtcct
aggt (SEQ ID NO: 53)

scFv
QAVVTQPPSASGTPGQRVTISCSGSSSNIGSNTVNWYQQVPGTAPKL
LIYSNNQRPSGVPDRFSGSKSGTSASLAISGLQSEDEADYYCAAWDD
SLNGWVFGGGTKLTVLGSRGGGGSGGGGSGGGGSLEMAQMQLVQSGA
EVKEPGESLRISCKGSGYSFTNFWISWVRQMPGKGLEWMGRVDPGYS
YSTYSPSFQGHVTISADKSTSTAYLQWNSLKASDTAMYYCARVQYSG
YYDWFDPWGQGTLVTVSS (SEQ ID NO: 54)

DNA
caggctgtggtgactcagccaccctcagcgtctgggaccccgggca
gagggtcaccatctcttgttctggaagcagctccaacatcggaagta
atactgtaaactggtaccagcaggtcccaggaacggcccccaaactc
ctcatctatagtaataatcagcgggccctcagggggtccctgaccgatt
ctctggctccaagtctggcacctcagcctccctggccacagtgggc
tccagtctgaggatgaggctgattattactgtgcagcatgggatgac
agcctgaatggttgggtgttcggcggagggaccaagctgaccgtcct
aggttctagaggtggtggtggtagcggcggcggcggtctggtggtg
gtggatccctcgagatggcccagatgcagctggtgcagtccggagca
gaggtgaaagagcccggggagtctctgaggatctcctgtaagggttc
tggatacagcttcaccaacttctggatcagctgggtgcgccagatgc
ccgggaaaggcctggagtggatggggagggttgatcctggctactct
tatagcacctacagcccgtccttccaaggccacgtcaccatctcagc
tgacaagtctaccagcactgcctacctgcagtggaacagcctgaagg
cctcggacaccgccatgtattactgtgcgagagtacaatatagtggc
tactatgactggttcgaccctgggg ccagggaaccctggtcaccgt
ctcctca (SEQ ID NO: 55)

TABLE 4

Antigen WT1 (Ext002 #15)
Peptide RMFPNAPYL (SEQ ID NO: 1)

| CDRs: | 1 | 2 | 3 |
|---|---|---|---|
| VH | GYNFSNKWIG (SEQ ID NO: 56) | IIYPGYSDITYSPSFQG (SEQ ID NO: 57) | HTALAGFDY (SEQ ID NO: 58) |
| DNA | ggctacaactttagcaacaagtggatcggc (SEQ ID NO: 59) | atcatctatcccggttactcggacatcacctacagcccgtccttccaaggc (SEQ ID NO: 60) | cacacagctttggccggctttgactac (SEQ ID NO: 61) |
| VL | RASQNINKWLA (SEQ ID NO: 62) | KASSLES (SEQ ID NO: 63) | QQYNSYAT (SEQ ID NO: 64) |
| DNA | Cgggccagtcagaatatcaataagtggctggcc (SEQ ID NO: 65) | aaggcgtctagtttagaaagt (SEQ ID NO: 66) | caacaatataatagttatgcgacg (SEQ ID NO: 67) |
| Full VH | QVQLVQSGAEVKKPGESLKISCKGSGYNFSNKWIGWVRQLPGRGLEWIAIIYPGYSDITYSPSFQGRVTISADTSINTAYLHWHSLKASDTAMYYCVRHTALAGFDYWGLGTLVTVSS (SEQ ID NO: 68) | | |

TABLE 4-continued

Antigen WT1 (Ext002 #15)
Peptide RMFPNAPYL (SEQ ID NO: 1)

| CDRs: | 1 | 2 | 3 |
|---|---|---|---|

DNA caggtgcagctggtgcagtctggagcagaggtgaaaaagcccggagag
tctctgaagatctcctgtaagggttctggctacaactttagcaacaag
tggatcggctgggtgcgccaattgcccgggagaggcctggagtggata
gcaatcatctatcccggttactcggacatcacctacagcccgtccttc
caaggccgcgtcaccatctccgccgacacgtccattaacaccgcctac
ctgcactggcacagcctgaaggcctcggacaccgccatgtattattgt
gtgcgacacacagctttggccggctttgactactggggcctgggcacc
ctggtcaccgtctcctca (SEQ ID NO: 69)

Full
VL DIQMTQSPSTLSASVGDRVTITCRASQNINKWLAWYQQRPGKAPQLLI
YKASSLESGVPSRFSGSGSGTEYTLTISSLQPDDFATYYCQQYNSYAT
FGQGTKVEIKR (SEQ ID NO: 70)

DNA gacatccagatgacccagtctccttccaccctgtctgcatctgtagga
gacagagtcacaatcacttgccgggccagtcagaatatcaataagtgg
ctggcctggtatcagcagagaccagggaaagcccctcagctcctgatc
tataaggcgtctagtttagaaagtggggtcccatctaggttcagcggc
agtggatctgggacagaatacactctcaccatcagcagcctgcagcct
gatgattttgcaacttattactgccaacaatataatagttatgcgacg
ttcggccaagggaccaaggtggaaatcaaacgt
(SEQ ID NO: 71)

scFv DIQMTQSPSTLSASVGDRVTITCRASQNINKWLAWYQQRPGKAPQLLI
YKASSLESGVPSRFSGSGSGTEYTLTISSLQPDDFATYYCQQYNSYAT
FGQGTKVEIKRSRGGGGSGGGGSGGGGSLEMAQVQLVQSGAEVKKPGE
SLKISCKGSGYNFSNKWIGWVRQLPGRGLEWIAIIYPGYSDITYSPSF
QGRVTISADTSINTAYLHWHSLKASDTAMYYCVRHTALAGFDYWGLGT
LVTVSS (SEQ ID NO: 72)

DNA gacatccagatgacccagtctccttccaccctgtctgcatctgtagga
gacagagtcacaatcacttgccgggccagtcagaatatcaataagtgg
ctggcctggtatcagcagagaccagggaaagcccctcagctcctgatc
tataaggcgtctagtttagaaagtggggtcccatctaggttcagcggc
agtggatctgggacagaatacactctcaccatcagcagcctgcagcct
gatgattttgcaacttattactgccaacaatataatagttatgcgacg
ttcggccaagggaccaaggtggaaatcaaacgt**tctagaggtggtggt
ggtagcggcggcggcggctctggtggtggtggatcccctcgagatgg**cc
caggtgcagctggtgcagtctggagcagaggtgaaaaagcccggagag
tctctgaagatctcctgtaagggttctggctacaactttagcaacaag
tggatcggctgggtgcgccaattgcccgggagaggcctggagtggata
gcaatcatctatcccggttactcggacatcacctacagcccgtccttc
caaggccgcgtcaccatctccgccgacacgtccattaacaccgcctac
ctgcactggcacagcctgaaggcctcggacaccgccatgtattattgt
gtgcgacacacagctttggccggctttgactactggggcctgggcacc
ctggtcaccgtctcctca (SEQ ID NO: 73)

TABLE 5

Antigen WT1 (Ext002 #18)
Peptide RMFPNAPYL (SEQ ID NO: 1)

| CDRs: | 1 | 2 | 3 |
|---|---|---|---|
| VH | GFTFDDYGMS (SEQ ID NO: 74) | GINWNGGSTGYADSVRG (SEQ ID NO: 75) | ERGYGYHDPHDY (SEQ ID NO: 76) |
| DNA | gggttcacctttgatgattatggcatgagc (SEQ ID NO: 77) | ggtattaattggaatggtggtagcacaggttatgcagactctgtgaggggc (SEQ ID NO: 78) | gagcgtggctacgggtaccatgatccccatgactac (SEQ ID NO: 79) |
| VL | GRNNIGSKSVH (SEQ ID NO: 80) | DDSDRPS (SEQ ID NO: 81) | QVWDSSSDHVV (SEQ ID NO: 82) |
| DNA | gggagaaacaacattggaagtaaaagtgtgcac (SEQ ID NO: 83) | gatgatagcgaccggccctca (SEQ ID NO: 84) | caggtgtgggatagtagtagtgatcatgtggta (SEQ ID NO: 85) |

TABLE 5-continued

Antigen WT1 (Ext002 #18)
Peptide RMFPNAPYL (SEQ ID NO: 1)

| CDRs: | 1 | 2 | 3 |
|---|---|---|---|

| | |
|---|---|
| Full VH | EVQLVQSGGGVVRPGGSLRLSCAASGFTFDDYGMSWVRQAPGKGLE WVSGINWNGGSTGYADSVRGRFTISRDNAKNSLYLQMNSLRAEDTA LYYCARERGYGYHDPHDYWGQGTLVTVSS (SEQ ID NO: 86) |
| DNA | gaagtgcagctggtgcagtctggggggaggtgtggtacggcctgggg ggtccctgagactctcctgtgcagcctctgggttcacctttgatga ttatggcatgagctgggtccgccaagctccagggaaggggctggag tgggtctctggtattaattggaatggtggtagcacaggttatgcag actctgtgaggggccgattcaccatctccagagacaacgccaagaa ctccctgtatctgcaaatgaacagtctgagagccgaggacacggcc ttgtattactgtgcgagagagcgtggctacgggtaccatgatcccc atgactactggggccaaggcaccctggtgaccgtctcctca (SEQ ID NO: 87) |
| Full VL | QSVVTQPPSVSVAPGKTARITCGRNNIGSKSVHWYQQKPGQAPVLV VYDDSDRPSGIPERFSGSNSGNTATLTISRVEAGDEADYYCQVWDS SSDHVVFGGGTKLTVLG (SEQ ID NO: 88) |
| DNA | cagtctgtcgtgacgcagccgccctcggtgtcagtggccccaggaa agacggccaggattacctgtgggagaaacaacattggaagtaaaag tgtgcactggtaccagcagaagccaggccaggcccctgtgctggtc gtctatgatgatagcgaccggccctcagggatccctgagcgattct ctggctccaactctgggaacacggccaccctgaccatcagcagggt cgaagccggggatgaggccgactattactgtcaggtgtgggatagt agtagtgatcatgtggtattcggcggagggaccaagctgaccgtcc taggt (SEQ ID NO: 89) |
| scFv | QSVVTQPPSVSVAPGKTARITCGRNNIGSKSVHWYQQKPGQAPVLV VYDDSDRPSGIPERFSGSNSGNTATLTISRVEAGDEADYYCQVWDS SSDHVVFGGGTKLTVLGSRGGGGSGGGGSGGSLEMAEVQLVQSGGG VVRPGGSLRLSCAASGFTFDDYGMSWVRQAPGKGLEWVSGINWNGG STGYADSVRGRFTISRDNAKNSLYLQMNSLRAEDTALYYCARERGY GYHDPHDYWGQGTLVTVSS (SEQ ID NO: 90) |
| DNA | cagtctgtcgtgacgcagccgccctcggtgtcagtggccccaggaa agacggccaggattacctgtgggagaaacaacattggaagtaaaag tgtgcactggtaccagcagaagccaggccaggcccctgtgctggtc gtctatgatgatagcgaccggccctcagggatccctgagcgattct ctggctccaactctgggaacacggccaccctgaccatcagcagggt cgaagccggggatgaggccgactattactgtcaggtgtgggatagt agtagtgatcatgtggtattcggcggagggaccaagctgaccgtcc taggttctagaggtggtggtggtagcggcggcggcggctctggtgg atccctcgagatggccgaagtgcagctggtgcagtctggggggaggt gtggtacggcctggggggtccctgagactctcctgtgcagcctctg ggttcacctttgatgattatggcatgagctgggtccgccaagctcc agggaaggggctggagtgggtctctggtattaattggaatggtggt agcacaggttatgcagactctgtgaggggccgattcaccatctcca gagacaacgccaagaactccctgtatctgcaaatgaacagtctgag agccgaggacacggccttgtattactgtgcgagagagcgtggctac gggtaccatgatccccatgactactggggccaaggcaccctggtga ccgtctcctca (SEQ ID NO: 91) |

TABLE 6

Antigen WT1 (Ext002 #23)
Peptide RMFPNAPYL (SEQ ID NO: 1)

| CDRs: | 1 | 2 | 3 |
|---|---|---|---|
| VH | GFSVSGTYMG (SEQ ID NO. 92) | LLYSGGGTYHPASLQG (SEQ ID NO. 93) | GGAGGGHFDS (SEQ ID NO. 94) |
| DNA | gggttctccgtcagtg gcacctacatgggc (SEQ ID NO. 95) | cttctttatagtggtg gcggcacataccaccc agcgtccctgcagggc (SEQ ID NO. 96) | gaggggcaggaggtgg ccactttgactcc (SEQ ID NO. 97) |
| VL | TGSSSNIGAGYDVH (SEQ ID NO. 98) | GNSNRPS (SEQ ID NO. 99) | AAWDDSLNGYV (SEQ ID NO. 100) |

TABLE 6-continued

Antigen WT1 (Ext002 #23)
Peptide RMFPNAPYL (SEQ ID NO. 1)

| CDRs: | 1 | 2 | 3 |
|---|---|---|---|
| DNA | actgggagcagctcca acatcggggcaggtta tgatgtacac (SEQ ID NO. 101) | ggtaacagcaatcggc cctca (SEQ ID NO. 102) | gcagcatgggatgaca gcctgaatggttatgt c (SEQ ID NO. 103) |

| | |
|---|---|
| Full VH | EVQLVETGGGLLQPGGSLRLSCAASGFSVSGTYMGWVRQAPGKGLEW VALLYSGGGTYHPASLQGRFIVSRDSSKNMVYLQMNSLKAEDTAVYY CAKGGAGGGHFDSWGQGTLVTVSS (SEQ ID NO. 104) |
| DNA | gaggtgcagctggtggagaccggaggaggcttgctccagccggggggg gtccctcagactctcctgtgcagcctctgggttctccgtcagtggca cctacatgggctgggtccgccaggctccagggaagggactggagtgg gtcgcacttctttatagtggtggcggcacataccacccagcgtccct gcagggccgattcatcgtctccagagacagctccaagaatatggtct atcttcaaatgaatagcctgaaagccgaggacacggccgtctattac tgtgcgaaaggaggggcaggaggtggccactttgactcctggggcca aggcaccctggtgaccgtctcctca (SEQ ID NO. 105) |
| Full VL | QSVLTQPPSVSGAPGQRVTISCTGSSSNIGAGYDVHWYQQLPGTAPK LLIYGNSNRPSGVPDRFSGSKSGTSASLAISGLQSEDEADYYCAAWD DSLNGYVFGTGTKLTVLG (SEQ ID NO. 106) |
| DNA | cagtctgtgttgacgcagccgccctcagtgtctggggccccagggca gagggtcaccatctcctgcactgggagcagctccaacatcggggcag gttatgatgtacactggtaccagcagcttccaggaacagcccccaaa ctcctcatctatggtaacagcaatcggccctcaggggtccctgaccg attctctggctccaagtctggcacctcagcctccctggccatcagtg ggctccagtctgaggatgaggctgattattactgtgcagcatgggat gacagcctgaatggttatgtcttcggaactgggaccaagctgaccgt cctaggt (SEQ ID NO. 107) |
| scFv | QSVLTQPPSVSGAPGQRVTISCTGSSSNIGAGYDVHWYQQLPGTAPK LLIYGNSNRPSGVPDRFSGSKSGTSASLAISGLQSEDEADYYCAAWD DSLNGYVFGTGTKLTVLGSRGGGGSGGGGSGGGGSLEMAEVQLVETG GGLLQPGGSLRLSCAASGFSVSGTYMGWVRQAPGKGLEWVALLYSGG GTYHPASLQGRFIVSRDSSKNMVYLQMNSLKAEDTAVYYCAKGGAGG GHFDSWGQGTLVTVSS (SEQ ID NO. 108) |
| DNA | cagtctgtgttgacgcagccgccctcagtgtctggggccccagggca gagggtcaccatctcctgcactgggagcagctccaacatcggggcag gttatgatgtacactggtaccagcagcttccaggaacagcccccaaa ctcctcatctatggtaacagcaatcggccctcaggggtccctgaccg attctctggctccaagtctggcacctcagcctccctggccatcagtg ggctccagtctgaggatgaggctgattattactgtgcagcatgggat gacagcctgaatggttatgtcttcggaactgggaccaagctgaccgt cctaggttctagaggtggtggtggtagcggcggcggcggctctggtg gtggtggatccctcgagatggccgaggtgcagctggtggagaccgga ggaggcttgctccagccggggggtccctcagactctcctgtgcagc ctctgggttctccgtcagtggcacctacatgggctgggtccgccagg ctccagggaagggactggagtgggtcgcacttctttatagtggtggc ggcacataccacccagcgtcctgcagggccgattcatcgtctccag agacagctccaagaatatggtctatcttcaaatgaatagcctgaaag ccgaggacacggccgtctattactgtgcgaaaggaggggcaggaggt ggccactttgactcctggggccaaggcaccctggtgaccgtctcctc a (SEQ ID NO. 109) |

TABLE 7

| Antigen | CD3/L2K |
|---|---|
| Full VL | DDIVLTQSPATLSLSPGERATLSCRASQSVS YMNWYQQKPGKAPKRWIYDTSKVASGVPARF SGSGSGTDYSLTINSLEAEDAATYYCQQWSS NPLTFGGGTKVEIK (SEQ ID NO: 111) |
| Full VH | DVQLVQSGAEVKKPGASVKVSCKASGYTFTR YTMHWVRQAPGQGLEWIGYINPSRGYTNYAD SVKGRFTITTDKSTSTAYMELSSLRSEDTAT YYCARYYDDHYCLDYWGQGTTVTVSS (SEQ ID NO: 112) |
| scFv | DVQLVQSGAEVKKPGASVKVSCKASGYTFTR YTMHWVRQAPGQGLEWIGYINPSRGYTNYAD SVKGRFTITTDKSTSTAYMELSSLRSEDTAT YYCARYYDDHYCLDYWGQGTTVTVSSGEGTS TGSGGSGSGGADDIVLTQSPATLSLSPGER ATLSCRASQSVSYMNWYQQKPGKAPKRWIYD TSKVASGVPARFSGSGSGTDYSLTINSLEAE DAATYYCQQWSSNPLTFGGGTKVEIK (SEQ ID NO: 113) |

TABLE 7-continued

| Antigen | CD3/L2K |
|---|---|
| DNA (without signal sequence and his tag) | caggctgtcgtgactcagcctccttctgctt ctggcacccctggccagagagtgaccatctc ctgctccggctcctcctccaacatcggctcc aacaccgtgaactggtatcagcaggtgcccg gcaccgcccccaagctgctgatctactctaa caaccagcggccctccggcgtgcccgacaga ttctctggctctaagtccggcacctccgcct ccctggctatctctggcctgcagtctgagga cgaggccgactactactgcgccgcctgggac gattctctgaacggctgggtgttcggcggag gcaccaagctgacagtgctgggaagtagagg cggtggcggatctggtggcggaggatctggc ggaggggctctctggaaatggcccagatgc agctggtgcagtctggcgccgaagtgaaaga gcctggcgagtccctgcggatctcctgcaag ggctccggctacagctttaccaacttctgga tcagctgggtgcgacagatgcccggcaaggg cctggaatggatgggcagagtggaccccggc tactcctactccacctactcccccagcttcc agggccacgtgaccatcagcgccgacaagtc tacctccaccgcctacctgcagtggaactcc ctgaaggcctccgacaccgccatgtactact gtgcccgggtgcagtacagccggctactacga ttggttcgaccctggggccagggcaccctc gtgacagtgtctagtggcggggaggatccg acgtgcagctggtgcagagcggagctgaagt gaagaaacctggcgcctccgtgaaggtgtcc tgcaaagctagcggctataccttcacccggt acaccatgcactgggtgcgccaggcacctgg acagggactggaatggatcggctacatcaac cctcccggcgtacaccaactaccgccgact ctgtgaagggccggttcaccatcaccaccga taagtccaccagcaccgcttacatggaactg tcctccctgagatccgaggacaccgctacct actattgcgcccggctactacgacgaccacta ctgcctggactactggggacagggaaccaca gtgaccgtgtcctctggcgagggcacctcta ctggatctgggggaagtggtggttctggcgg cgctgacgacatcgtgctgacccagtctcca gccaccctgtctctgagcccaggcgagagag ctaccctgtcctgcagagcctcccagtccgt gtcctacatgaattggtatcagcagaagcct ggcaaggcccctaagcggttggatctacgaca cctccaaggtggcctctggcgtgccagcccg gttttccggatctggctctggcaccgactac tccctgaccatcaacagcctggaagccgagg acgctgccacctattactgccagcagtggtc ctccaacccctgaccttggaggcggcacc aaggtggaaatcaag (SEQ ID NO: 114) |
| DNA (with signal sequence and hexahistidine tag) | atgggctggtcctgcatcatcctgtttctgg tggctaccgccaccggccaggctgtcgtgac tcagcctccttctgcttctggcacccctggc cagagagtgaccatctcctgctccggctcct cctccaacatcggctccaacaccgtgaactg gtatcagcaggtgcccggcaccgcccccaag ctgctgatctactctaacaaccagcggccct ccggcgtgcccgacagattctctggctctaa gtccggcacctccgcctccctggctatctct | |

TABLE 7-continued

| Antigen | CD3/L2K |
|---|---|
| | ggcctgcagtctgaggacgaggccgactact actgcgccgcctgggacgattctctgaacgg ctgggtgttcggcggaggcaccaagctgaca gtgctgggaagtagaggcggtggcggatctg gtggcggaggatctggcggaggggctctct ggaaatggcccagatgcagctggtgcagtct ggcgccgaagtgaaagagcctggcgagtccc tgcggatctcctgcaagggctccggctacag ctttaccaacttctggatcagctgggtgcga cagatgcccggcaagggcctggaatggatgg gcagagtggaccccggctactcctactccac ctactcccccagcttccagggccacgtgacc atcagcgccgacaagtctacctccaccgcct acctgcagtggaactccctgaaggcctccga caccgccatgtactactgtgcccgggtgcag tacagcggctactacgattggttcgacccct ggggccagggcaccctcgtgacagtgtctag tggcggggaggatccgacgtgcagctggtg cagagcggagctgaagtgaagaaacctggcg cctccgtgaaggtgtcctgcaaagctagcgg ctataccttcacccggtacaccatgcactgg gtgcgccaggcacctggacagggactggaat ggatcggctacatcaaccccctcccggggcta caccaactacgccgactctgtgaagggccgg ttcaccatcaccaccgataagtccaccagca ccgcttacatggaactgtcctccctgagatc cgaggacaccgctacctactattgcgcccgg tactacgacgaccactactgcctggactact ggggacagggaaccacagtgaccgtgtcctc tggcgagggcacctctactggatctggggga agtggtggttctggcggcgctgacgacatcg tgctgacccagtctccagccaccctgtctct gagcccaggcgagagagctaccctgtcctgc agagcctcccagtccgtgtcctacatgaatt ggtatcagcagaagcctggcaaggcccctaa gcggtggatctacgacacctccaaggtggcc tctggcgtgccagcccggttttccggatctg gctctggcaccgactactccctgaccatcaa cagcctggaagccgaggacgctgccacctat tactgccagcagtggtcctccaacccctga cctttggaggcggcaccaaggtggaaatcaa gcaccaccatcatcaccactgatag (SEQ ID NO: 115) |

In one embodiment, the ESK1-bi-specific antibody comprises a first antigen-binding portion that specifically binds to WT1/HLA-A2 and comprises one of the amino acid sequences of an WT1/HLA-A2 antibody as set forth in Tables 1-6 and an antigen-binding portion that binds to CD3 and comprises an amino acid sequence shown in Table 7 above. In one embodiment, the antibody has the amino acid sequence shown in FIG. 10 (SEQ ID NO: 110). In another embodiment, the ESK1-bi-specific antibody comprises a first antigen-binding portion that specifically binds to WT1/HLA-A2 and comprises one of the amino acid sequences of an WT1/HLA-A2 antibody as set forth in Table 8 and an antigen-binding portion that binds to OKT3 and comprises an amino acid sequence shown in Table 9.

TABLE 8

| | Antigen WT1 | | |
|---|---|---|---|
| CDRs: | 1 | 2 | 3 |
| VH | GYSFTNFWIS (SEQ ID NO: 116) | RVDPGYSYSTYSPSFQ (SEQ ID NO: 117) | VQYSGYYDWFDP (SEQ ID NO: 118) |
| DNA | ggatacagcttcacca acttctggatcagc (SEQ ID NO: 119) | agggttgatcctggct actcttatagcaccta cagcccgtccttccaa ggc (SEQ ID NO: 120) | gtacaatatagtggct actatgactggttcga cccc (SEQ ID NO: 121) |

TABLE 8-continued

Antigen WT1

| CDRs: | 1 | 2 | 3 |
|---|---|---|---|
| VL | SGSSSNIGSNTVN (SEQ ID NO: 122) | SNNQRPS (SEQ ID NO: 123) | AAWDDSLNGWV (SEQ ID NO: 124) |
| DNA | tctggaagcagctcca acatcggaagtaatac tgtaaac (SEQ ID NO: 125) | agtaataatcagcggc cctca (SEQ ID NO: 126) | gcagcatgggatgaca gcctgaatggttgggt g (SEQ ID NO: 127) |

Full VH: QMQLVQSGAEVKEPGESLRISCKGSGYSFTNFWISWVRQMPGKGLEW
MGRVDPGYSYSTYSPSFQGHVTISADKSTSTAYLQWNSLKASDTAMY
YCARVQYSGYYDWFDPWGQGTLVTVSSASTKGPSVFPLAPSSKSTSG
GTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWY
VDGVEVHNAKTKPREEQYASTYRVVSVLTVLHQDWLNGKEYKCKVSN
KALPAPIEKTISKAKGQPREPQVYTLPPSRDELTKNQVSLTCLVKGF
YPSDIAVEWESNGQPENNYKTTPPVLDSDGSFFLYSRLTVDKSRWQQ
GNVFSCSVMHEALHNHYTQKSLSLSPGK* (SEQ ID NO: 128)

DNA: cagatgcagctggtgcagtctggcgccgaagtgaaagagcctggcga
gtccctgcggatctcctgcaagggctccggctactcctttaccaact
tctggatcagctgggtgcgacagatgcccggcaagggcctggaatgg
atgggcagagtggaccccggctacagctactccacctactcccccag
cttccagggccacgtgaccatctccgccgacaagtctacctccaccg
cctacctgcagtggaactccctgaaggcctccgacaccgccatgtac
tactgcgccagagtgcagtacagcggctactacgattggttcgaccc
ctgggggccagggcaccctcgtgacagtgtcctctgcttccaccaagg
gcccatcggtcttcccctggcaccctcctccaagagcacctctggg
ggcacagcggccctgggctgcctggtcaaggactacttccccgaacc
ggtgacggtgtcgtggaactcaggcgccctgaccagcggcgtgcaca
ccttcccggccgtcctacagtcctcaggactctactccctcagcagc
gtggtgaccgtgccctccagcagcttgggcacccagacctacatctg
caacgtgaatcacaagcccagcaacaccaaggtggacaagagagttg
agcccaaatcttgtgacaaaactcacacatgcccaccgtgcccagca
cctgaactcctggggggaccgtcagtcttcctcttccccccaaaacc
caaggacaccctcatgatctcccggacccctgaggtcacatgcgtgg
tggtggacgtgagccacgaagaccctgaggtcaagttcaactggtac
gtggacggcgtggaggtgcataatgccaagacaaagccgcgggagga
gcagtacgccagcacgtaccgtgtggtcagcgtcctcaccgtcctgc
accaggactggctgaatggcaaggagtacaagtgcaaggtctccaac
aaagcccctcccagcccccatcgagaaaaccatctccaaagccaagg
gcagccccgagaaccacaggtgtacaccctgcccccatcccgggatg
agctgaccaagaaccaggtcagcctgacctgcctggtcaaaggcttc
tatcccagcgacatcgccgtggagtgggagagcaatgggcagccgga
gaacaactacaagaccacgcctcccgtgctggactccgacggctcct
tcttcctctacagcaggctcaccgtggacaagagcaggtggcagcag
gggaacgtcttctcatgctccgtgatgcatgaggctctgcacaacca
ctacacgcagaagagcctctccctgtctccgggtaaatga
(SEQ ID NO: 129)

Full VL: QAVVTQPPSASGTPGQRVTISCSGSSSNIGSNTVNWYQQVPGTAPKL
LIYSNNQRPSGVPDRFSGSKSGTSASLAISGLQSEDEADYYCAAWDD
SLNGWVFGGGTKLTVLGQPKANPTVTLFPPSSEELQANKATLVCLIS
DFYPGAVTVAWKADGSPVKAGVETTKPSKQSNNKYAASSYLSLTPEQ
WKSHRSYSCQVTHEGSTVEKTVAPTECS* (SEQ ID NO: 130)

DNA: CAGGCTGTCGTGACTCAGCCTCCTTCTGCTTCTGGCACCCCTGGCCA
GAGAGTGACCATCTCCTGCTCCGGCTCCTCCTCCAACATCGGCTCCA
ACACCGTGAACTGGTATCAGCAGGTGCCCGGCACCGCCCCCAAGCTG
CTGATCTACTCTAACAACCAGCGGCCCTCCGGCGTGCCCGACAGATT
CTCTGGCTCTAAGTCCGGCACCTCCGCCTCCCTGGCTATCTCTGGCC
TGCAGTCTGAGGACGAGGCCGACTACTACTGCGCCGCCTGGGACGAT
TCTCTGAACGGCTGGGTGTTCGGCGGAGGCACCAAGCTGACAGTGCT
GGGCCAGCCTAAGGCCAACCCTACCGTGACCCTGTTCCCCCCATCCT
CCGAGGAACTGCAGGCTAACAAGGCCACCCTCGTGTGCCTGATCTCC
GACTTCTACCCTGGCGCCGTGACCGTGGCCTGGAAGGCTGATGGATC
TCCTGTGAAGGCCGGCGTGGAAACCACCAAGCCCTCCAAGCAGTCCA
ACAACAAATACGCCGCCTCCTCCTACCTGTCCCTGACCCCTGAGCAG
TGGAAGTCCCACCGGTCCTACAGCTGCCAAGTGACCCACGAGGGCTC
CACCGTGGAAAAGACCGTGGCTCCTACCGAGTGCTCCTAG
(SEQ ID NO: 131)

scFv: QAVVTQPPSASGTPGQRVTISCSGSSSNIGSNTVNWYQQVPGTAPKL
LIYSNNQRPSGVPDRFSGSKSGTSASLAISGLQSEDEADYYCAAWDD
SLNGWVFGGGTKLTVLGSRGGGGSGGGGSGGGGSLEMAQMQLVQSGA

TABLE 8-continued

Antigen WT1

| CDRs: | 1 | 2 | 3 |
|---|---|---|---|

EVKEPGESLRISCKGSGYSFTNFWISWVRQMPGKGLEWMGRVDPGYS
YSTYSPSFQGHVTISADKSTSTAYLQWNSLKASDTAMYYCARVQYSG
YYDWFDPWGQGTLVTVSS (SEQ ID NO: 132)

scFv DNA
caggctgtggtgactcagccaccctcagcgtctgggaccccgggca
gagggtcaccatctcttgttctggaagcagctccaacatcggaagta
atactgtaaactggtaccagcaggtcccaggaacggcccccaaactc
ctcatctatagtaataatcagcggccctcaggggtccctgaccgatt
ctctggctccaagtctggcacctcagcctccctggccatcagtgggc
tccagtctgaggatgaggctgattattactgtgcagcatgggatgac
agcctgaatggttgggtgttcggcggagggaccaagctgaccgtcct
aggttctagaggtggtggtggtagcggcggcggcggctctggtggtg
gtggatccctcgagatggcccagatgcagctggtgcagtccggagca
gaggtgaaagagcccggggagtctctgaggatctcctgtaagggttc
tggatacagcttcaccaacttctggatcagctgggtgcgccagatgc
ccgggaaaggcctggagtggatggggagggttgatcctggctactct
tatagcacctacagcccgtccttccaaggccacgtcaccatctcagc
tgacaagtctaccagcactgcctacctgcagtggaacagcctgaagg
cctcggacaccgccatgtattactgtgcgagagtacaatatagtggc
tactatgactggttcgacccctggggccagggaaccctggtcaccgt
ctcctca (SEQ ID NO: 133)

TABLE 9

| Antigen | OKT3 |
|---|---|
| Full VH | QVQLVQSGGGVVQPGRSLRLSCKASGYTFTRYTMH WVRQAPGKGLEWIGYINPSRGYTNYNQKFKDRFTI SRDNSKNTAFLQMDSLRPEDTGVYFCARYYDDHYC LDYWGQGTPVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSN TKVDKRVEPKSCDKTHTCPPCPAPELLGGPSVFLF PPKPKDTLMISRTPEVTCVVVDVSHEDPEVKFNWY VDGVEVHNAKTKPREEQYASTYRVVSVLTVLHQDW LNGKEYKCKVSNKALPAPIEKTISKAKGQPREPQV YTLPPSRDELTKNQVSLTCLVKGFYPSDIAVEWES NGQPENNYKTTPPVLDSDGSFLLYSKLTVDKSRWQ QGNVFSCSVMHEALHNHYTQKSLSLSPGK* (SEQ ID NO: 134) |
| DNA | CAGGTGCAGCTGGTGCAGTCCGGCGGCGGCGTGGT GCAGCCCGGCCGGTCCCTGCGGCTGTCCTGCAAGG CCTCCGGCTACACCTTCACCCGGTACACCATGCAC TGGGTGCGCCAGGCCCCCGGCAAGGGCCTGGAGTG GATCGGCTACATCAACCCCTCCCGGGGCTACACCA ACTACAACCAGAAGTTCAAGGACCGGTTCACCATC TCCCGGGACAACTCCAAGAACACCGCCTTCCTGCA GATGGACTCCCTGCGGCCCGAGGACACCGGCGTGT ACTTCTGCGCCCGGTACTACGACGACCACTACTGC CTGGACTACTGGGGCCAGGGCACCCCCGTGACCGT GTCCTCCGCCTCCACCAAGGGCCCATCGGTCTTCC CCCTGGCACCCTCCTCCAAGAGCACCTCTGGGGGC ACAGCGGCCCTGGGCTGCCTGGTCAAGGACTACTT CCCCGAACCGGTGACGGTGTCGTGGAACTCAGGCG CCCTGACCAGCGGCGTGCACACCTTCCCGGCCGTC CTACAGTCCTCAGGACTCTACTCCCTCAGCAGCGT GGTGACCGTGCCCTCCAGCAGCTTGGGCACCCAGA CCTACATCTGCAACGTGAATCACAAGCCCAGCAAC ACCAAGGTGGACAAGAGAGTTGAGCCCAAATCTTG TGACAAAACTCACACATGCCCACCGTGCCCAGCAC CTGAACTCCTGGGGGGACCGTCAGTCTTCCTCTTC CCCCCAAAACCCAAGGACACCCTCATGATCTCCCG GACCCCTGAGGTCACATGCGTGGTGGTGGACGTGA GCCACGAAGACCCTGAGGTCAAGTTCAACTGGTAC GTGGACGGCGTGGAGGTGCATAATGCCAAGACAAA GCCGCGGGAGGAGCAGTACGCCAGCACGTACCGTG TGGTCAGCGTCCTCACCGTCCTGCACCAGGACTGG CTGAATGGCAAGGAGTACAAGTGCAAGGTCTCCAA CAAAGCCCTCCCAGCCCCCATCGAGAAAACCATCT CCAAAGCCAAAGGGCAGCCCCGAGAACCACAGGTG TACACCCTGCCCCCATCCCGGGATGAGCTGACCAA GAACCAGGTCAGCCTGACCTGCCTGGTCAAAGGCT TCTATCCCAGCGACATCGCCGTGGAGTGGGAGAGC AATGGGCAGCCGGAGAACAACTACAAGACCACGCC TCCCGTGCTGGACTCCGACGGCTCCTTCCTCCTCT ACAGCAAGCTCACCGTGGACAAGAGCAGGTGGCAG CAGGGGAACGTCTTCTCATGCTCCGTGATGCATGA GGCTCTGCACAACCACTACACGCAGAAGAGCCTCT CCCTGTCTCCGGGTAAATGA (SEQ ID NO: 135) |
| Full VL | DIQMTQSPSSLSASVGDRVTITCSASSSVSYMNWY QQTPGKAPKRWIYDTSKLASGVPSRFSGSGSGTDY TFTISSLQPEDIATYYCQQWSSNPFTFGQGTKLQI TRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNR GEC* (SEQ ID NO: 136) |
| DNA | GACATCCAGATGACCCAGTCCCCCTCCTCCCTGTC CGCCTCCGTGGGCGACCGGGTGACCATCACCTGCT CCGCCTCCTCCTCCGTGTCCTACATGAACTGGTAC CAGCAGACCCCCGGCAAGGCCCCCAAGCGGTGGAT CTACGACACCTCCAAGCTGGCCTCCGGCGTGCCCT CCCGGTTCTCCGGCTCCGGCTCCGGCACCGACTAC ACCTTCACCATCTCCTCCCTGCAGCCCGAGGACAT CGCCACCTACTACTGCCAGCAGTGGTCCTCCAACC CCTTCACCTTCGGCCAGGGCACCAAGCTGCAGATC ACCCGGACCGTGGCCGCCCCCTCCGTGTTCATCTT CCCCCCCTCCGACGAGCAGCTGAAGTCCGGCACCG CCTCCGTGGTGTGCCTGCTGAACAACTTCTACCCC CGGGAGGCCAAGGTGCAGTGGAAGGTGGACAACGC CCTGCAGTCCGGCAACTCCCAGGAGTCCGTGACCG AGCAGGACTCCAAGGACTCCACCTACTCCCTGTCC TCCACCCTGACCCTGTCCAAGGCCGACTACGAGAA GCACAAGGTGTACGCCTGCGAGGTGACCCACCAGG GCCTGTCCTCCCCCGTGACCAAGTCCTTCAACCGG GGCGAGTGCTAG (SEQ ID NO: 137) |

The recombinant bi-specific antibodies of the present disclosure also include substantially homologous polypeptides having antigen-binding portions that are at least 70%, at least 75%, at least 80%, at least 85%, at least 90%, at least 95%, at least 97%, at least 98%, or at least 99% identical to the peptides described in Tables 1-9.

Bi-specific antibodies according to the present disclosure may be prepared by any of a number of conventional techniques. For example, they may be produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988). Certain of the techniques involve isolating a nucleic acid encoding a polypeptide chain (or portion thereof) of an antibody of interest, and manipulating the nucleic acid through recombinant DNA technology. The nucleic acid may be fused to another nucleic acid of interest, or altered (e.g., by mutagenesis or other conventional techniques) to add, delete, or substitute one or more amino acid residues.

Any expression system known in the art can be used to make the recombinant bi-specific antibodies of the present disclosure. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821. Appropriate cloning and expression vectors for use with bacterial, fungal, yeast, and mammalian cellular hosts are described in the art, e.g., by Pouwels et al., Cloning Vectors: A Laboratory Manual, Elsevier, N.Y., 1985.

The transformed cells can be cultured under conditions that promote expression of the polypeptide, and the polypeptide recovered by conventional protein purification procedures. One such purification procedure includes the use of affinity chromatography, e.g., over a matrix having all or a portion of the antigen bound thereto. Polypeptides contemplated for use herein include substantially homogeneous recombinant bi-specific antibodies substantially free of contaminating endogenous materials.

In one aspect, bi-specific antibodies according to the present disclosure are produced from host cells transformed with a recombinant expression vector encoding a peptide having a first antigen-binding portion and a second antigen binding portion. In another aspect, a bi-specific antibody of the present disclosure is produced from two separate antibodies, i.e., an antibody having a first antigen-binding portion and an antibody having a second antigen binding portion, that are linked, e.g., using disulfide bonds.

The amino acid sequence of the bi-specific antibodies disclosed herein may be verified by any means known in the art, and may be identical to the sequences disclosed herein in Tables 1-9, or may differ from those sequences at one or more amino acid residues as result of processing. For example, on all or a portion of the substantially homogenous bi-specific antibodies, a C-terminal amino acid from either the light chain or the heavy chain (or relevant single-chain molecule) may be removed, by proteolytic processing or other processing that occurs during culture, for example, processing of C-terminal Lys residues. Alternatively, more than one C-terminal amino acid residue may be removed, for example two C-terminal amino acids, or three, four or five C-terminal amino acids. Similarly, N-terminal amino acids may be absent, for example, one, two, three, four or five N-terminal amino acids may be absent.

Alternatively, or additionally, the bi-specific antibodies may undergo post-translational modifications, for example but not limited to, a glutamine may be cyclized or converted to pyroglutamic acid; additionally or alternatively, amino acids may undergo deamidation, isomerization, glycation and/or oxidation. The polypeptides of the invention may undergo additional post-translational modification, including glycosylation, for example N-linked or O-linked glycosylation, at sites that are well-known in the art. As described previously, changes may be made in the amino acid sequence of a polypeptide to preclude or minimize such alterations, or to facilitate them in circumstances where such processing is beneficial.

Bi-specific antibodies according to the present disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Additionally, single or multiple amino acid substitutions (e.g., conservative amino acid substitutions) made in a sequence described in any of Tables 1-9 (e.g., in the portion of the polypeptide outside the domain(s) forming intermolecular contacts) are encompassed by the present disclosure. Systematic substitution of one or more amino acids of a consensus sequence with a D-amino acid of the same type (e.g., D-lysine in place of L-lysine) may also be used, e.g., to generate more stable peptides. In addition, consensus sequences can be used to select amino acid residues for substitution; those of skill in the art recognize that additional amino acid residues may also be substituted. Constrained peptides comprising a consensus sequence or a substantially identical consensus sequence variation may be generated by methods known in the art (Rizo and Gierasch Ann. Rev. Biochem. 61:387 (1992)), incorporated herein by reference).

Bi-specific antibodies according to the present disclosure can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one aspect, the light or heavy chain constant region is a fragment, derivative, variant, or mutein of a naturally occurring constant region.

In another aspect, the invention relates to a derivative or analog of a bi-specific antibody of the present disclosure. A derivative can comprise any molecule or substance that imparts a desired property, such as increased half-life in a particular use. Examples of molecules that can be used to form a derivative include, but are not limited to, albumin (e.g., human serum albumin) and polyethylene glycol (PEG). Derivatives such as albumin-linked and PEGylated derivatives of antibodies can be prepared using techniques well known in the art. An analog may be a non-peptide analog of a bi-specific antibody described herein. Non-peptide analogs are commonly used in the pharmaceutical industry as drugs with properties analogous to those of the template peptide. These types of non-peptide compound are termed "peptide mimetics" or "peptidomimetics," see, for example, Fauchere, J. Adv. Drug Res. 15:29 (1986); Veber and Freidinger *TINS* p. 392 (1985); and Evans et al. *J. Med. Chem.* 30:1229 (1987), which are incorporated herein by reference. Peptide mimetics that are structurally similar to the bi-specific antibodies of the present disclosure may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art.

In one aspect, a recombinant bi-specific antibody according to the present disclosure comprises: (I) a first antigen-binding portion comprising one of: (A) a scFV comprising an amino acid sequence selected from the group consisting of SEQ ID NOS: 18, 36, 54, 72, 90, 108, and 132; or (B) a heavy chain variable domain (VH) and a light chain variable domain (VL), wherein the VH and VL, respectively, comprise amino acid sequences selected from the group consisting of SEQ ID NOS: (i) 14 and 16; (ii) 32 and 34; (iii) 50 and 52; (iv) 68 and 70; (v) 86 and 88; (vi) 104 and 106; and (vii) 128 and 130; or (C) (i) the following three VH complementarity determining regions (CDRs): (a) a VH CDR1 comprising the amino acid sequence selected from the group consisting of SEQ ID NOS: 2, 20, 38, 56, 74, 92 and 116; and (b) a VH CDR2 comprising an amino acid sequence selected from the group consisting of SEQ ID NOS: 3, 21, 39, 57, 75, 93, and 117; and (c) a VH CDR3 comprising an amino acid sequence selected from the group consisting of SEQ ID NOS: 4, 22, 40, 58, 76, 94, and 118; and (ii) the following three VL CDRs: (a) a VL CDR1 comprising an amino acid sequence selected from the group consisting of SEQ ID NOS: 8, 26, 44, 62, 80, 98, and 122; and (b) a VL CDR2 comprising an amino acid sequence selected from the group consisting of SEQ ID NOS: 9, 27, 45, 63, 81, 99, and 123; and (c) a VL CDR3 comprising an amino acid sequence selected from the group consisting of SEQ ID NOS: 10, 28, 46, 64, 82, 100, and 124; and (II) a second antigen-binding portion comprising (A) a single chain variable fragment (scFV) comprising the amino acid sequence set forth in SEQ ID NO: 113; or (B) a heavy chain variable domain (VH) and a light chain variable domain (VL), wherein the VH and VL, respectively, comprise the amino acid sequences set forth in SEQ ID NOS: 112 and 111 or SEQ ID NOS: 134 and 136.

In one aspect, the recombinant antibody comprises a first antigen-binding portion comprising one of: (A) a scFV comprising the amino acid sequence set forth in SEQ ID NO: 18; or (B) a VH comprising the amino acid sequence set forth in SEQ ID NO: 14 and a VL comprising the amino acid sequences set forth in SEQ ID NO: 16; or (C) a VH CDR1 comprising the amino acid sequence set forth in SEQ ID NO: 2; a VH CDR2 comprising the amino acid sequence set forth in SEQ ID NO: 3; a VH CDR3 comprising the amino acid sequence set forth in SEQ ID NO: 4; a VL CDR1 comprising the amino acid sequence set forth in SEQ ID NO: 8; a VL CDR2 comprising the amino acid sequence set forth in SEQ ID NO: 9; and a VL CDR3 comprising the amino acid sequence set forth in SEQ ID NO: 10.

In another aspect, the recombinant antibody comprises a first antigen-binding portion comprising one of: (A) a scFV comprising the amino acid sequence set forth in SEQ ID NO: 36; or (B) a VH comprising the amino acid sequence set forth in SEQ ID NO: 32 and a VL comprising the amino acid sequence set forth in SEQ ID NO: 34; or (C) a VH CDR1 comprising the amino acid sequence set forth in SEQ ID NO: 20; a VH CDR2 comprising the amino acid sequence set forth in SEQ ID NO: 21; a VH CDR3 comprising the amino acid sequence set forth in SEQ ID NO: 22; a VL CDR1 comprising the amino acid sequence set forth in SEQ ID NO: 26; a VL CDR2 comprising the amino acid sequence set forth in SEQ ID NO: 27; and a VL CDR3 comprising the amino acid sequence set forth in SEQ ID NO: 28.

In another aspect, the recombinant antibody comprises a first antigen-binding portion comprising one of: (A) scFV comprising the amino acid sequence set forth in SEQ ID NO: 54; or (B) a VH comprising the amino acid sequence set forth in SEQ ID NO: 50 and a VL comprising the amino acid sequences set forth in SEQ ID NO: 52; or (C) a VH CDR1 comprising the amino acid sequence set forth in SEQ ID NO: 38; a VH CDR2 comprising the amino acid sequence set forth in SEQ ID NO: 39; a VH CDR3 comprising the amino acid sequence set forth in SEQ ID NO: 40; a VL CDR1 comprising the amino acid sequence set forth in SEQ ID NO: 44; a VL CDR2 comprising the amino acid sequence set forth in SEQ ID NO: 45; and a VL CDR3 comprising the amino acid sequence set forth in SEQ ID NO: 46.

In another aspect, the recombinant antibody comprises a first antigen-binding portion comprising one of: (A) scFV comprising the amino acid sequence set forth in SEQ ID NO: 72; or (B) a VH comprising the amino acid sequence set forth in SEQ ID NO: 68 and a VL comprising the amino acid sequences set forth in SEQ ID NO: 70; or (C) a VH CDR1 comprising the amino acid sequence set forth in SEQ ID NO: 56; a VH CDR2 comprising the amino acid sequence set forth in SEQ ID NO: 57; a VH CDR3 comprising the amino acid sequence set forth in SEQ ID NO: 58; a VL CDR1 comprising the amino acid sequence set forth in SEQ ID NO: 62; a VL CDR2 comprising the amino acid sequence set forth in SEQ ID NO: 63; and a VL CDR3 comprising the amino acid sequence set forth in SEQ ID NO: 64.

In another aspect, the recombinant antibody comprises a first antigen-binding portion comprising one of: (A) scFV comprising the amino acid sequence set forth in SEQ ID NO: 90; or (B) a VH comprising the amino acid sequence set forth in SEQ ID NO: 86 and a VL comprising the amino acid sequences set forth in SEQ ID NO: 88; or (C) a VH CDR1 comprising the amino acid sequence set forth in SEQ ID NO: 74; a VH CDR2 comprising the amino acid sequence set forth in SEQ ID NO: 75; a VH CDR3 comprising the amino acid sequence set forth in SEQ ID NO: 76; a VL CDR1 comprising the amino acid sequence set forth in SEQ ID NO: 80; a VL CDR2 comprising the amino acid sequence set forth in SEQ ID NO: 81; and a VL CDR3 comprising the amino acid sequence set forth in SEQ ID NO: 82.

In another aspect, the recombinant antibody comprises a first antigen-binding portion comprising one of: (A) scFV comprising the amino acid sequence set forth in SEQ ID NO: 108; or (B) a VH comprising the amino acid sequence set forth in SEQ ID NO: 104 and a VL comprising the amino acid sequence set forth in SEQ ID NO: 106; or (C) a VH CDR1 comprising the amino acid sequence set forth in SEQ ID NO: 92; a VH CDR2 comprising the amino acid sequence set forth in SEQ ID NO: 93; a VH CDR3 comprising the amino acid sequence set forth in SEQ ID NO: 94; a VL CDR1 comprising the amino acid sequence set forth in SEQ ID NO: 98; a VL CDR2 comprising the amino acid sequence set forth in SEQ ID NO: 99; and a VL CDR3 comprising the amino acid sequence set forth in SEQ ID NO: 100.

In another aspect, the recombinant antibody comprises a first antigen-binding portion comprising one of: (A) scFV comprising the amino acid sequence set forth in SEQ ID NO: 132; or (B) a VH comprising the amino acid sequence set forth in SEQ ID NO: 128 and a VL comprising the amino acid sequence set forth in SEQ ID NO: 130; or (C) a VH CDR1 comprising the amino acid sequence set forth in SEQ ID NO: 116; a VH CDR2 comprising the amino acid sequence set forth in SEQ ID NO: 117; a VH CDR3 comprising the amino acid sequence set forth in SEQ ID NO: 118; a VL CDR1 comprising the amino acid sequence set forth in SEQ ID NO: 122; a VL CDR2 comprising the amino acid sequence set forth in SEQ ID NO: 123; and a VL CDR3 comprising the amino acid sequence set forth in SEQ ID NO: 124.

In one aspect, a recombinant antibody according to the present disclosure comprises a first antigen-binding portion comprising a heavy chain variable region comprising CDR1, CDR2, and CDR3 from a VH sequence and a light chain variable region comprising CDR1, CDR2, and CDR3 from a VL sequence in any of Tables 1-6 or 8. For example, in one aspect, a recombinant antibody according to the present disclosure comprises a heavy chain variable region comprising CDR1, CDR2, and CDR3 from SEQ ID NO: 50 and a light chain variable region comprising CDR1, CDR2, and CDR3 from SEQ ID NO: 52. In another aspect, a recombinant antibody according to the present disclosure comprises a first antigen-binding portion comprising a heavy chain variable region comprising CDR1, CDR2, and CDR3 from a VH sequence in any of Tables 1-6 or 8 that is at least 90% identical to that VH sequence and/or comprises a light chain variable region comprising CDR1, CDR2, and CDR3 from a VL sequence in that same Table that is at least 90% identical to that VL sequence. For example, in one aspect, a recombinant antibody according to the present disclosure comprises a heavy chain variable region comprising CDR1, CDR2, and CDR3 from SEQ ID NO: 50 that is at least 90% identical to SEQ ID NO: 50 and/or comprises a light chain variable region comprising CDR1, CDR2, and CDR3 from SEQ ID NO: 52 that is at least 90% identical to SEQ ID NO: 52.

In another aspect, a recombinant antibody according to the present disclosure comprises a second antigen-binding portion comprising a heavy chain variable region comprising CDR1, CDR2, and CDR3 from a VH sequence and a light chain variable region comprising CDR1, CDR2, and CDR3 from a VL sequence in Table 7 or Table 9. For example, in one aspect, a recombinant antibody according to the present disclosure comprises a heavy chain variable region comprising CDR1, CDR2, and CDR3 from SEQ ID NO: 112 and a light chain variable region comprising CDR1, CDR2, and CDR3 from SEQ ID NO: 111. In another aspect, a recombinant antibody according to the present disclosure comprises a first antigen-binding portion comprising a heavy chain variable region comprising CDR1, CDR2, and CDR3 from a VH sequence in Table 7 or Table 9 that is at least 90% identical to that VH sequence and/or comprises a light chain variable region comprising CDR1, CDR2, and CDR3 from a VL sequence in that same Table that is at least 90% identical to that VL sequence. For example, in one aspect, a recombinant antibody according to the present disclosure comprises a heavy chain variable region comprising CDR1, CDR2, and CDR3 from SEQ ID NO: 112 that is at least 90% identical to SEQ ID NO: 112 and/or comprises a light chain variable region comprising CDR1, CDR2, and CDR3 from SEQ ID NO: 111 that is at least 90% identical to SEQ ID NO: 111.

In one aspect, the first antigen-binding portion and/or second antigen-binding portion of a bi-specific antibody of the present disclosure are scFvs. In one aspect, the bi-specific antibody according to the present invention comprises a first antigen-binding portion comprising a scFV comprising the amino acid sequence set forth in SEQ ID NO: 18, 36, 54, 72, 90, 108 or 132 and/or a second antigen-binding portion comprising a scFV comprising the amino acid sequence set forth in SEQ ID NO: 113. In another aspect, a bi-specific antibody according to the present invention comprises a first antigen-binding portion comprising the six CDRs (VH CDR1, CDR2, and CDR3 and VL CDR1, CDR2, and CDR3) from the amino acid sequence set forth in SEQ ID NO: 18, 36, 54, 72, 90, 108 or 132 and is at least 90% identical to that scFV sequence and/or comprises a second antigen-binding portion comprising the six CDRs (VH CDR1, CDR2, and CDR3 and VL CDR1, CDR2, and CDR3) from the amino acid sequence set forth in SEQ ID NO: 113 and is at least 90% identical to that scFV sequence.

In one aspect, the first antigen-binding portion of a recombinant bi-specific antibody of the present disclosure specifically binds to WT1 HLA and the second antigen-binding portion specifically binds to an antigen on the surface of an immune effector cell. In another aspect, the immune effector cell is selected from the group consisting of natural killer (NK) cells, macrophages, T cells, and combinations thereof. In another aspect, the immune effector cell is a CD3+ cell. In a further aspect, the recombinant antibody specifically binds to CD3. In one aspect, the recombinant antibody binds to a WT1-HLA2+ cell, for example, a WT1/HLA2+ cell having a low density of WT1/HLA2 on its surface.

In one aspect, the invention provides a nucleic acid that encodes a recombinant antibody described herein. In a related aspect, a host cell is transformed with an expression vector comprising a nucleic acid of the present disclosure. In one aspect, the nucleic acid comprises a DNA sequence set forth in any of Tables 1-9.

In another aspect, the present disclosure provides a pharmaceutical composition comprising a recombinant bi-specific antibody described herein and a physiologically acceptable diluent, excipient, or carrier. Optionally, the composition additionally comprises one or more physiologically active agents, for example, an anti-cancer agent, an adjuvant or other immune-stimulating substance, an anti-angiogenic substance, an analgesic substance, etc. In various particular embodiments, the composition comprises one, two, three, four, five, or six physiologically active agents in addition to a recombinant bi-specific antibody.

In one aspect, a pharmaceutical composition of the present disclosure comprises a recombinant antibody described herein with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrin, a chelating agent such as EDTA, glutathione, a stabilizer, and an excipient. Neutral buffered saline or saline mixed with serum albumin are examples of appropriate diluents. In accordance with appropriate industry standards, preservatives such as benzyl alcohol may also be added. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile. In one aspect, the composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, 16th Ed. (1980) and 20th Ed. (2000), Mack Publishing Company, Easton, Pa.

As is understood in the art, pharmaceutical compositions comprising the bi-specific antibodies of the present disclosure are administered to a subject in a manner appropriate to the indication. A pharmaceutical composition of the present disclosure comprising a recombinant antibody described herein may be formulated for delivery by any route that provides an effective dose of the bi-specific antibody. Pharmaceutical compositions may be administered by any suitable technique, including but not limited to parenterally, topically, or by inhalation. If injected, the pharmaceutical composition can be administered, for example, via intraarticular, intravenous, intramuscular, intralesional, intraperitoneal or subcutaneous routes, by bolus injection, or continuous infusion. Localized administration, e.g. at a tumor site is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including tablets, capsules, syrups, lozenges or chewing gum; and topical preparations such as lotions, gels, sprays, patches, and ointments.

In one aspect, the present disclosure provides a method of killing a WT1-positive cell comprising contacting the cell with a recombinant bi-specific antibody described herein and an immune effector cell. The present disclosure also provides a method of treatment of a subject having a WT1-positive disease comprising administering to the subject a therapeutically effective amount of a recombinant bi-specific antibody described herein. In one aspect, the method further comprises administering to the subject an immune effector cell. In one aspect, the immune effector cell is a cytotoxic cell, for example, a natural killer cell, macrophage, or T cell. In one aspect, the cytotoxic T cells is a CD3+ cytotoxic T cell, optionally, an autologous T cell. In one aspect, the WT1 positive disease is leukemia (chronic or acute) or a WT1-positive cancer. Examples of WT1 positive cancers include, but are not limited to, chronic myelocytic leukemia, multiple myeloma (MM), acute lymphoblastic leukemia (ALL), acute myeloid/myelogenous leukemia (AML), myelodysplastic syndrome (MDS), mesothelioma, ovarian cancer, gastrointestinal cancers, breast cancer, prostate cancer and glioblastoma.

The present disclosure thus provides a method of treating a cancer comprising administering a therapeutically effective amount of a recombinant antibody or composition described herein to a patient in need thereof. In one aspect, the cancer is selected from the group consisting of adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colon cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, Ewing's sarcoma, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell carcinoma, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms tumor.

In another aspect, the invention provides a method of stimulating a primary T cell response and a secondary T cell response in a subject comprising administering a composition comprising a recombinant antibody, said recombinant antibody comprising a first antigen-binding portion and second antigen-binding portion, wherein said first antigen-binding portion specifically binds to a first tumor antigen and said second antigen-binding portion specifically binds to an immune effector cell surface antigen, wherein the primary T cell response comprises stimulating cytotoxic T cells against the first tumor antigen, and wherein the secondary T cell response comprises stimulating effector T cells and/or memory T cells against the first tumor antigen and/or against a second tumor antigen. In one aspect, the first tumor antigen is WT1-HLA and the second tumor antigen is a non WT1/RMF tumor antigen. Examples of non-WT1/RMF tumor antigens include, but are not limited to, HER2-neu, mesothelin, Tert, Muc 16, Muc1, PSMA, and others known in the art (Cheever et al. *Clinical cancer research: an official journal of the American Association for Cancer Research.* 2009; 15(17):5323-37). In one aspect, the primary T cell response and/or the secondary T cell response comprises an increase in T cells at a tumor site, for example, bone marrow, lung, liver, brain, genitourinary tract, gastrointestinal tract and/or spleen.

In one aspect, the secondary T cell response comprises stimulating effector T cells and/or memory T cells against the first tumor antigen and a second tumor antigen. In another aspect, the secondary T cell response comprises stimulating effector T cells against the second tumor antigen and not against the first tumor antigen. In one aspect, the secondary T cell response does not require antigen-presenting cells (i.e., cross-presentation) or co-stimulatory molecules such as CD86 or inducible costimulator ligand (ICOSL). In another aspect, the secondary T cell response comprises an increase in CD8 T cells. In a related aspect, the secondary T cell response is long-lived, e.g., lasting for more than one week, more than two weeks, more than three weeks, more than one month, or more than two months. In one aspect, the secondary T cell response comprises T cells that were previously anergic.

In one aspect, a method of stimulating a primary T cell response and a secondary T cell response according to the present disclosure comprises administering a composition comprising a recombinant bi-specific antibody described herein, for example, a recombinant bi-specific antibody comprising the amino acid sequence set forth in SEQ ID NO: 110. In another aspect, the method comprises administering a bi-specific antibody comprising a first antigen binding portion that specifically binds to WT1/HLA and the secondary T cell response comprises T cells previously activated with a non-WT1-RMF antigen.

In one aspect, the primary T cell response and/or secondary T cell response occurs in vivo. For example, a bi-specific antibody described herein can be administered to a patient in need thereof in an amount effective to stimulate a primary T cell response against WT1/HLA and a secondary T cell response against a non-WT1-RMF tumor antigen. In another aspect, the primary T cell response and/or secondary T cell response occurs ex vivo. For example, a bi-specific antibody according to the present disclosure can be administered to cells in vitro to activate and expand a population of T cells having specificity for a tumor antigen, e.g., a non-WT1-RMF tumor antigen. A therapeutically effective amount of the T cells can then be administered to a subject in need thereof in, e.g., autologously, to treat cancer.

Without intending to be bound by theory, the primary T cell and/or secondary T cell response may result from the ability of the bi-specific antibody to bring a TCR of a T cell close enough to a tumor cell to recognize additional MHC/peptide epitopes directly on the tumor. In one aspect, the binding of the first antigen binding portion of the bi-specific antibody to a first tumor antigen, e.g., WT1/HLA, during the T cell stimulation phase can block recognition of the first tumor antigen from the cognate TCR of the T cells, thereby resulting in a secondary T cell response specific for a tumor antigen other than the first tumor antigen.

The present disclosure therefore provides a method of producing effector T cells and/or memory T cells against a tumor antigen comprising activating a T cell with the recombinant antibody described herein. In one aspect, said T cells produced following activation are viable for an extended period of time, e.g., at least one week, at least two weeks, at least three weeks, at least one month, or at least two months. In one aspect, the recombinant antibody comprises a first antigen binding portion that binds to WT1/HLA, but the effector T cells and/or memory T cells produced are against a non-WT1-RMF tumor antigen, for example, HER2-neu, mesothelin, Tert, Muc 16, Muc1, PSMA, and others known in the art. In one aspect, the effector T cells and/or memory T cells are produced in vivo. In another aspect, the effector T cells and/or memory T cells are produced ex vivo, for example, for use in adoptive T cell therapy. In one aspect, administering a bi-specific antibody increases production of CD8 T cells, resulting in long-lived effector memory. The bi-specific antibodies according to the present disclosure having a first binding portion specific for WT1/HLA are therefore capable of inducing a vaccinal response against non-WT1 tumor antigens, resulting in broad and effective anti-tumor therapy.

The methods of treatment of the present disclosure encompass alleviation or prevention of at least one symptom or other aspect of a disorder, or reduction of disease severity, and the like. In one aspect, a therapeutically effective amount of a recombinant bi-specific antibody or pharmaceutical composition of the invention is an amount effective to inhibit growth of WT1-positive cells, reduce tumor size/burden, prevent tumor cell metastasis/infiltration, and/or result in cell death, e.g., via apoptosis or necrosis. In another aspect, a method comprising administering a bi-specific antibody prophylactically, e.g., to induce a secondary T cell response and produce memory T cells, is effective to prevent onset or recurrence or reduce the severity of a disease. A bi-specific antibody or pharmaceutical composition described herein need not effect a complete cure, or eradicate every symptom or manifestation of a disease, to constitute a viable therapeutic agent. As is recognized in the art, therapeutic agents may reduce the severity of a given disease state, but need not abolish every manifestation of the disease to be regarded as useful. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient.

Dosages and the frequency of administration for use in the methods of the present disclosure may vary according to such factors as the route of administration, the particular bi-specific antibodies employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

A recombinant bi-specific antibody of the present disclosure may be administered, for example, once or more than once, e.g., at regular intervals over a period of time. In general, the recombinant antibody or pharmaceutical composition is administered to a subject until the subject manifests a medically relevant degree of improvement over baseline for the chosen indicator or indicators.

In general, the amount of a recombinant bi-specific antibody described herein present in a dose, or produced in situ by an encoding polynucleotide present in a dose, ranges from about 10 μg per kg to about 20 mg per kg of host. The use of the minimum dosage that is sufficient to provide effective therapy is usually preferred. Patients may generally be monitored for therapeutic or prophylactic effectiveness using assays suitable for the condition being treated or prevented; assays will be familiar to those having ordinary skill in the art and some are described herein.

The methods disclosed herein may include oral administration of bi-specific antibody described herein or delivery by injection of a liquid pharmaceutical composition. When administered in a liquid form, suitable dose sizes will vary with the size of the subject, but will typically range from about 1 ml to about 500 ml (comprising from about 0.01 μg to about 1000 μg per kg) for a 10-60 kg subject. Optimal doses may generally be determined using experimental models and/or clinical trials. The optimal dose may depend upon the body mass, body area, weight, or blood volume of the subject. As described herein, the appropriate dose may also depend upon the patient's condition, that is, stage of the disease, general health status, age, gender, weight, and other factors familiar to a person skilled in the medical art.

In particular embodiments of the methods described herein, the subject is a human or non-human animal. A subject in need of the treatments described herein may exhibit symptoms or sequelae of a disease, disorder, or condition described herein or may be at risk of developing the disease, disorder, or condition. Non-human animals that may be treated include mammals, for example, non-human primates (e.g., monkey, chimpanzee, gorilla), rodents (e.g., rats, mice, gerbils, hamsters, ferrets, rabbits), lagomorphs, swine (e.g., pig, miniature pig), equine, canine, feline, bovine, and other domestic farm and zoo animals.

The present disclosure will be more readily understood by reference to the following Example, which is provided by way of illustration and are not intended to be limiting.

EXAMPLE

Materials and Methods

Cell Samples, Cell Lines and Antibodies.

Peripheral blood mononuclear cells (PBMCs) from HLA-typed healthy donors and patients were obtained by Ficoll density centrifugation. The sources for obtaining human leukemia and solid tumor cell lines were described previously (Dao et al., supra). The cell lines for this study included: AML lines HL60, SET-2, Ph+ ALL line BV173, mesothelioma cell lines JMN and MSTO. All cells were HLA typed. The cell lines were cultured in RPMI 1640 supplemented with 5% FCS, penicillin, streptomycin, 2 mmol/L glutamine, and 2-mercaptoethanol at 37 C/5% $CO_2$. Tumor cells for all animal studies were transduced with GFP/luciferase as described previously (Dao et al., supra). ESK1 and its control human IgG1 were produced by Eureka Therapeutics Inc (Emeryville, Calif.) and APC conjugation was done according to the instructions of the manufacture (Dao et al., supra). Monoclonal antibody (mAb) against human HLA-A2 (clone BB7.2) conjugated to FITC or APC, and its isotype control mouse IgG2b/FITC or APC were purchased from BD Biosciences (San Diego, Calif.). Mouse anti-His tag mAb conjugated to FITC or PE and ELISA kits for human IFN-γ were purchased from Invitrogen, (NY). Renilla luciferase substrate ViviRen™ was purchased from Promega (Madison, Wis.).

Peptides.

All peptides were purchased and synthesized by Genemed Synthesis, Inc. (San Antonio, Tex.). Amino acid sequences for HER2-neu-369-377: KIFGSLAFL (SEQ ID NO: 138); p53 264-272: LFEVRVCAC (SEQ ID NO: 139); WT1: RMFPNAPYL (SEQ ID NO: 1); Prame-300: ALYVD-SLFFL (SEQ ID NO: 140); p435: NLTHVLYPV (SEQ ID NO: 141). WT1-NQM, AILDF, LDF and total pooled peptides were previously described (Doubrovina et al. Blood. 2012 Aug. 23; 120(8):1633-46). Control HLA-A2-binding peptide was derived from Ewing's sarcoma: QLQNPSYDK (SEQ ID NO: 142).

Construction, Expression and Purification of ESK-Bi-Specific Antibody.

In one embodiment, an ESK1 bi-specific antibody is a single-chain bi-specific antibody comprising ESK1 scFv at the N-terminal end and an anti-human CD3ε scFv of a mouse monoclonal antibody at the C-terminal end (FIG. 10). The DNA fragments coding for the ESK1 scFv antibody and the anti-human CD3ε scFv antibody were synthesized by GeneArt (Invitrogen) and subcloned into Eureka's mammalian expression vector pGSN-Hyg using standard DNA technology. A hexahistidine (His) tag was inserted downstream of the ESK1 bi-specific antibody at the C-terminal end for antibody purification and detection.

Chinese hamster ovary (CHO) cells were transfected with the ESK1 bi-specific antibody expression vector and stable expression was achieved by standard drug selection with methionine sulfoximine (MSX), a glutamine synthetase (GS)-based method (Fan, et al. Biotechnology Bioengineering. 109 (4), 1007-1005 (2012)). CHO cell supernatants containing secreted ESK1-bi-specific antibody molecules were collected. ESK1 bi-specific antibody was purified using HisTrap HP column (GE healthcare) by FPLC AKTA system. Briefly, CHO cell culture was clarified and loaded onto the column with low imidazole concentration (20 mM), and then an isocratic high imidazole concentration elution buffer (500 mM) was used to elute the bound ESK1 bi-specific antibody protein. A negative control bi-specific antibody, was constructed from an irrelevant human IgG1 antibody (Cat#ET901, Eureka Therapeutics) replacing ESK1 scFv.

Flow Cytometry Analysis.

For ESK-bi-specific antibody staining, human T cells, tumor cells or cell lines were incubated with different concentrations of ESK-bi-specific antibody or control bi-specific antibody for 30 minutes on ice, washed, and incubated with secondary mAbs against His-Tag. HER2-neu expression on primary ovarian cancer cells was measured by staining the tumor cells with Trastuzumab, followed by secondary goat anti-human IgG. HLA-A2 expression and ESK binding was determined by direct staining of the cells with respective mAbs. Phenotype of PBMCs or T cells from patient samples were characterized by direct staining of the cells with mAbs for CD3, CD4, CD8, CD45 RA, CD45RO, CCR7, CD19 or CD33 conjugated to various florophores. Flow cytometry data were collected on a FACS Calibur (Becton Dickinson) and analyzed with FlowJo V8.7.1 and 9.4.8 software.

Figure 8:
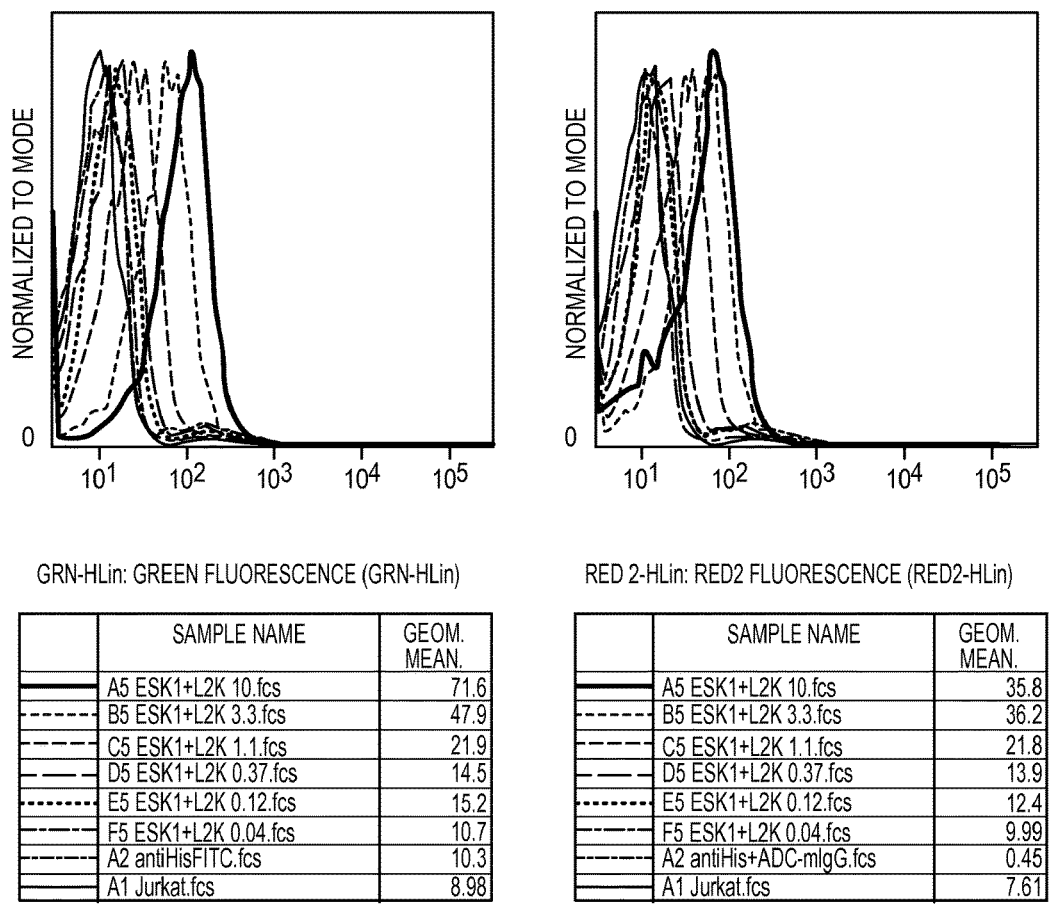
FIG. 8 shows the results of a FACS binding analysis comparing binding of ESK1-L2K bi-specific antibody with ET901+L2K bi-specific antibody and ET901+OKT3 bi-specific antibody.
Figure 11A:
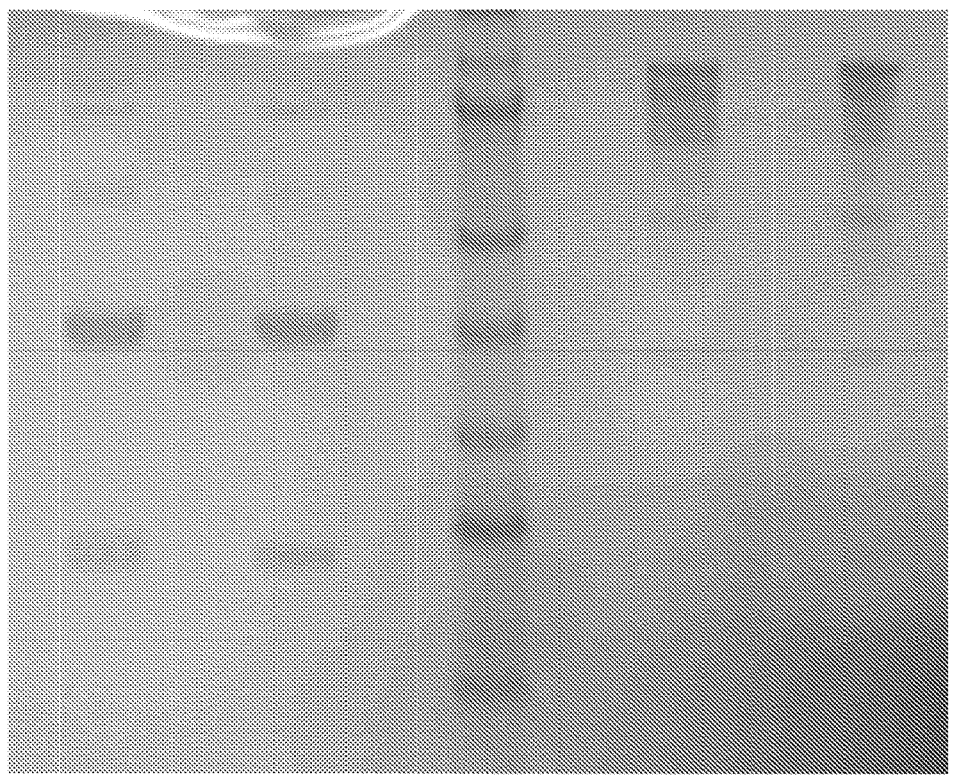
FIG. 11A is a PAGE of 1) ESK1/OKT3 (2 µg, reduced); 2) 901/OKT3 (2 µg, reduced); 3) SeeBlue Plus Pre-Stained Standard; 4) ESK1/OKT3 (2 µg, non-reduced); 5) 901/OKT3 (2 µg, non-reduced). 11B shows the standards.
Figure 11B:
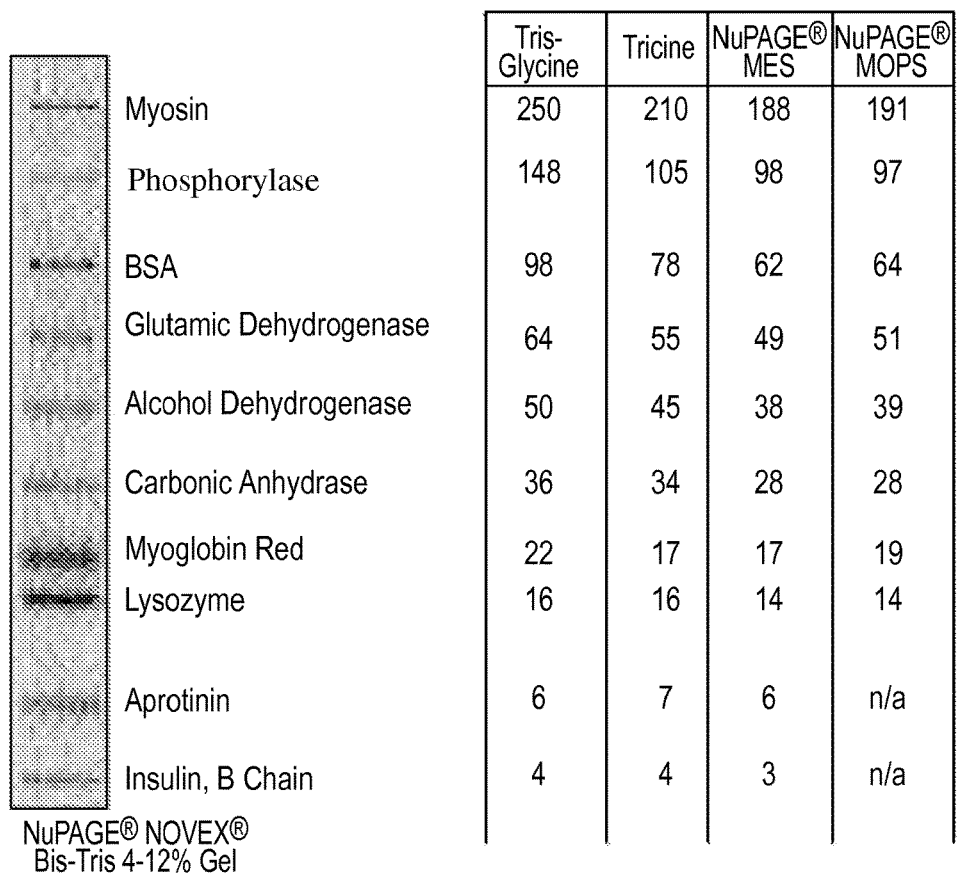
Figure 12:
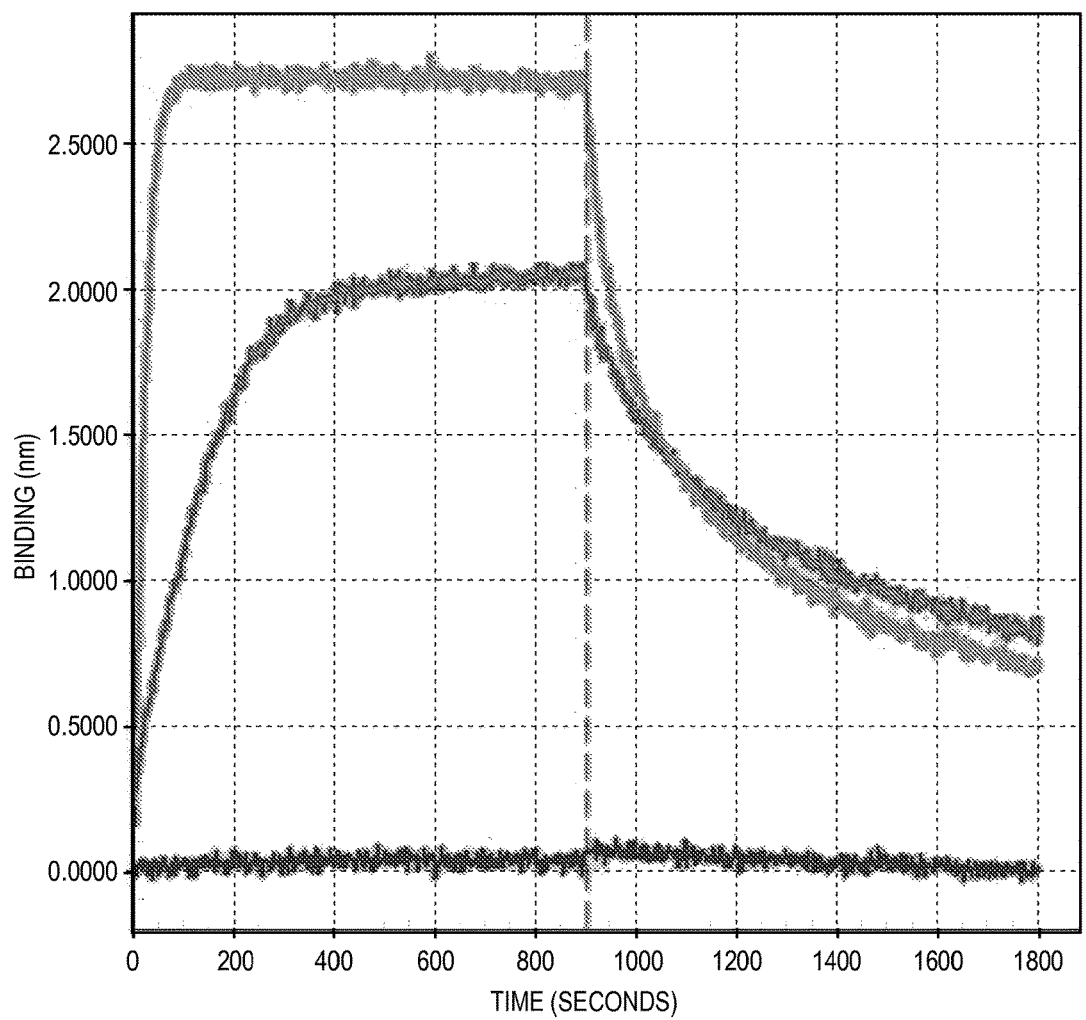
FIG. 12 shows the association and disassociation of ESK1 bi-specific monoclonal antibody against WT1/HLA-A2 complex.
Figure 13A:
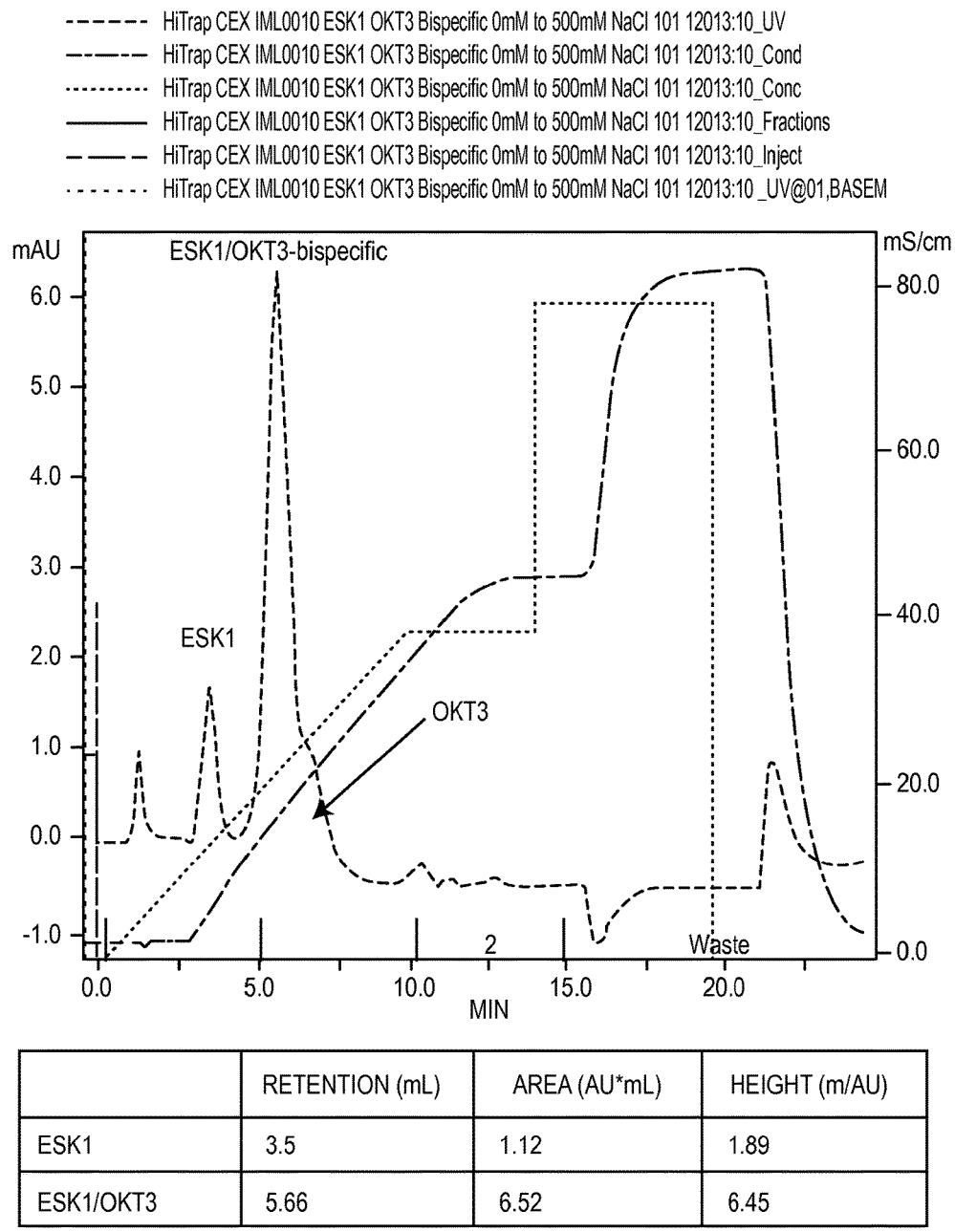
FIG. 13 shows the results of purification by cation exchange chromatography of ESK1/OKT3 bi-specific monoclonal antibody (13A) and a mixture of ESK1 and OKT3 (13B).
Figure 13B:
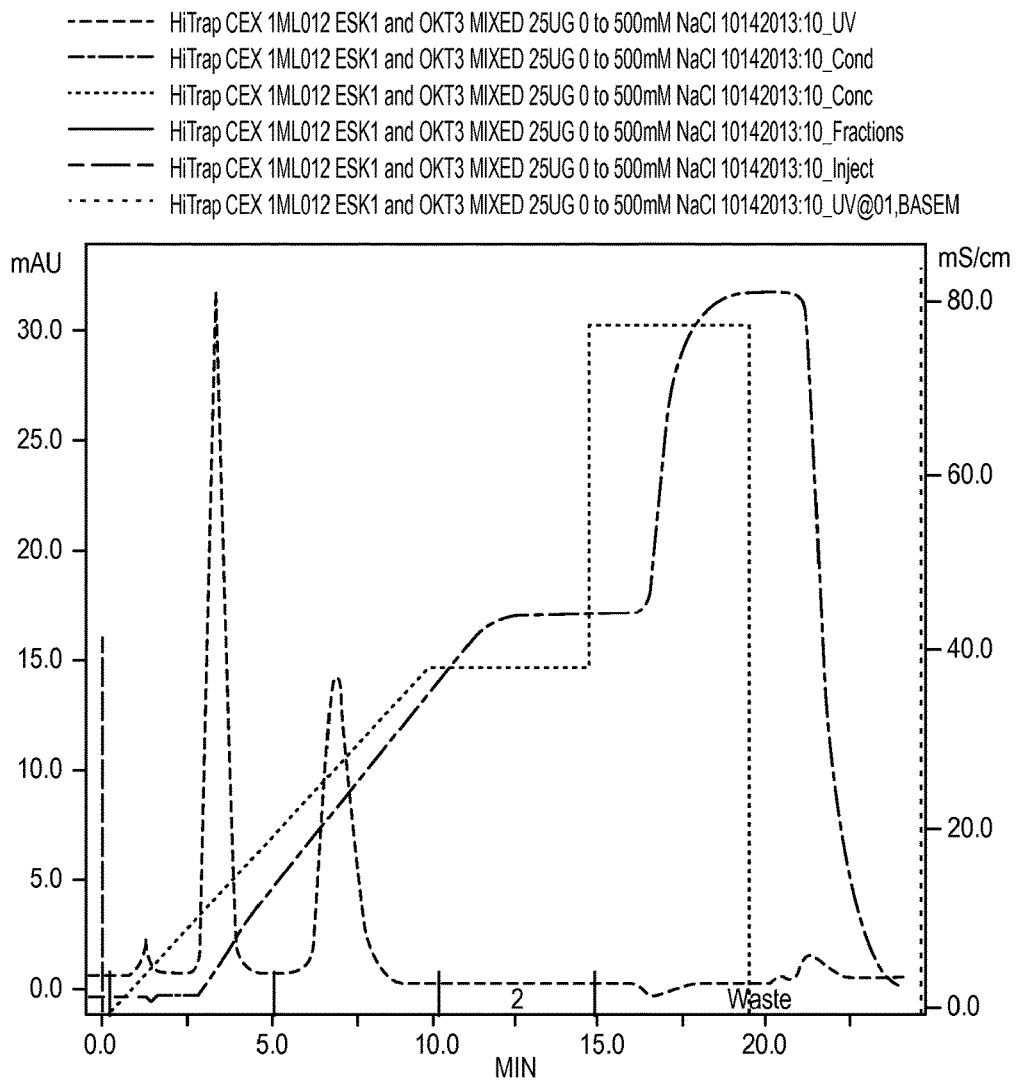
Figure 14A:
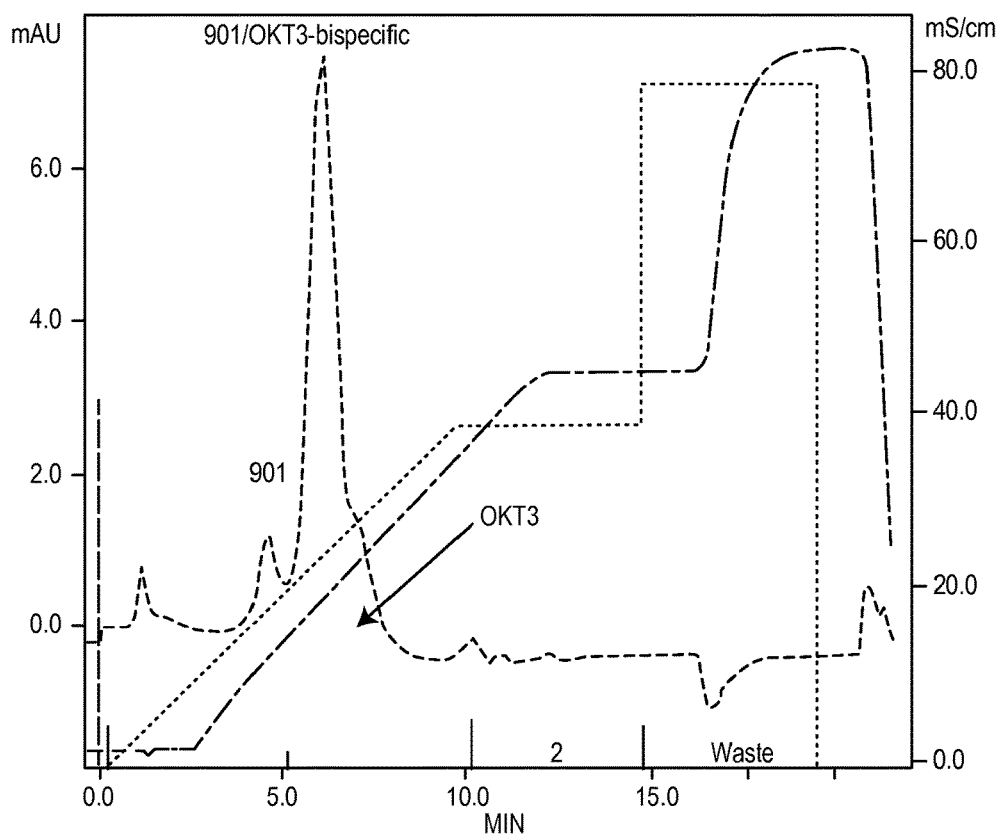
FIG. 14 shows the results of purification by cation exchange chromatography of ET901/OKT3 bi-specific monoclonal antibody (14A) and a mixture of 901 and OKT3 (14B).
Figure 14B:
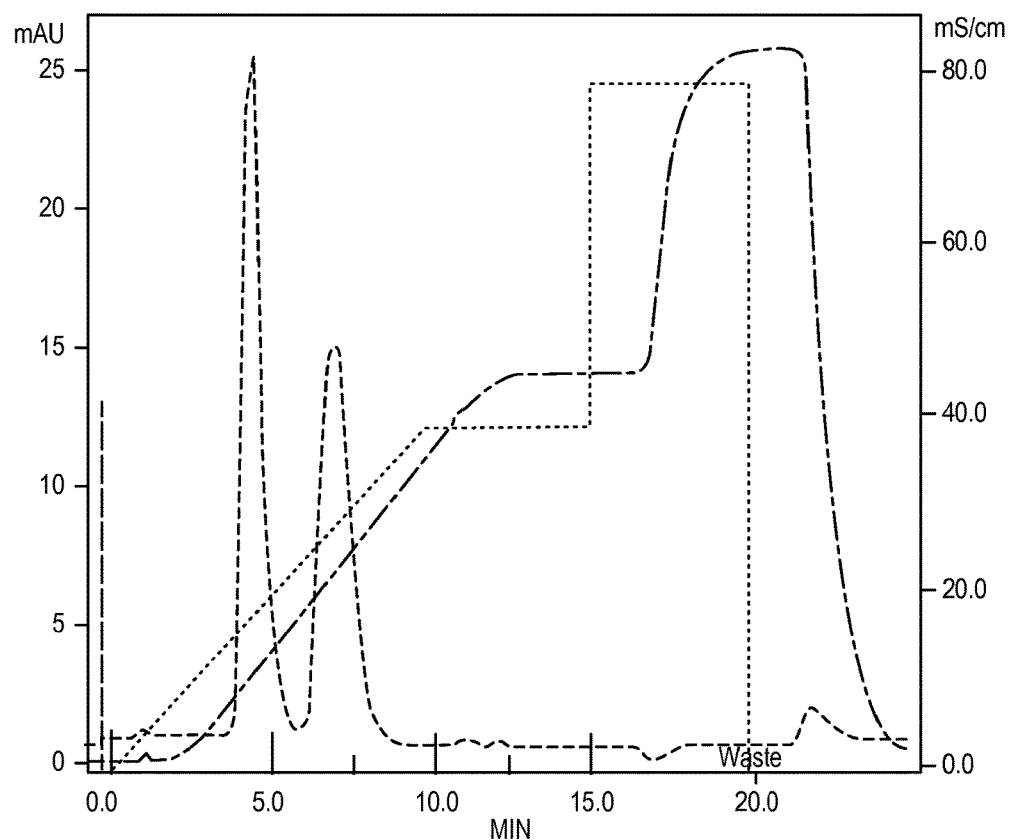
Figure 15:
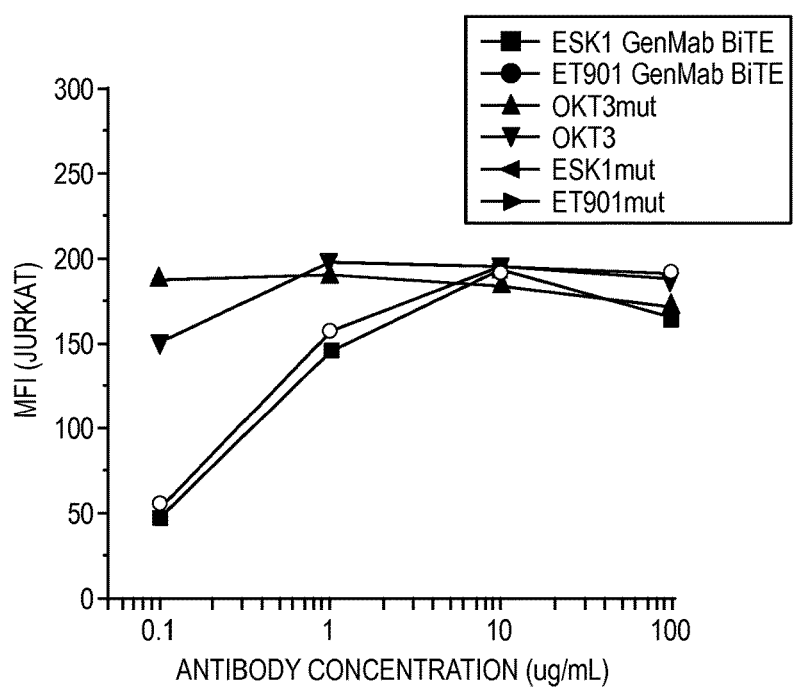
FIG. 15 shows binding towards CD3-positive Jurkat cells by FACS.
Figure 16A:
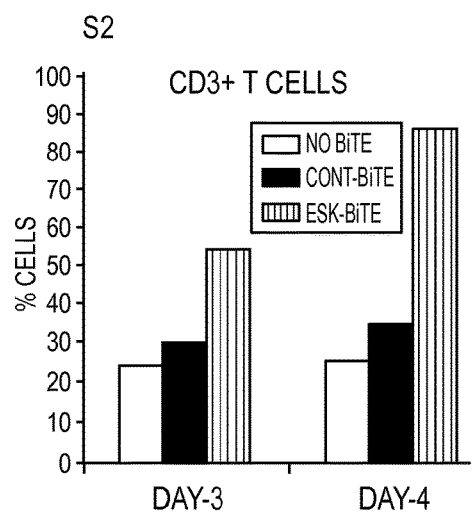
FIG. 16 shows ESK-bi-specific antibodies induce T cell activation in autologous settings. PBMCs from a HLA-A2+ patient with AML (before relapse) were co-cultured with purified autologous CD33+ myeloid blasts (after relapse) in the presence or absence of ESK or control-bi-specific antibody at 20 µg/ml and the cells were harvested and dual stained with CD33 for blasts (16B) and CD3 for T cells (16A) on day 3 and day 4, to assess the percentage of CD3 T cells and the blasts. Live cells from the CD3+ (16C) and CD33+ (16D) cultures were counted by trypan blue, and the absolute cell numbers were obtained by multiplying the percentage of each population times total cell numbers.
Figure 16B:
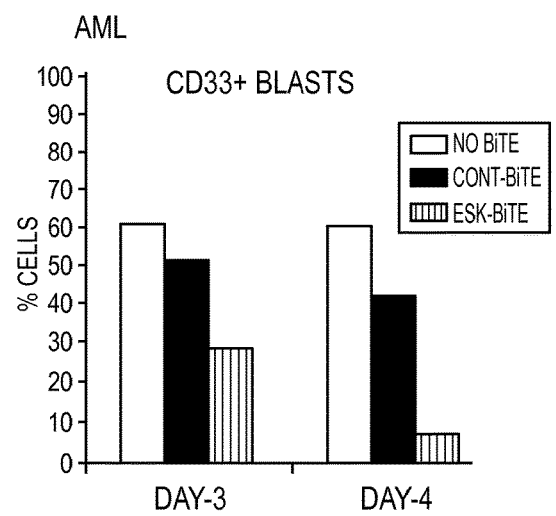
Figure 16C:
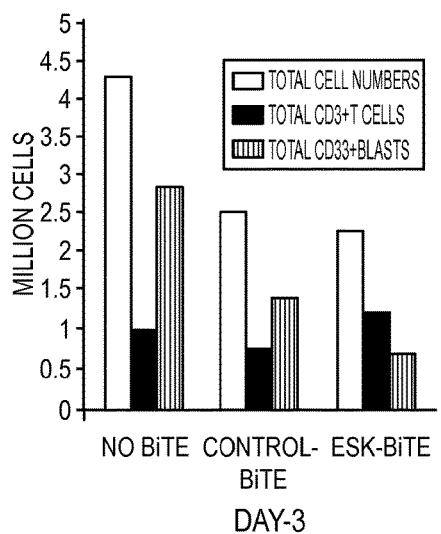
Figure 16D:
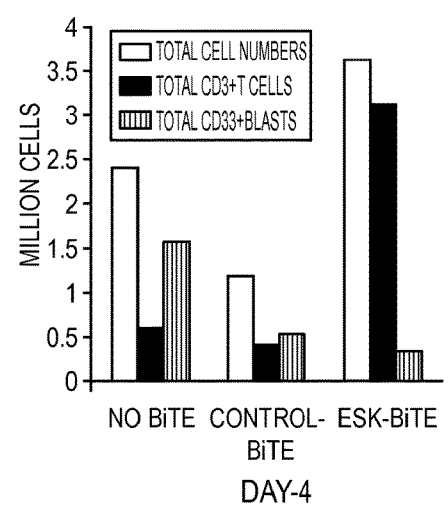

A binding study was performed to examine ESK1+L2K bi-specific antibody binding to Jurkat (a CD3$^+$ human cancer cell line) cells. Briefly, bi-specific antibody in 3× serial dilution, starting from 10 μg/mL was added to 0.5×10$^6$ Jurkat cells. The cells were incubated with FITC conjugated anti-His tag antibody (Thermo #MA1-81891) at a 100× dilution or mouse anti-His tag antibody with or without allophycocyanin (APC)-anti mouse IgG (Biolegend # Poly4053) at a 1000× dilution and analyzed by flow cytometry on a Guava EasyCyte 6HT (EMD Millipore). The results are shown in FIG. 8.

Next, using ESK1+L2K, ET901+L2K and ET901+OKT3 antibodies at 10 μg/mL, staining of Jurkat cells by FITC anti-His was examined. FITC ET901 and APC ET901 (ET901 is a fully human IgG1) was used as the control. The results are shown in FIG. 9.

A comparison of ESK1 and ESK1-bi-specific antibody binding to the MHC1/WT1 peptide complex was determined by ForteBio Octe analysis. The results are shown in the following table.

TABLE 10

| Protein | $k_d$ [1/s] | Error in $k_d$ | $k_a$ [1/Ms] | $K_D$ [nM] |
|---|---|---|---|---|
| ESK1 ScFv | 1.16E-3 | 1.54E-5 | 3.68E3 | 315 |
| ESK1 BITE | 7.04E-3 | 1.71E-4 | 1.98E4 | 355 |

Full Length ESK1-Bi-Specific Antibody:

In one embodiment, the ESK-1 bi-specific antibody is a full length antibody. Briefly, ESK1 or ET901 (negative control) and anti-CD3 (OKT3) were combined in equimolar ratios, yielding a final concentration of 0.8 mg/ml of each antibody within 0.5 ml. 12.5 μl of 1M 2-mercaptoethylamine (2-MEA) was added to the reaction mixture and the solution was incubated at 37° C. for 90 minutes. 2-MEA was removed by Zeba desalting columns (100-200 μl, 7-kDA, Pierce.) The solution was stored at 4° C. overnight to allow re-oxidation of the disulfide bonds. Production values are shown in Table 11.

TABLE 11

| Protein | Concentration (mg/ml) | Volume (ml) | Amount (mg) | Theoretic yield (mg) | Recovery rate |
|---|---|---|---|---|---|
| ESK1 | 1.33 | 0.5 | 0.67 | 0.8 | 84% |
| 901 | 1.29 | 0.5 | 0.64 | 0.8 | 80% |

Binding affinity was determined using ForteBio Octet QK. 5 μg/ml biotinylated MHC-WT1 was loaded onto the Streptavidin biosensor. After washing off excess antigen, ESK-1-OKT3, ESK1, and OKT3 solutions were tested at 20 μg/ml, 10 μg/ml and 10 μg/ml respectively for their association and dissociation constants. Binding parameters were calculated using 1:1 binding site model and are shown in Table 12.

TABLE 12

| Protein | $k_d$ [1/s] | Error in $k_d$ | $K_a$ [1/Ms] | $K_D$ [nM] |
|---|---|---|---|---|
| ESK1-OKT3 (bi-specific) | 3.30E-3 | 4.17E-5 | 3.58E4 | 92.2 |
| ESK1 | 4.99E-3 | 6.78E-5 | 5.47E5 | 9.12 |
| OKT3 | — | — | — | — |

ESK-Bi-Specific Antibody-Mediated T Cell Activation.

CD3 T cells were isolated from PBMCs by negative immunomagnetic cell separation using a pan T cell isolation kit (Miltenyi Biotec Inc., San Diego, Calif.). The ESK-bi-specific antibody or its control bi-specific antibody at various concentrations were incubated with target cells and purified CD3 T cells at different effector: target (E:T) ratio for overnight or different time periods. The supernatant fluids were harvested and cytokine release was measured by ELISA for IFN-γ and TNF-α. In addition, ESK-bi-specific antibody-mediated T cell activation in the presence of autologous tumor cells from a patient with ovarian cancer was evaluated by cell proliferation, measured by overnight 3H-Thymidine incorporation after seven days of co-incubation.

EBV-Specific T Cell Expansion and Reporter Gene Transduction.

T-cells were enriched from PBMCs by depletion of monocytes by adhesion. Non-adhering cells were stimulated with irradiated autologous EBV-transformed B cells (EBV-BLCLs) generated by transformation with the B95.8 strain of EBV at a 20:1 responder: stimulator (R:S) ratio and cultured in Yssel's medium, containing 5% HS(YHS; Gemini). Beginning on day 7, interleukin-2 (IL-2) at 10 to 30 units/mL was added to the T cell cultures every 2-3 days (Collaborative Biomedical Products, Bedford, Mass.), and were re-stimulated weekly with the same EBV-BLCLs at a 4:1 R:S ratio.

EBV specific T lymphocytes were transduced with retroviral vector tdrrsRLuc, expanded and enriched by sorting for PE, as previously described (Doubrovina, E. et al. *Blood* 119 (11), 2644-2655 (2012)). Transduced EBV specific T lymphocytes were cultured in G-rex flask (Wilson Wolf Manufacturing Corporation). For in vivo T cell tracing study, ten million cells were injected into mice and 4 hrs later, *Renilla* luciferase substrate ViviRen™ was given i.v.

ESK-Bi-Specific Antibody-Redirected T Cell Cytotoxicity.

The ESK-bi-specific antibody or its control bi-specific antibody at various concentrations were incubated with target cells and PBMCs, purified CD3 T cells or EBV-specific T cells at different effector: target (E:T) ratios for 5 hrs or overnight. The cytotoxicity was measured by $^{51}$Cr-release assay (after 5 hrs incubation) or LDH release assay (after overnight incubation) using Cytotox 96 non-radioreactive kit from Promega following their instruction. In one case of an AML patient, PBMCs and autologous blasts were co-incubated in the presence or absence of ESK or control-bi-specific antibody at 20 μg/ml and the cells were harvested and dual stained with CD33 for leukemia blasts and CD3 for T cells on day 3 and 4. For the case of an ovarian cancer patient, PBMCs were incubated with autologous ovarian cancer cells for a week and the cytotoxicity was measured by $^{51}$Cr-release assay.

Pharmacokinetic and Biodistribution Studies.

ESK-bi-specific antibody or control bi-specific antibody were labeled with $^{125}$I (PerkinElmer) using the chloramine-T method. One hundred (100) μg antibody was reacted with 1 mCi $^{125}$I and 20 µg chloramine-T, quenched with 200 µg Na metabisulfite, then separated from free $^{125}$I using a 10DG column equilibrated with 2% bovine serum albumin in PBS. Specific activity of the product was 6 mCi/mg. Radiolabeled bi-specific antibody (2 µg) was diluted with unlabeled bi-specific antibody to 20 µg per dose, and injected into mice retroorbitally. Blood was collected at various time points, weighed and measured on a gamma counter. At 24-hours, organs were harvested, weighed and measured for activity on a gamma counter.

Therapeutic Trials of the ESK-Bi-Specific Antibody in Human Tumor Xenograft NSG Models.

Human EBV-specific T cells were used for all xenograft models, as their antigenic specificity had been heavily biased towards EBV Ags, wherein they should not induce GVHD. For the BV173 ALL model, two million BV173 human leukemia cells were injected i.v. into NSG mice. On day 5, tumor engraftment was confirmed by firefly luciferase imaging in all mice that were to be treated; mice were then randomly divided into different treatment groups. On day 6, ten million of EBV-specific T cells were iv injected into mice. Four to 6 hours later, 20 µg ESK-bi-specific antibody or its control bi-specific antibody was i.v. injected and was repeated twice a week for total 6 times over the 3 weeks of treatment, along with i.v. injection of T cells once in a week times 2. For the SET-2 AML model, one million cells were i.v. injected into mice, the tumor engraftment was confirmed on day 3 by bioluminescence imaging, and mice were randomized into treatment groups. On day 4, ten million EBV-specific T cells were injected i.v. and 6 hrs later, 20 µg ESK-bi-specific antibody or its control bi-specific antibody was injected i.v. Over the treatment course, T cells were given twice a week and bi-specific antibodies were given every day for a total of 6 days. In the primary ALL model, five million ALL cells were injected i.v. into NSG mice. On day 6, tumor engraftment was confirmed by firefly luciferase imaging in all mice that were to be treated; mice were then randomly divided into different treatment groups. Thirty million EBV-specific T cells were injected i.v. into mice followed by injection i.v. of 20 µg ESK-bispecific antibody or its control bi-specific antibody. Bi-specific antibody injection was given daily, and T cells were given twice a week for a total of two weeks. For the JMN mesothelioma model, three hundred thousand tumor cells were mixed with six hundred thousand EBV-specific T cells and injected intraperitoneally (i.p.) and one hr later, 20 µg ESK-bi-specific antibody or control bi-specific antibody was i.v. injected into mice. The bi-specific antibodies were given every day for a total of 5 days. Tumor growth was monitored by firefly luciferase imaging at least twice a week, for all the animal models.

ESK-Bi-Specific Antibody Induced Secondary T Cell Response.

PBMCs, PBMCs depleted of NK cells and macrophages or purified CD3 T cells from a patient with ovarian cancer were cultured with irradiated (3000 rad) autologous ovarian cancer cells at an E: T ratio of 4-5:1, in the presence or absence of ESK-bi-specific antibody, or control-bi-specific antibody at 0.1 µg/ml, and presence of human IL-5 (5 ng/ml) and human IL-2 (10 µg/ml) in RPMI1640 medium supplemented with 10% autologous plasma (AP) for 6 days. On day 7, the cells were harvested and washed and used as effectors for IFN-g ELISPOT assay. In brief, HA-Multiscreen plates (Millipore) were coated with 100 µL of mouse anti-human IFN-g antibody (10 Ag/mL; clone 1-D1K; Mabtech) in PBS, incubated overnight at 4° C., washed with PBS to remove unbound antibody, and blocked with RPMI 1640/10% autologous plasma (AP) for 2 h at 37° C. Effectors cells were plated with either T2 cells (4:1 E: APC ratio) or irradiated autologous tumor cells or other tumor cell lines. Various test peptides were added to the wells at 20 µg/m L. Negative control wells contained APCs and T cells without peptides or with irrelevant peptides. Positive control wells contained T cells plus APCs plus 20 µg/mL phytohemagglutinin (PHA, Sigma). All conditions were done in triplicate. Microtiter plates were incubated for 20 h at 37° C. and then extensively washed with PBS/0.05% Tween and 100 µl/well biotinylated detection antibody against human IFN-g (2 µg/mL; clone 7-B6-1; Mabtech) was added. Plates were incubated for an additional 2 h at 37° C. and spot development was done as described (May et al. *Clinical cancer research: an official journal of the American Association for Cancer Research.* 2007; 13(15 Pt 1):4547-55.). Spot numbers were automatically determined with the use of a computer-assisted video image analyzer with KS ELISPOT 4.0 software (Carl Zeiss Vision).

The remaining T cells were expanded by adding fresh medium with IL-15 and IL-2 once a week, up to 7-8 weeks. In some cases, remaining T cells were re-stimulated with autologous tumor at an effector: target ratio of 9:1 for a week in the same conditions as for the first stimulation and T cell response was measured by IFN-g ELISPOT as described.

Results

Figure 1B:
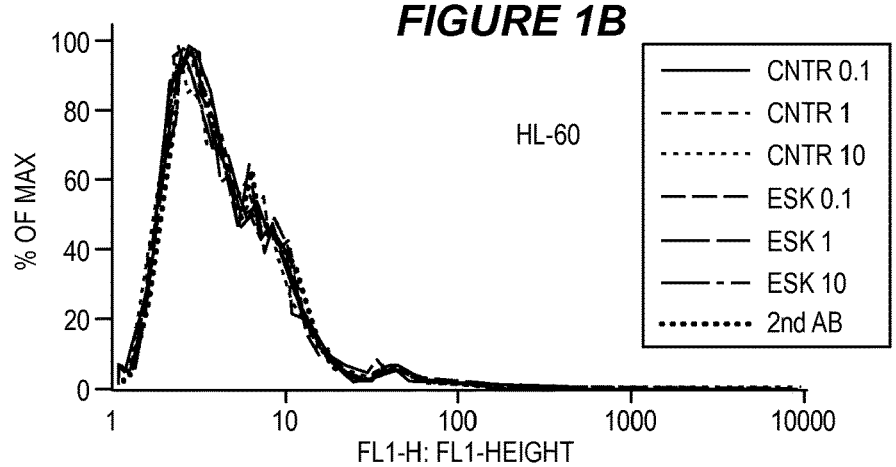
Figure 1C:
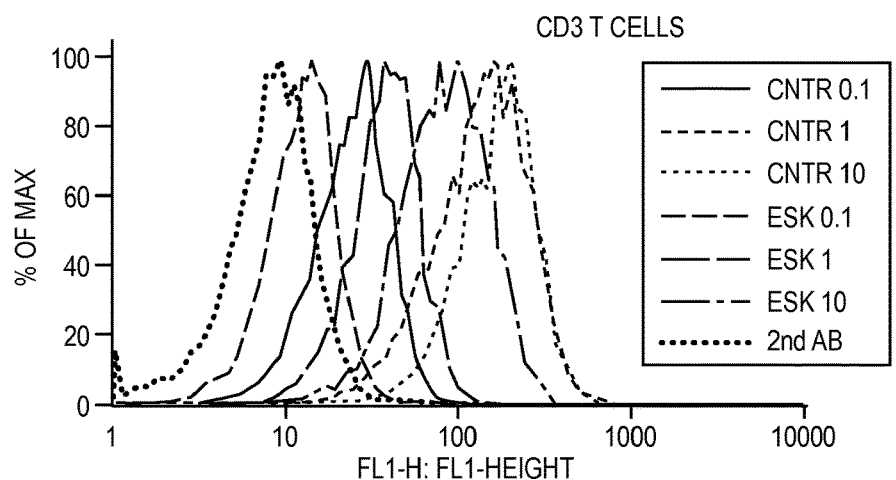

Selective binding to WT1+HLA-A0201+ tumor cells and T cells. Full length ESK1 mAb binds to a panel of leukemia cell lines and mesothelioma cell lines in a WT1 and HLA-A0201-restricted manner (Dao et al., supra). The binding specificity of the ESK-bi-specific antibody, a scFv construct, was tested. ForteBio Octet® (Menlo Park, Calif.) binding assay showed a Kd of 355 nM of the ESK-bi-specific antibody. ESK-bi-specific antibody bound to SET-2, a WT1 and HLA-A0201 double positive AML cell line, in a dose-dependent manner, even at a 0.1 µg/ml concentration, but did not bind to HL-60, a WT1positive, but HLA-A0201 negative, AML cell line (FIG. 1A, 1B). No positive binding of the control bi-specific antibody was seen to either SET-2 or HL-60 cells at all the concentrations tested, indicating the specificity of ESK-bi-specific antibody. Both bi-specific antibodies were able to bind to purified human CD3T cells, however (FIG. 1C). These results demonstrated bi-specificity in that the ESK-bi-specific antibody was able to selectively recognize the tumor cells expressing WT1 and HLA-A0201 and also human CD3 T cells.

T Cell Activation and Cytotoxicity Against WT1 and HLA-A0201 Positive Tumor Cells.

Figure 1D:
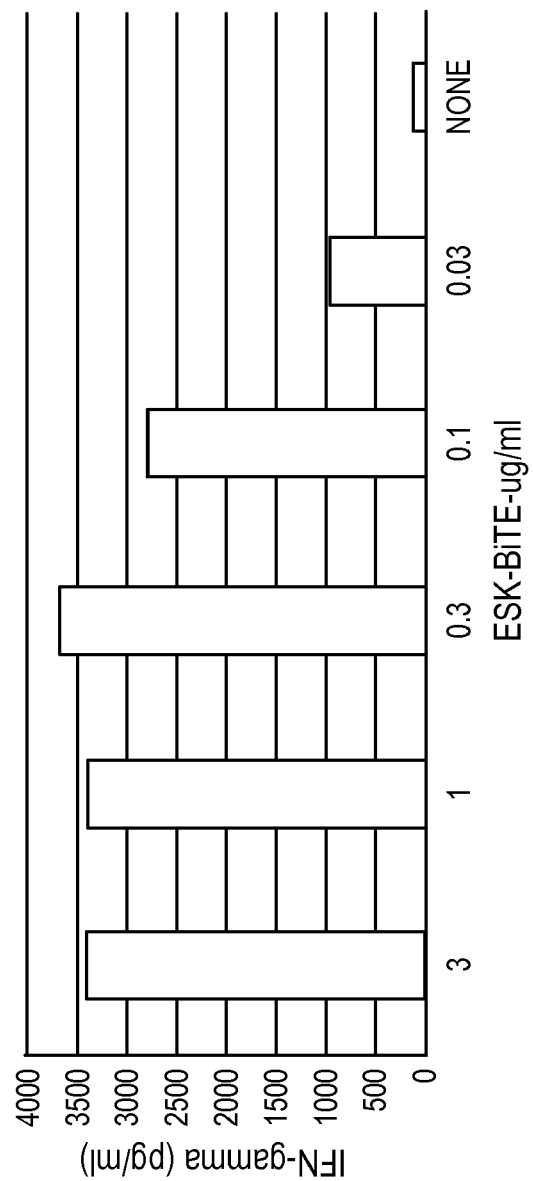

It has been shown that the activation of T cells by bi-specific antibody constructs depends on the proximal contact between T cells and target cells expressing the target antigens. This is crucial for avoiding unwanted inflammatory response caused by T cell activation, as one arm of the bi-specific antibody construct recognizes the invariant CD3 signaling complex. In the presence of ESK-bi-specific antibody and target SET-2 cells, a dose-dependent IFN-γ release was observed at indicated concentrations of ESK-bi-specific antibody (FIG. 1D). CD3 T cells alone or incubated with control-bi-specific antibody in the presence of SET-2 cells showed undetectable level of IFN-γ and their values were subtracted from the values of the ESK-bi-specific antibody group.

Figure 2C:
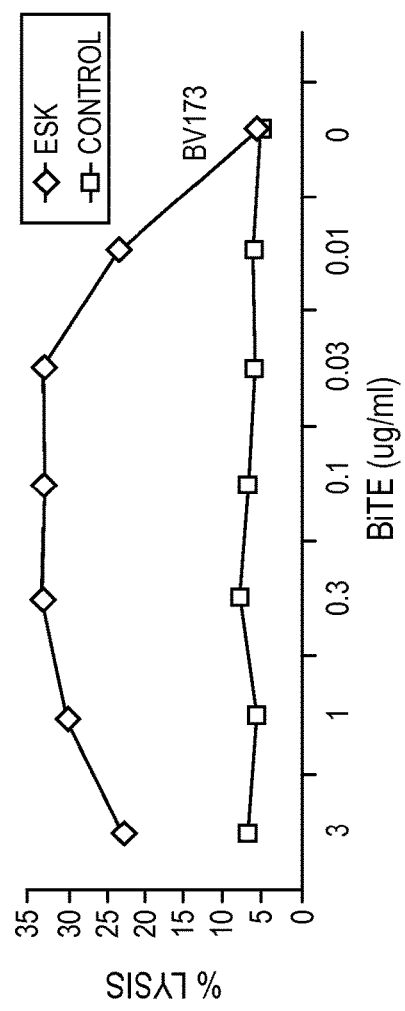
FIG. 2 shows that ESK-bi-specific antibody directs T cell cytotoxicity against WT1+/HLA-A0201+ tumor cells. Purified T cells were incubated with SET-2 (2A) or HL-60 cells (2B) at E:T ratio of 40:1, in the presence or absence of ESK or control bi-specific antibody at the indicated concentrations. T cell cytotoxicity was measured by $^{51}$Cr-release after 5-hour incubation. Similarly, ESK-directed cytotoxicity of PBMCs against BV173 (2C) and CML blasts (2D) from patient in a 6-hr-$^{51}$Cr release assay at an E:T ratio of 100:1. ESK-bi-specific antibody-mediated cytotoxicity by EBV-primed human T cells was measured by a 5 hour-$^{51}$Cr-release assay against BV173 (2E), JMN (2F) and primary ovarian cancer cells (2G) at the indicated E:T ratio. Bi-specific antibodies were used at 0.1 µg/ml. All the data points are average of triplicate cultures and represent one of two to three similar experiments.
Figure 2D:
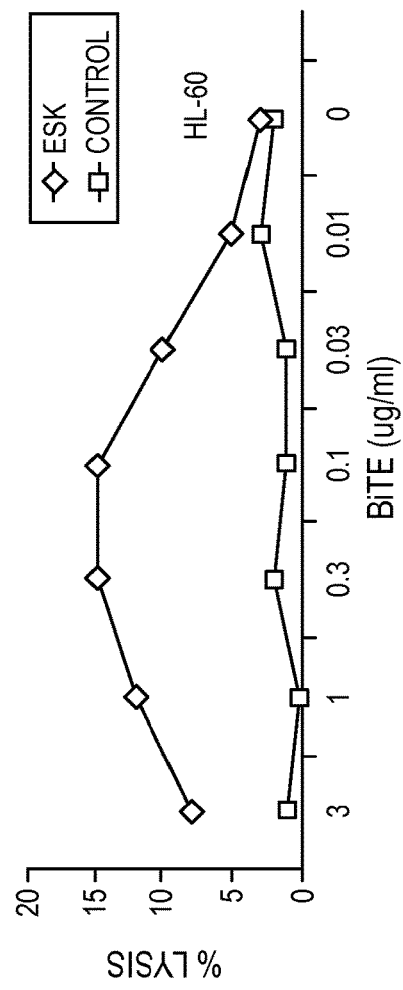

The potency of ESK-bi-specific antibody-directed T cell cytotoxicity against target cells that co-express WT1 and HLA-A0201 was assessed. Purified resting T cells were co-incubated with target cells with serially diluted ESK- or control bi-specific antibody for 5 hrs and cell lysis was measured by $^{51}$Cr-release. ESK-bi-specific antibody dose-dependently induced T cell cytotoxicity against AML cell line SET-2, but not HL-60, which was consistent with their binding specificity shown in FIG. 1 (FIG. 2A, 2B). When the co-incubation time was extended to 16 hrs, the target cell lysis was increased up to 90% and 80% at 3 µg/ml and 0.3 µg/ml of ESK-bi-specific antibody, respectively. Similarly, BV173 and primary CML blasts (WT1+/HLA-A0201+) were also lysed by PBMCs in the presence of ESK-bi-specific antibody in a dose-dependent manner in a 6 hr co-incubation (FIG. 2C, 2D), and the killing of BV173 was evident at 0.01 µg/ml of the ESK-bi-specific antibody. The relative weaker killing against the CML blasts might be due to a lower level expression of HLA-A2 and ESK-binding in this sample. Control bi-specific antibody did not induce any significant cytotoxicity, indicating that the target specificity is required for the T cell activation.

The ability of ESK-bi-specific antibody to redirect cytotoxicity of T cells that had previously been repeatedly primed with a different Ag, such as EBV, was addressed. Using such T cells could potentially avoid graft-versus-host disease (GVHD) in xenograft animal models, as the antigenic specificity of T cells should be heavily biased towards only EBV Ags. The potency of T cell killing by titration of the effector: target (E:T) ratios with ESK-bi-specific antibody at 0.1 µg/ml by 5 hr-51Cr release was tested. Potent dose-dependent killing was observed for ESK-bi-specific antibody against all the target cells tested (FIG. 2E, 2F, 2G). There was nearly 50% killing at higher E:T ratios and approximately 25% killing at an E:T ratio as low as 1.6:1 for BV173 (FIG. 2E). The specific killing was observed for JMN target cells, at an E: T ratio of 3.13 (FIG. 2F). Similarly, strong cytotoxicity against primary ovarian cancer cells was found ranging from more than 50% to 20% killing at the various E: T ratios (FIG. 2G). There was no killing in the cultures with T cells alone, or with control bi-specific antibody against WT1+/HLA-A0201+ in the mesothelioma cell line JMN, ALL BV173, and the primary ovarian cancer cells (all co-express WT1 and HLA-A0201). These results demonstrated that ESK-bi-specific antibody can specifically redirect potent cytotoxicity of previously activated T cells with a specificity other than to WT1, to lyse tumor cells that are WT1 and HLA-A0201 positive.

Figure 3A:
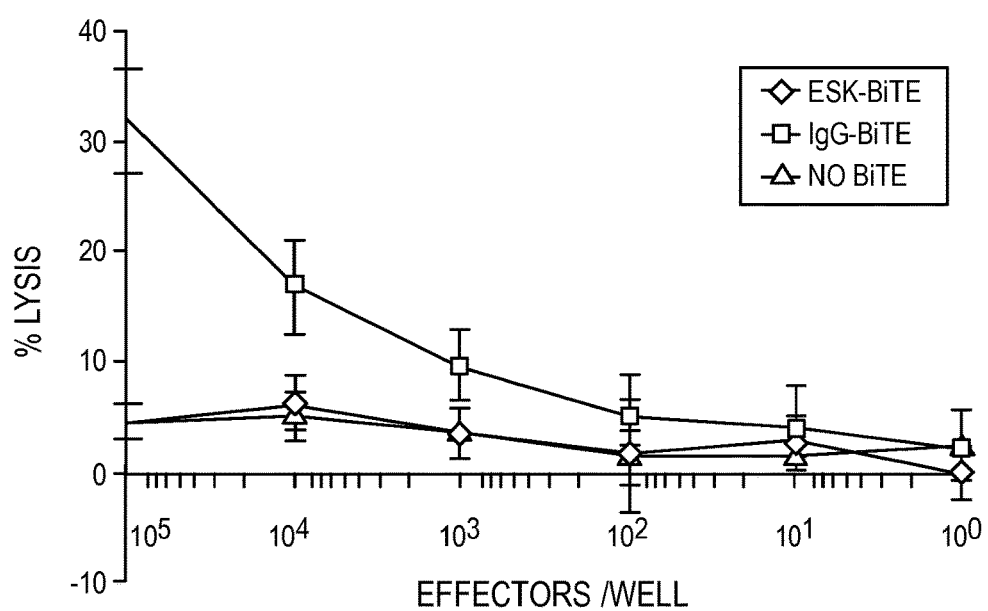
FIG. 3 shows that ESK-bi-specific antibody induces T cell activation in the presence of autologous ovarian cancer cells. PBMCs from a patient at indicated numbers/well were incubated with autologous irradiated ovarian cancer cells, in the presence of 0.1 µg/ml of ESK or control bi-specific antibody for the first 3 days. (3A) Cells were cultured for a total of 7 days and on day 8, $^{51}$Cr-labeled autologous tumor cells were added to the effector cells at a thousand cells/well. The $^{51}$Cr-release was measured 6 hrs later. (3B) PBMCs, autologous ovarian cancer cells, or PBMCs plus ovarian cancer cells were incubated with or without ESK or control bi-specific antibody at 0.1 µg/ml for 7 days. $^{3}$H-Thymidine was added overnight, and the cells were harvested the following day. The data represent triplicate cultures.
Figure 3B:
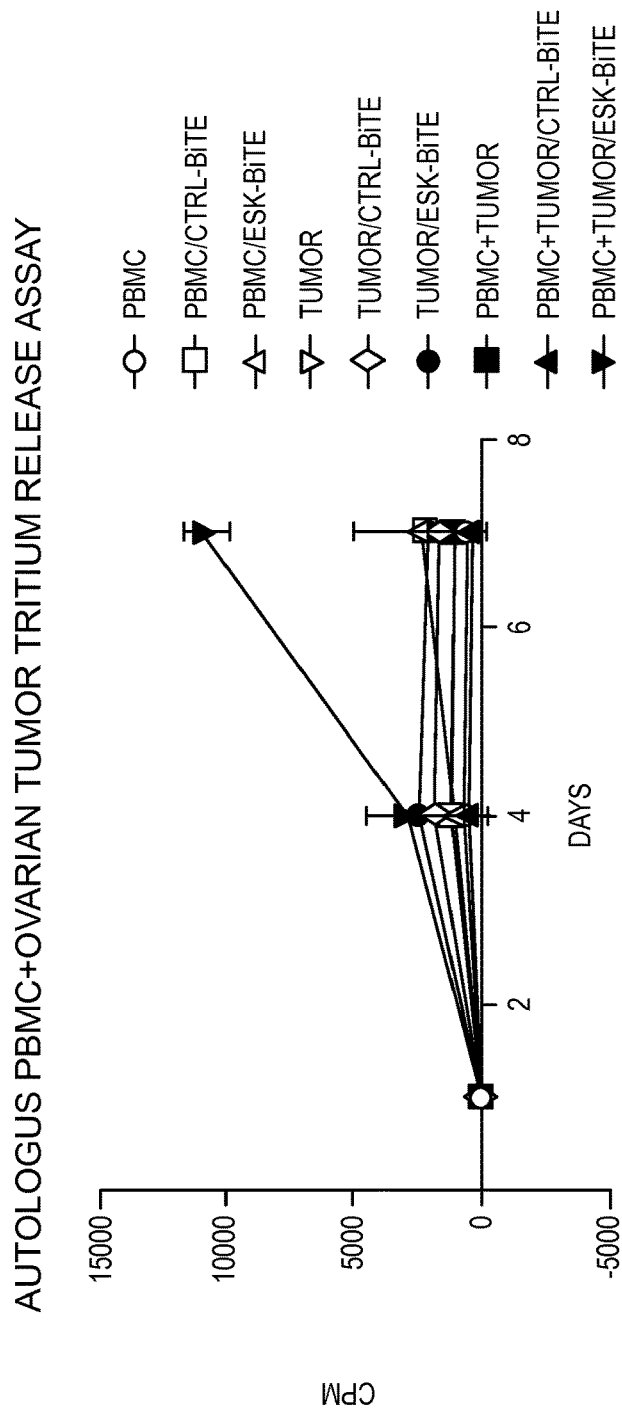

Next, the ESK-bi-specific antibody-mediated activation and cytotoxicity of T cells in an autologous setting was investigated more closely, mimicking the human in vivo situation. PBMCs from a patient with ovarian cancer were stimulated with irradiated autologous tumor cells at various E:T ratios as indicated, in the presence of 0.1 µg/ml of ESK-bi-specific antibody for 7 days. The cytotoxicity was measured by adding $^{51}$Cr-labeled autologous tumor cells in a 6 hr-culture on day 8. Dose-dependent killing was observed in the cultures with ESK-bi-specific antibody, even at 100 PBMCs at the start of the stimulation (FIG. 3A). No killing was observed in all the control groups. In parallel, T cell proliferation was measured by 3H-thymidine incorporation at the end of eight day culture (FIG. 3B). Significant cell proliferation was seen in only the cultures with ESK-bi-specific antibody. None of the PBMCs, nor the tumor cells alone responded to either ESK- or control-bi-specific antibody. In addition, co-cultures of PBMCs with autologous tumor cells alone, or with control bi-specific antibody showed no T cell proliferation, suggesting T cells are tolerant to the self-tumor Ags. Together, these data demonstrated that specific activation of T cells by ESK-bi-specific antibody required the presence of tumor cells and that ESK-bi-specific antibody could force T cells to overcome the self-tolerance. The ability of the ESK-bi-specific antibody to induce autologous T cell proliferation and killing of its target cancer cells was illustrated in a second autologous model from a patient with AML (FIG. 16A-16D).

Therapy of Human Leukemia Expressing WT1/HLA-A0201 in NSG Mice.

Figure 4B:
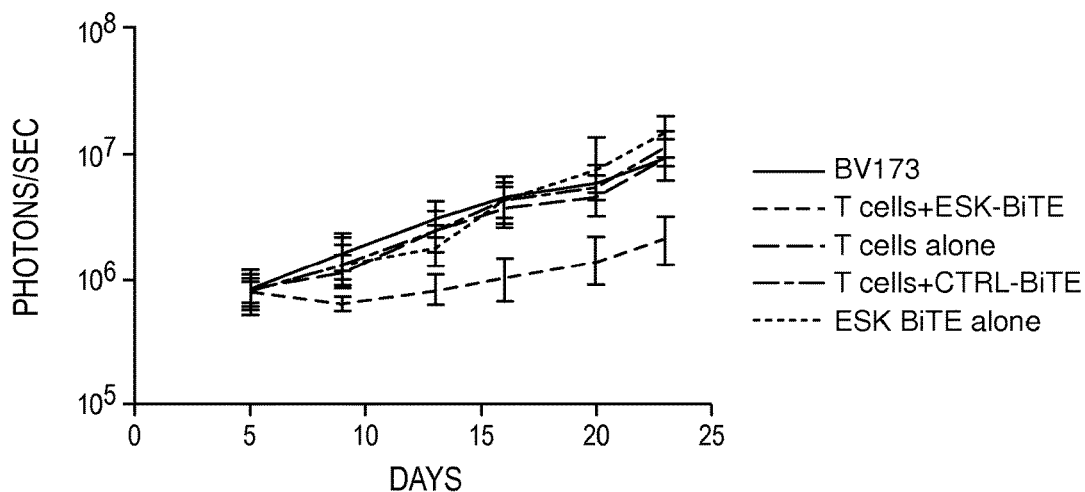
FIG. 4 shows that ESK-bi-specific antibody effectively treats BV173 and ALL in NSG mice. Two million BV173 cells were injected i.v. into mice on day 0, the tumor engraftment was confirmed on day 5, and mice were randomized into treatment groups. Ten million EBV-specific T cells were given intravenously on day 6, followed by 20 µg of ESK1 or control bi-specific antibody i.v. injection 4 to 5 hours later. T cells were given once a week and bi-specific antibodies were given twice a week for a total of three weeks. (4A) Tumor burden was shown by bioluminescence imaging (BLI) from the front of mice. BLI on day 6 showed tumor engraftment before treatment. The mice that received T cells and ESK-bi-specific antibody showed significant reduction of tumor burden, especially in bone marrow. (4B) Tumor burden was calculated by summing the luminescent signal of each mouse in back and front two positions, and average signal for each group (n=5) was plotted. (4C) GVHD was assessed by weighing mice every week, and no GVHD was observed up to 49 days. (4D) ESK-bi-specific antibody inhibited primary ALL cell growth in NSG mice. Five million primary tumor ALL cells were injected i.v. into NSG mice. On day 6, after confirming tumor engraftment by firefly BLI, mice were randomly divided into different treatment groups. Thirty million EBV-specific T cells were iv injected into mice followed by i.v. injection of 20 µg ESK-bi-specific antibody or its control bi-specific antibody. Bi-specific antibody injection was given daily, and T cells were given twice a week for a total of two weeks. Tumor inhibition on day 18 and day 23 after tumor inoculation is shown in prone and supine views for each time point. (4E) Data from the ALL mouse model: average photon/second from five mice showed a nearly hundred-fold reduction of tumor burden in the mice treated with ESK-bi-specific antibody after more than 3 weeks.
Figure 4C:
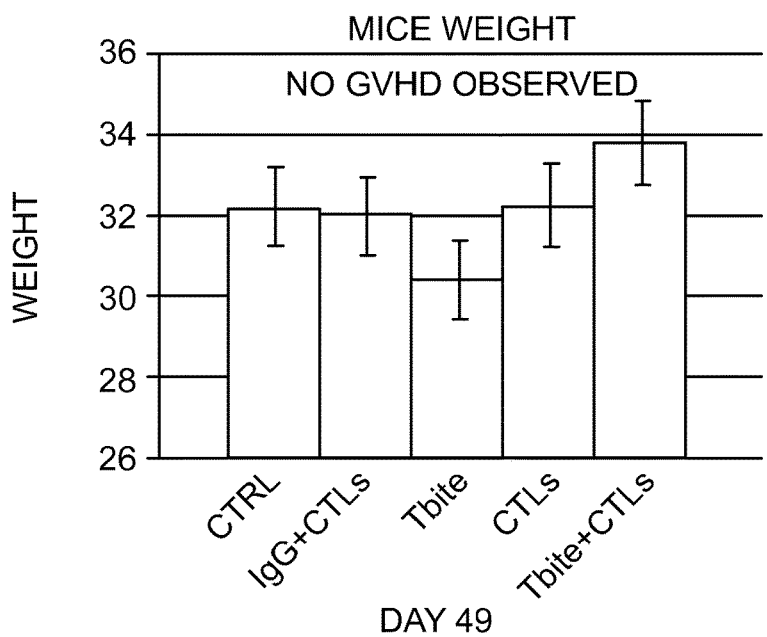

The in vivo therapeutic efficacy of ESK-bi-specific antibody in NSG mice xenografted intravenously 6 days previously with BV173 Ph+ALL cells was tested. At the time of treatment, mice had disseminated leukemia visible in their liver, spleen, and bone marrow. T cells were i.v. injected into mice and followed by bi-specific antibodies 4 hrs later. Dramatic tumor inhibition was observed, which was especially prominent in the bone marrow of mice that received ESK-bi-specific antibody, starting three days post-treatment and persisting up to 3 weeks (FIG. 4A). On the contrary, all mice in the control groups that included the mice received tumor cells, tumor along with T cells, tumor with ESK-bi-specific antibody, or tumor cells along with T cells and control bi-specific antibody, showed increasing tumor growth and massive tumor burdens in the bone marrows and other organs (FIG. 4A). The average of photon intensity from five mice showed approximately 10-fold tumor reduction in the ESK-bi-specific antibody-treated group (FIG. 4B). No significant GVHD was observed up to 49 days post-tumor inoculation (FIG. 4C). The results demonstrated that ESK-bi-specific antibody could efficiently engage and direct potent T cell cytotoxicity to kill BV173 target cells.

Figure 4E:
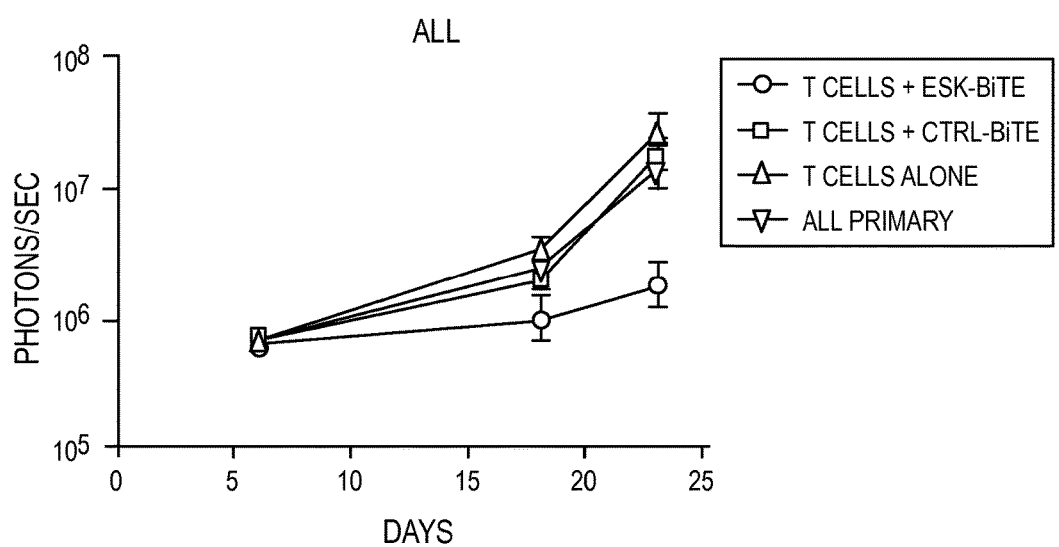

The therapeutic efficacy in vivo of ESK-bi-specific antibody in NSG mice xenografted intravenously with primary ALL cells was tested. T cells were injected i.v. into mice followed by ESK-bi-specific antibody injection. All mice in the control groups showed increasing tumor growth and massive tumor burdens in the bone marrows and other organs. Dramatic bi-specific antibody-selective tumor inhibition was observed, which was especially prominent in the bone marrow of mice, persisting more than 3 weeks, 9 days after treatment was stopped (FIG. 4D). The average of photon intensity from five mice showed approximately 10-20 fold tumor reduction in the ESK-bi-specific antibody-treated group than other control groups (FIG. 4E). No significant GVHD was observed clinically up to 49 days post-tumor inoculation.

These results demonstrated that ESK-bi-specific antibody could efficiently engage and redirect potent T cell cytotoxicity to kill primary leukemia cells. As expected, EBV-specific human T cells did not show non-specific killing and therefore, could be used to address bi-specific antibody activity in xenograft models. This model suggested, and was confirmed with a pharmacokinetic study, that twice a week administration of ESK-bi-specific antibody was not sufficient, as its half-life was only a few hours.

Figure 5A:
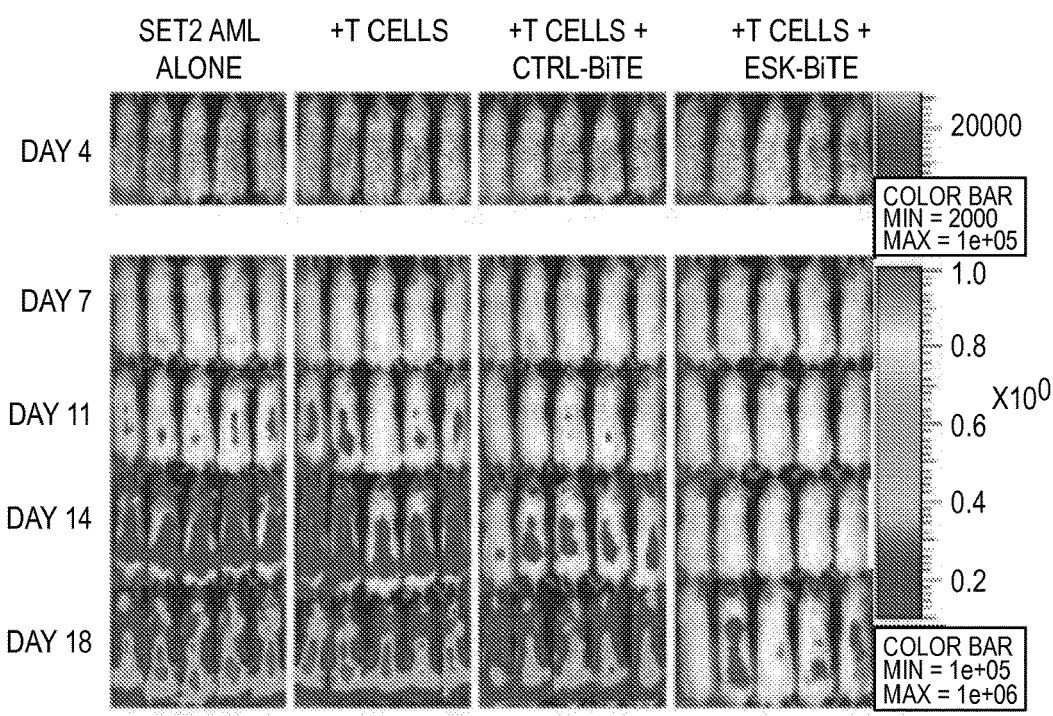
FIG. 5 shows that ESK-bi-specific antibody effectively treats SET-2 AML in NSG mice. In this model, ten million EBV-specific T cells were given i.v. twice a week and 20 µg bi-specific antibodies were injected i.v. daily for a total of 6 days, after confirming tumor engraftment on day 4. (5A) Tumor burden was shown from the back of mice to show spinal leukemia infiltration, in order to show the leukemia burden in all groups. BLI scale was increased about 10-fold on the images from day 7 onward. (5B) Tumor burden was calculated by summing the luminescent signal of each mouse in back and front two positions, and average signal for each group (n=5) was plotted. (5C) Leukemia infiltration was also assessed by limb paralysis caused by central nerve system damage. Mice that received T cells and ESK-bi-specific antibody showed no CNS paralysis. Each bar shows the average of five mice/group.
Figure 5B:
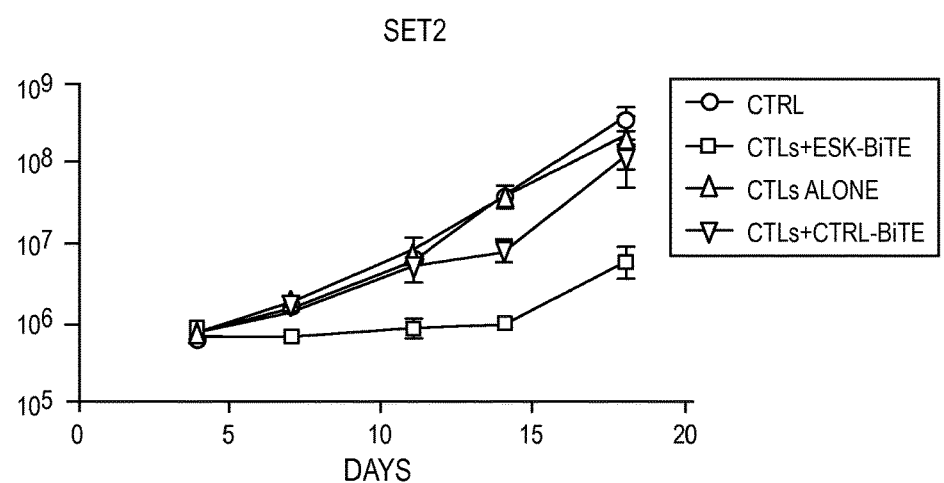
Figure 5C:
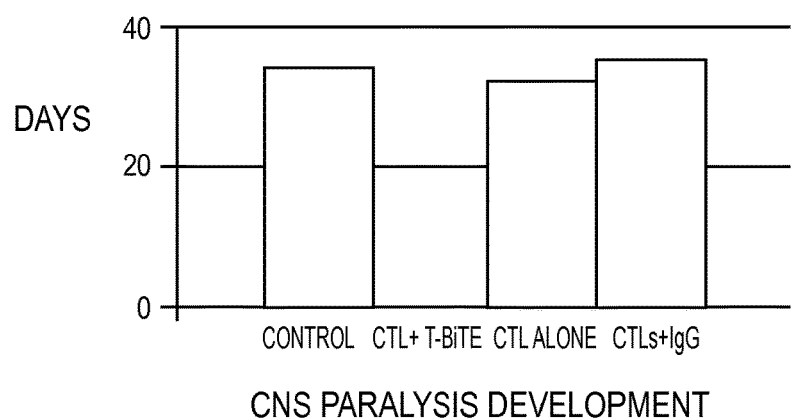
Figure 17A:
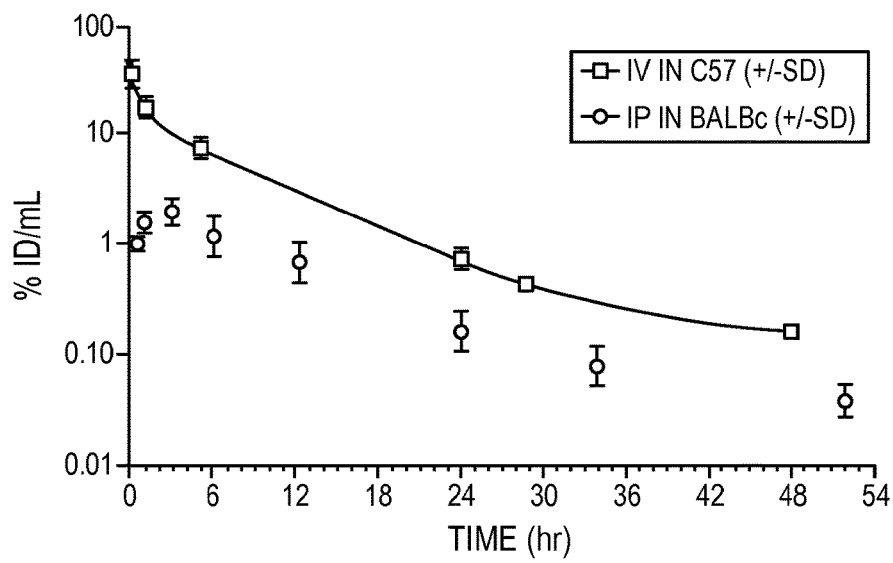
FIG. 17 shows pharmacokinetics of ESK-bi-specific antibody. Data represent the average of 3 mice/group. (17A) ESK bi-specific antibody pharmacokinetics was determined using trace $^{125}$I-labeled construct injected either intravenously into C57 BL6/J, or intraperitoneally into BALB/c mice, and blood radioactivity was measured over 48-52 hours. Intravenously injected bi-specific antibody quickly redistributed from blood to tissue with an alpha half-life of 30 minutes, followed by clearance with a beta half-life of 5 hours. After intraperitoneal delivery, bi-specific antibody levels increased in the blood, peaking at 3 hours post-injection. The construct then cleared with the same beta half-life. Total exposure (Area Under the Curve) from intravenous injection was greater than with intraperitoneal injection. (17B) The biodistribution pattern of the antibodies was determined using the same radiolabeled constructs. After 2 hours, 3% or less of the injected dose/gram was detected in major tissues other than the stomach and intestinal tract, which clears dehalogenated iodine. After 4 hours, 2% or less of the injected dose/gram was detected in major tissues other than the stomach. After 7 hours, 1% or less of the injected dose/gram was detected in major tissues other than the stomach.

Since ESK-bi-specific antibody seemed to be more effective in treating bone marrow leukemia as shown in BV173 model, this effect in a more aggressive AML cells SET-2 model was investigated. SET-2 cells tend to migrate to bone marrow rapidly upon engraftment. Dosing and schedule was guided by pharmacokinetic studies that showed a short, 5-hour, beta plasma half-life of the ESK-bi-specific antibody (FIG. 17A). The treatment dosage was increased to daily bi-specific antibody injection for a total of 6 consecutive days. Cells were given twice a week. The mice received treatment starting on day 4 post-tumor inoculation, when the leukemia engraftment was confirmed by BLI (FIG. 5A, first row). SET-2 cells rapidly grow in bone marrow, and a massive infiltration of leukemia was seen in the bone marrow of mice that received SET-2 cells or SET-2 along with T cells. However, no detectable leukemia was seen in the ESK-bi-specific antibody-treated group up to 14 days and only a minimum leukemia burden was observed up to 18 days later at day 32, more than a week after treatment was stopped. The gain on the BLI scale was uniformly decreased for all groups for the images from day 7 to 18, in order to show low levels of leukemia in the pretreated time point. The control-bi-specific antibody group showed slightly delayed leukemia burden in the beginning. This could be caused by activation of EBV-specific T cells by anti-CD3 arm of the control-bi-specific antibody, which had stronger binding affinity for T cells than ESK-bi-specific antibody (FIG. 1C). EBV-specific T cells had already been activated and expanded multiple times in vitro, rendering them more susceptible to a strong polyclonal stimulation. Activated T cells then release inflammatory cytokines which could create a hostile environment for tumor cells. While all the mice in ESK-bi-specific antibody-treated group were still alive after a month, there was only 20% of survival in the groups of mice treated with T cells alone or no treatment (FIG. 5B). The mice in ESK-Bi-specific antibody-treated group showed no sign of central nerve system (CNS) paralysis, caused by leukemia infiltration into vertebral bone marrow for up to 40 days, whereas nearly all animals in the control group were affected. (FIG. 5C). These data demonstrated that ESK-bi-specific antibody is a potent therapeutic agent against aggressive leukemia cells in bone marrow.

ESK-Bi-Specific Antibody Mediates T Cell Retention at Tumor Sites.

Figure 6A:
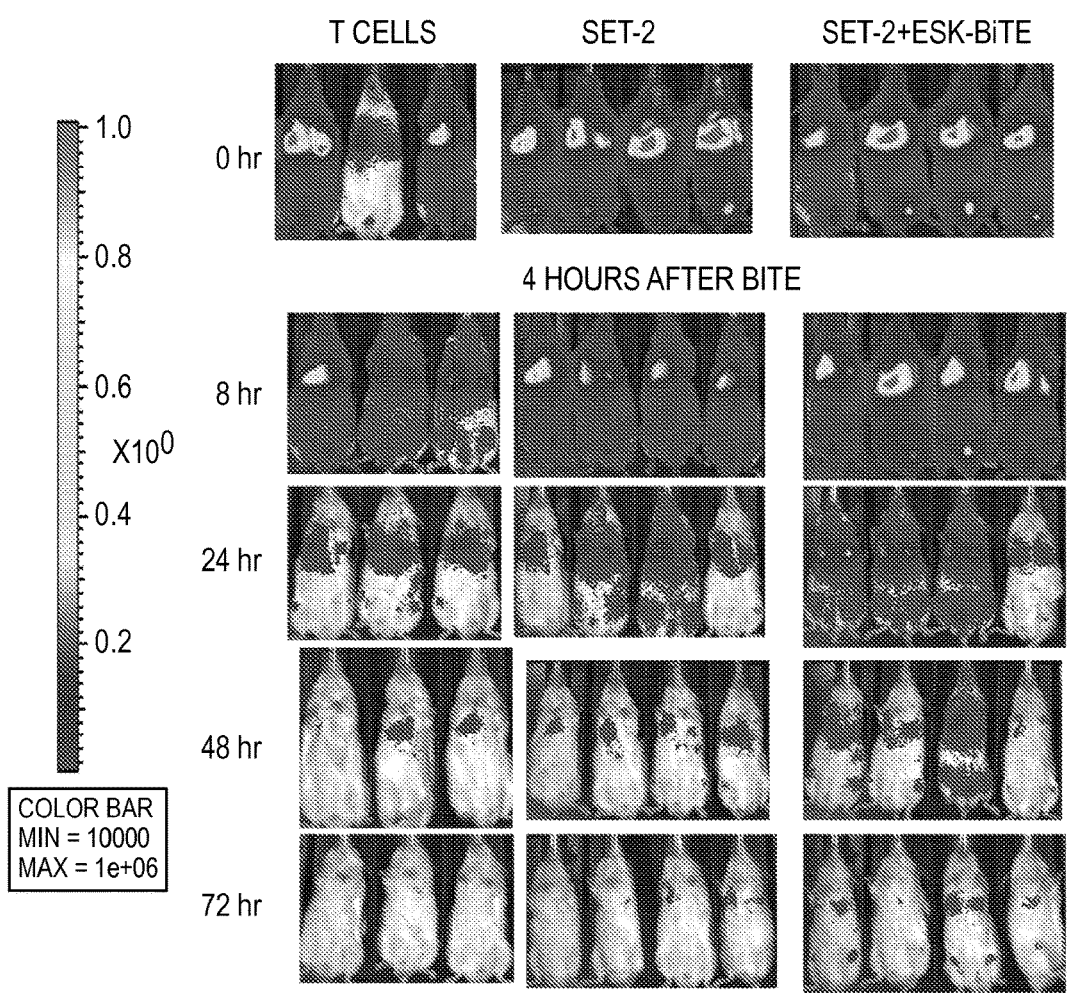
FIG. 6 shows that ESK-bi-specific antibody mediates T cell retention in bone marrow of tumor-bearing mice. (6A) Twenty million *Renilla*-transduced EBV-specific T cells were injected i.v. into mice that had been engrafted with SET-2 cells. Four hours later, 20 µg ESK or control bi-specific antibody was given by i.v. injection. T cell distribution was monitored by *Renilla* bioluminescence imaging, immediately after T cell injection (0 hr), 4 hrs after bi-specific antibody injection and then every day for a total of three days. (6B) T cell signal was calculated by summing the luminescent signal of each mouse and average signal for each group (n=3) was plotted. (6C) SET-2 leukemia burden was simultaneously monitored by firefly bioluminescence imaging at the indicated time points. Mice that received T cells alone showed no firefly signal. Mice that received T cells and ESK-bi-specific antibody showed a dramatic reduction of leukemia burden, compared to the mice that received SET-2 cells. Tumor inhibition was correlated with T cell retention as shown in FIG. 7B.
Figure 6B:
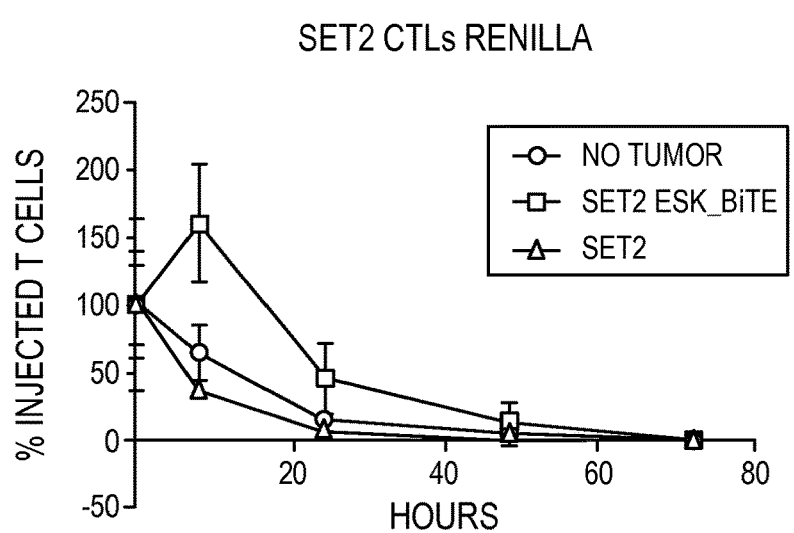
Figure 6C:
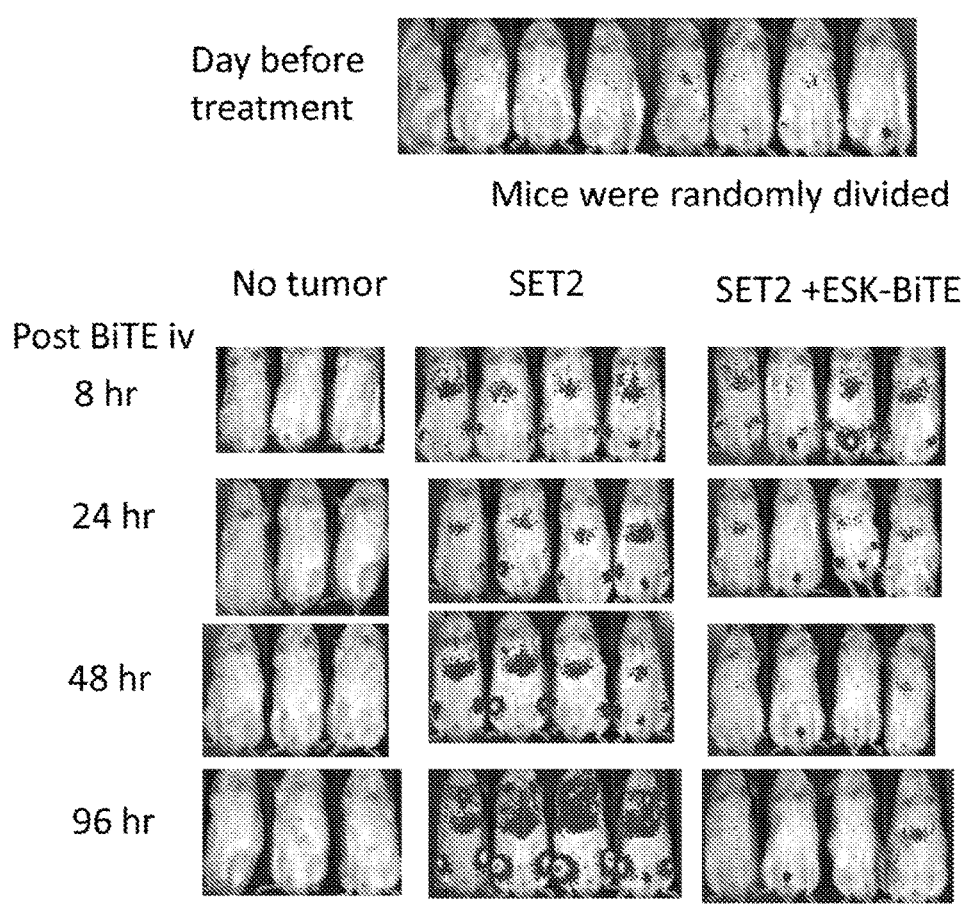

While it is known that bi-specific antibodies effectively engage T cells to kill targets in vitro, no in vivo studies have been reported that document the mechanism in vivo. Whether the therapeutic efficacy of ESK-bi-specific antibody was the result of its ability to attract T cell retention and persistence at the sites of leukemia in live animals was investigated. Ten million EBV-specific T cells transduced with *Renilla*/luciferase were injected into NSG mice three days after GEF/luciferase positive SET-2 AML cells were engrafted, and 4 hrs later followed by bi-specific antibody injection. T cell migration was monitored by luminescence imaging at the time of T cell injection (0 hr), 8 (i.e., 4 hrs after bi-specific antibody injection), 24, 48 and 72 hrs. T cells migrated into the lungs immediately after the injection, then distributed into other parts including liver, spleen and bone marrow at 8 hrs (FIG. 6A). T cell signal gradually declined over 72 hrs. T cell injection followed by control bi-specific antibody showed a similar distribution pattern and time course as T cells alone. However, mice treated with ESK-bi-specific antibody showed significant increase in T cell signals in lungs and BM from 4-20 hrs, which lasted up to 72 hrs. Cells declined in the lungs substantially, but remained in the liver, spleen and BM. Quantitation of bio luminescence intensity showed that 4 hrs after the ESK-bi-specific antibody injection, there was approximately three-fold more T cell accumulation into the liver, spleen and bone marrow compared to the other two control groups (FIG. 6B). Monitoring the leukemia progression at the same time revealed an inversed correlation between T cell retention and leukemia burden (FIG. 6C). These results provided strong in vivo evidence that ESK-bi-specific antibody could mediate prolonged retention of T cells at the leukemia sites, and effectively directed T cell cytotoxicity to the tumor cells expressing WT1 and HLA-A0201.

Therapy of Mesothelioma in NSG Mice.

Figure 7A:
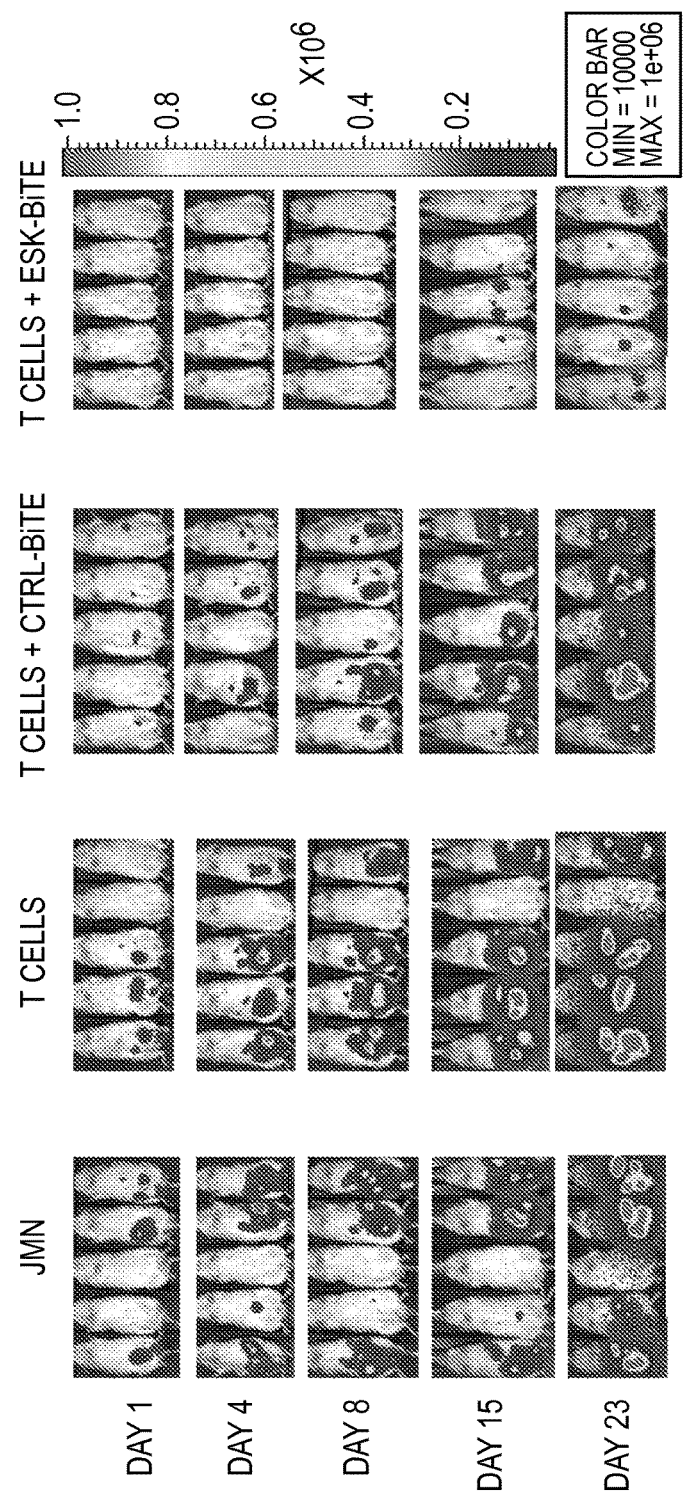
FIG. 7 shows that ESK-bi-specific antibody eliminates peritoneal mesothelioma cells JMN in NSG mice. Three thousand JMN cells were mixed with six thousand EBV-specific T cells and were i.p. injected into mice. One hour later, ESK or control bi-specific antibody was i.v. injected and was repeated for 5 consecutive days. Tumor development was monitored by firefly bioluminescence imaging at the indicated time points. (7A) Day 1 (one day after treatment) showed no visible tumor in the mice treated with ESK-bi-specific antibody, suggesting the elimination of tumor cells. (7B) Average photon/second from five mice showed nearly hundred fold reduction of tumor burden in the mice treated with ESK-bi-specific antibody after more than 3 weeks.
Figure 7B:
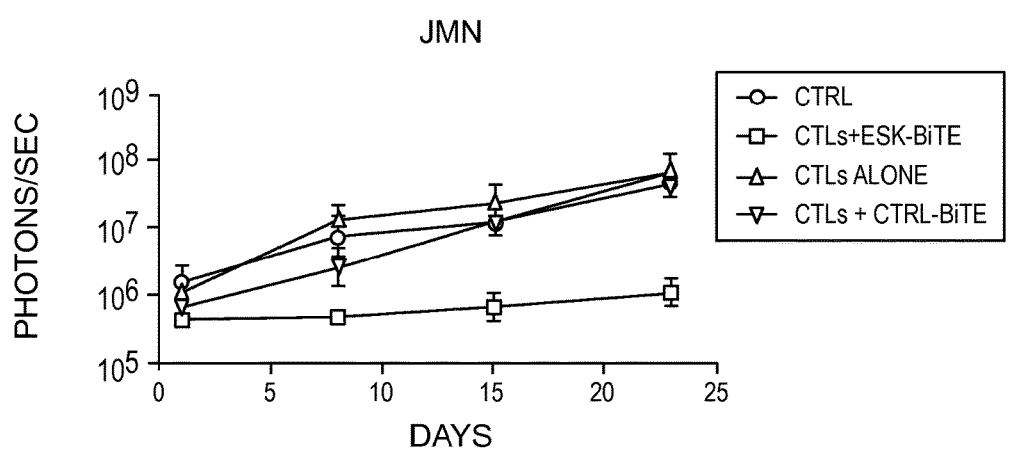

Having shown the potent therapeutic activity of ESK-bi-specific antibody in two leukemia xenograft models, the efficacy of ESK-bi-specific antibody in treating aggressive solid tumor was investigated using an i.p. model to simulate peritoneal cavity mesothelioma. WT1+/HLA-A0201+ JMN mesothelioma cells were mixed with EBV-specific T cells at a target-effector ratio of 1:2 and were i.p. injected into NSG mice. Bi-specific antibodies were i.v. injected one hr later and was repeated for 5 consecutive days. Bioluminescence imaging one day later showed no visible tumor in the mice treated with ESK-bi-specific antibody, while mice in three controls groups showed visible tumor burden, suggesting that ESK-bi-specific antibody had eliminated tumor cells (FIG. 7A). The tumor suppression by ESK-bi-specific antibody persisted until day 23; 18 days after the treatment was stopped, only a minimum tumor burden was seen in the mice. Averaging the bioluminescence intensity of five mice per group showed a persistent and approximately more than 20-fold tumor suppression on day 23 (FIG. 7B).

Figure 17B:
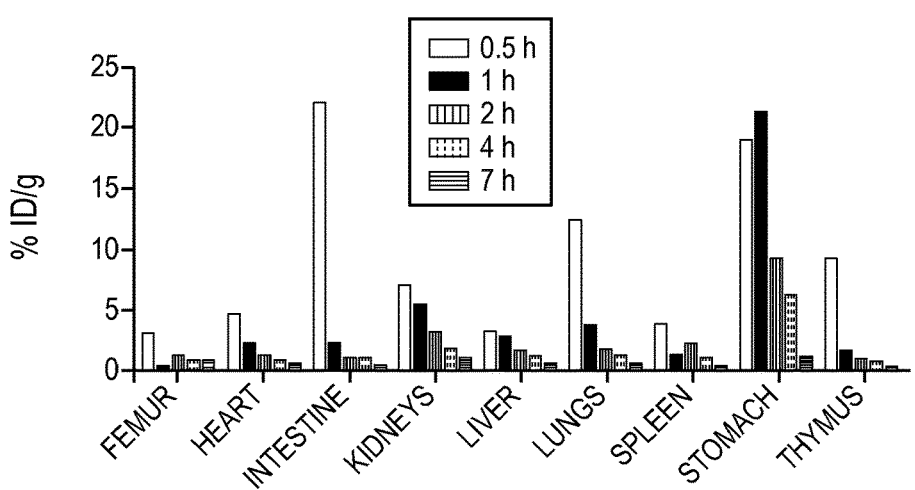

Pharmacokinetics: To determine ESK bi-specific antibody pharmacokinetics, trace $^{125}$I-labeled construct was injected either intravenously into C57 BL6/J, or intraperitoneally into BALB/c mice, and blood radioactivity was measured over 48-52 hours. Intravenously injected bi-specific antibody quickly redistributed from blood to tissue with an alpha half-life of 30 minutes, followed by clearance with a beta half-life of 5 hours. After intraperitoneal delivery, bi-specific antibody levels increased in the blood, peaking at 3 hours post-injection. The construct then cleared with the same beta half-life. Total exposure (Area Under the Curve) from intravenous injection was greater than with intraperitoneal injection. The biodistribution pattern of the antibodies was determined using the same radiolabeled constructs. After 24 hours, <1% injected dose/gram was detected in all tissues (FIG. 17A, 17B).

Figure 18A:
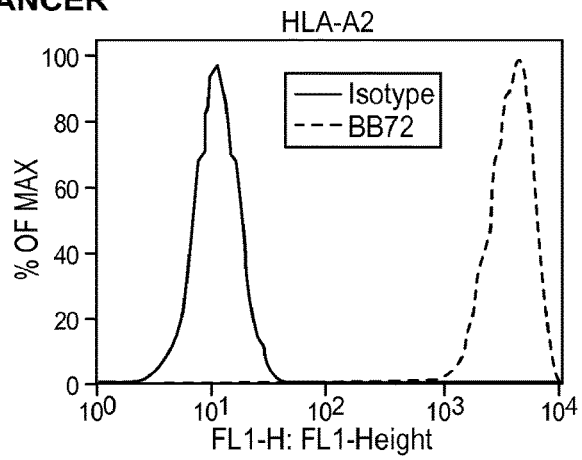
FIG. 18 shows the expression of tumor antigens on primary ovarian cancer cells. (18A) The expression of HLA-A2 on primary ovarian cancer cells was measured by staining the tumor cells with anti-human HLA-A2 mAb clone BB7.2 conjugated to FITC and its isotype control mouse IgG2b/FITC. (18B) Expression of the WT1 RMF/HLA-A2 complex on the same tumor cells was measured by staining the cells with mAb ESK conjugated to APC at 3 µg/ml and its isotype control, human IgG1/APC. (18C) Her2-neu expression on the same tumor cells was measured by staining the cells with Herceptin at 10 µg/ml or 1 µg/ml, followed by goat anti-human IgG1 mAb conjugated to FITC. Rituximab was used as isotype control.
Figure 18B:
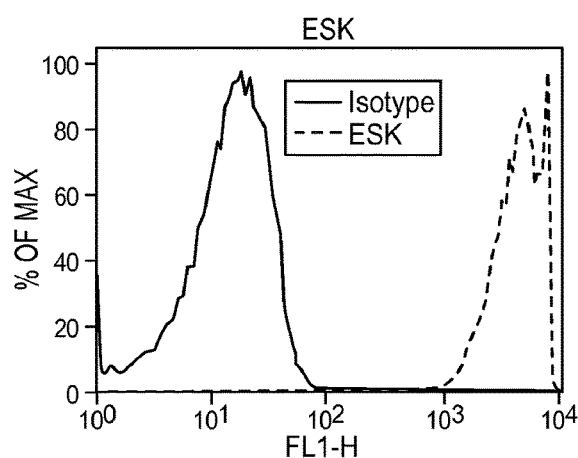
Figure 18C:
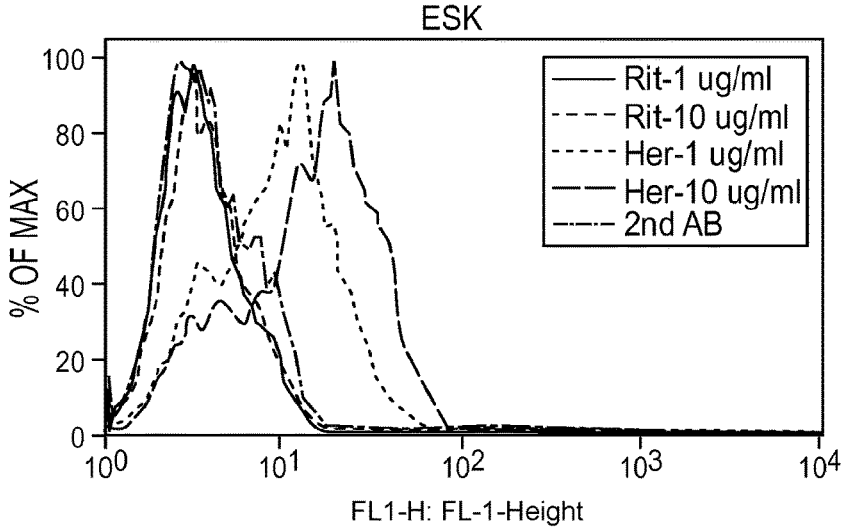

ESK-Bi-specific antibody induced secondary T cell response to a HER2 epitope in the context of HLA-A0201. The mechanism of the action for bi-specific antibodies has been attributed to their direct effect of bridging the cancer cell targets and T cells to form a cytolytic synapse. Whether such a proximal contact could directly activate pre-existing T cells in the population specific for other tumor antigens expressed by the autologous tumor cells was investigated to determine if a bi-specific antibody could exert a vaccinal effect using the autologous in vitro model from a HLA-A*02:01 positive patient with ovarian cancer. The patient's PBMCs were co-cultured with her autologous tumor cells in the presence of low-dose ESK-bi-specific antibody; a week later, the epitope-specific HLA-A*02:01-restricted T cell responses were assessed by IFN-g ELISPOT assay. Control groups including the cells alone or with control bi-specific antibody did not show any specific IFN-g release. The patient's tumor cells expressed both WT1 RMF and HER2-neu on their cell surface (FIG. 18A-C). Surprisingly, a strong secondary T cell response was induced against HER2-neu-369 epitope, the autologous tumor cells alone, and SET-2 AML cells, long after ESK-bi-specific mediated interactions were terminated (FIG. 19A-F). No response in these autologous cells was measurable against 56 pooled WT1-derived epitopes, WT1 epitopes RMF, AILDF05 or LDF; p53-derived epitope 264-273; Prame-300, Prame-435; Ewings sarcoma epitope EW, Muc1-15, -16, and -18; or HL60 cells. Since SET-2 does not express HER2-neu, and the T cells did not recognize WT1 RMF, the T cell response against SET-2 showed recognition of other yet to be defined epitopes that are neither WT1 nor HER2-neu. These results clearly demonstrated that ESK-bi-specific antibody could induce secondary T cell responses to multiple tumor antigens, thereby providing an unexpected vaccinal effect.

In principle, a secondary T cell response should require professional APCs among the PBMCs that could take up and present the intracellular antigens released after tumor cell death. Alternatively tumor cells could directly activate pre-existing epitope-specific T cells during the proximate contact between T cells and tumor. To clarify the mechanism, it was investigated whether the vaccinal effect could occur with purified T cells, and NK cell-depleted and macrophage-depleted PBMCs (T plus B cells) versus whole PBMCs as effector cells. Interestingly, T cells alone as effectors still were capable of the response to HER2-neu, autologous tumor cells and SET-2 cells, in a similar magnitude as that produced by T plus B cells (FIG. 19C) or whole PBMCs (FIG. 19D). To exclude a possibility of T cell presentation itself of these self-cancer antigens, purified T cells were co-cultured with autologous tumor cell lysates, generated by repetitive freeze thaw, in the presence or absence of ESK-bi-specific antibody. No T cell response was seen against the HER2-neu epitope or tumor cells in this setting (FIG. 19D). These results demonstrated that neither professional APCs nor epitope tumors were required for the bi-specific antibody-induced secondary T cell response to HER2-neu or other epitopes present in tumor cells, therefore, cross-presentation was not the mechanism.

Figure 19E:
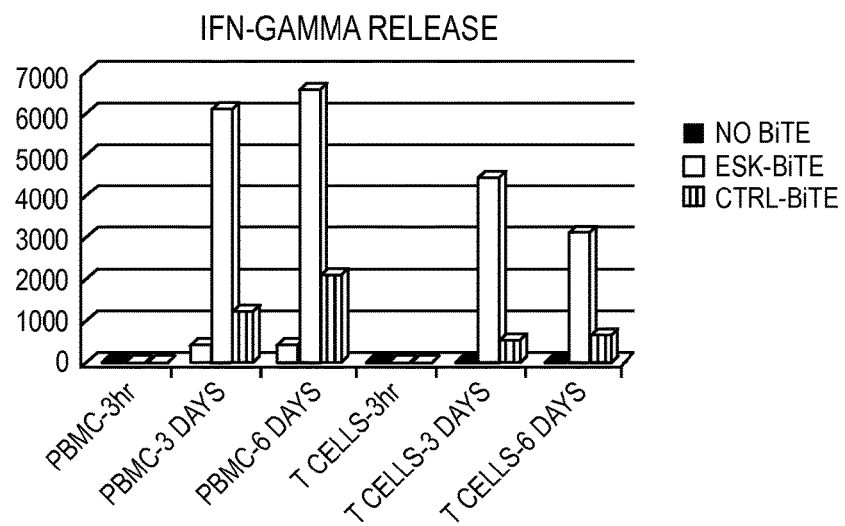
FIG. 19 shows ESK-bi-specific antibody induces secondary T cell responses to epitopes other than WT1 RMF in the context of HLA-A2 molecules. (19A) PBMCs from a patient with ovarian cancer were stimulated with autologous tumor cells at an effector:target ratio of 5:1, in the presence of ESK-bi-specific antibody or control bi-specific antibody at 0.1 µg/ml, human IL-5 (5 ng/ml) and human IL-2 (10 unit/ml) for a week and the epitope-specific response was measured by IFN-g elispot assay, against T2 cells, pulsed with indicated peptides at 20 µg/ml. (19B) Remaining PBMCs from the experiment in (A) were re-stimulated in the same manner, at an effector:target ratio of 9:1, and epitope-specific T cell response was measured by IFN-g elispot assay. The same stimulation protocol and IFN-g elispot assay were conducted to compare epitope-specific T cell response between (19C) purified CD3+ T cells versus PBMCs depleted of NK and macrophage (indicated as T+B), or (19D) PBMCs versus purified CD3+ T cells, or T cells stimulated with dead autologous tumor cells. Dead tumor cells were generated by frequent freeze thawing without DMSO. The data represent the average of triplicate culture+/−SD. Supernatant from the co-cultures of PBMCs or purified T cells with autologous ovarian cancer cells in the presence or absence of bi-specific antibodies at 0.1 µg/ml, were collected after 3 hours, 3 and 6 days and IFN-gamma (19E) and TNF-alpha (19F) were measured by ELISA kits.
Figure 19F:
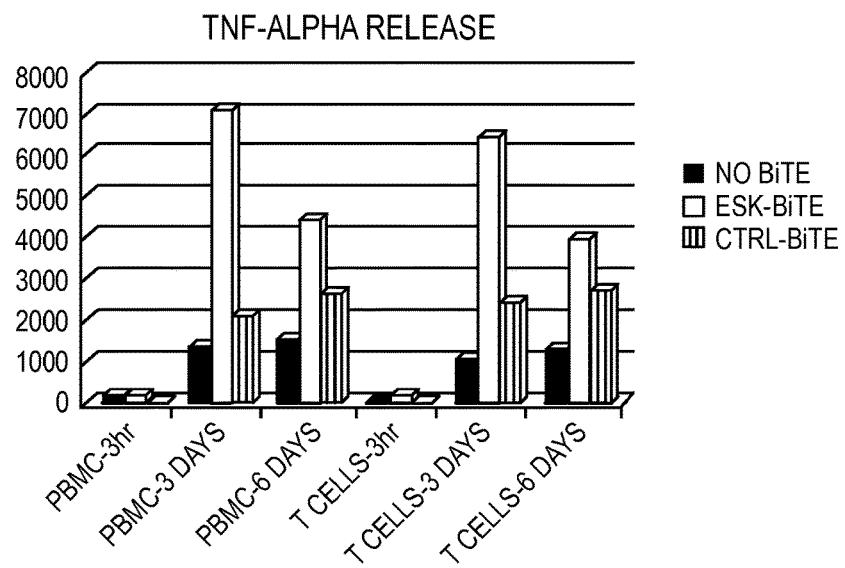
Figure 20:
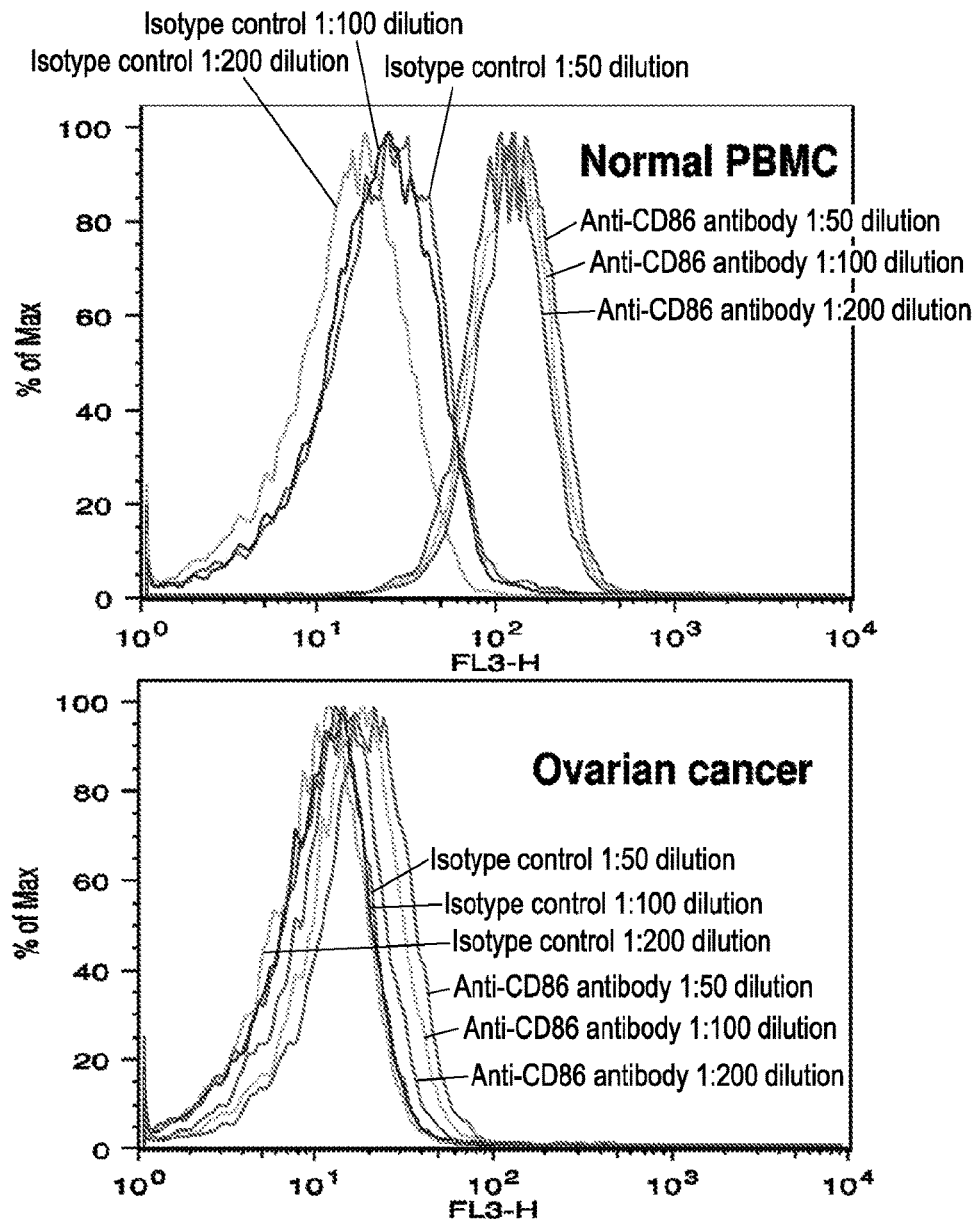
FIG. 20 shows co-stimulatory molecule CD86 expression on PBMCs (top panel) from a normal donor and ovarian cancer cells from a patient (bottom panel), measured by staining the cells with mouse anti-human CD86 mAb/PerCp or its isotype control at different concentrations. Isotype control: 1:50, 100 and 200 dilution. Anti-CD86 antibody: 1:50, 100 and 200 dilution.

It was also examined if tumor cell antigen presentation depended on co-stimulatory molecules. While CD14+ monocytes from a healthy donor showed strong CD86 expression, ovarian cancer cells had little expression of the CD86. The results indicated that a key co-stimulatory molecule CD86 was unlikely to be involved in the tumor cell antigen presentation (FIG. 20). No CD86 or ICOSL expression was detected. Lack of co-stimulatory molecules is one of the reasons that tumor cells are poor antigen presenting cells; however, certain cytokines may provide co-stimulatory signals to fulfill the requirements for tumor specific T cell activation. ESK-bi-specific antibody induced IFN-gamma and TNF-alpha secretion by both PBMCs and T cells (FIG. 19E-F).

Figure 21A:
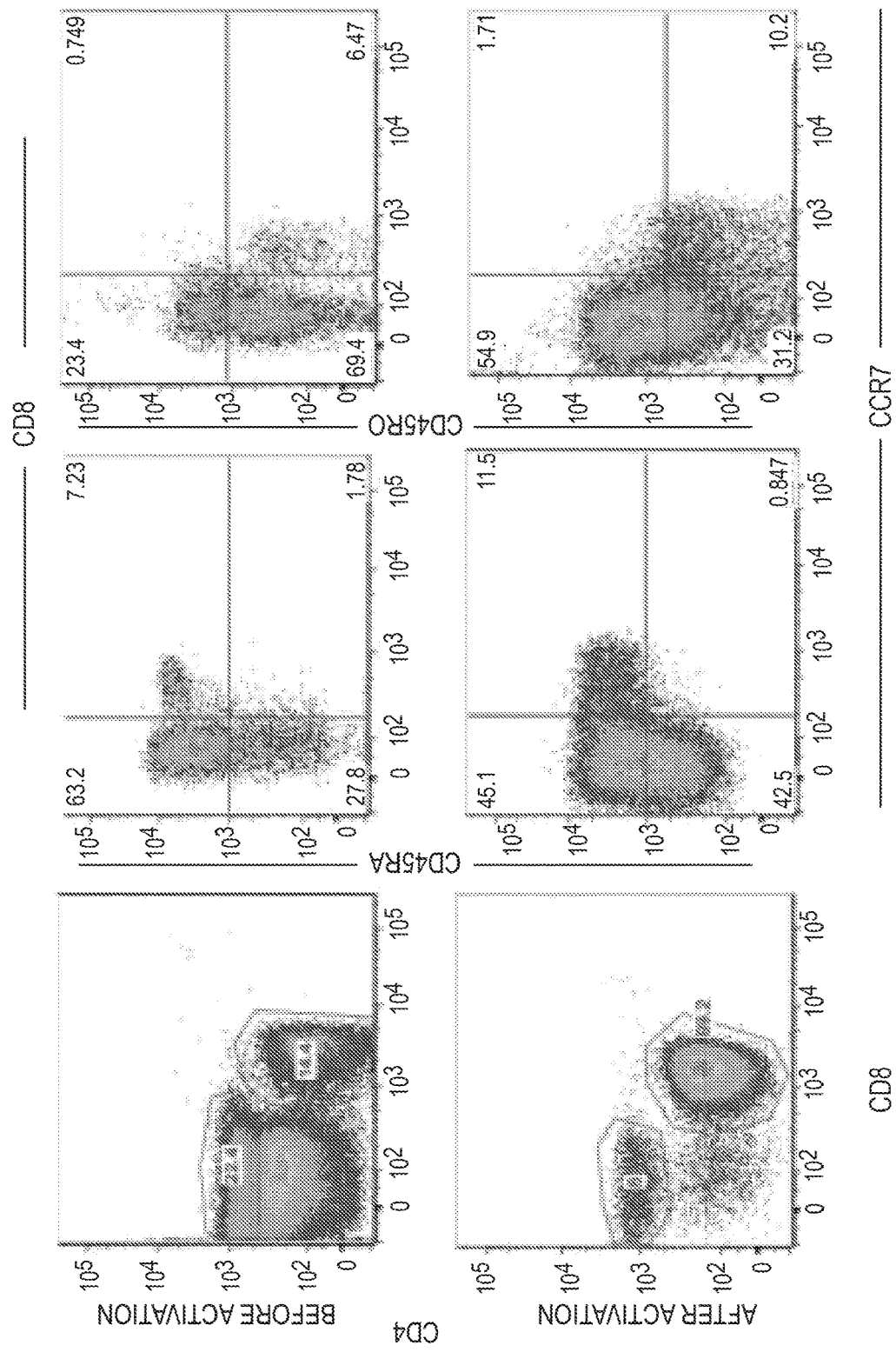
FIG. 21 shows generation of long-lived, cytotoxic effector cells. (21A) PBMCs from the patient in FIG. 19 were stained with CD4, CD8, CD45RA, CD45RO and CCR7, before and 7 weeks after activated with ESK-bi-specific antibody (0.1 µg/ml) in the presence of autologous tumor cells. CD45RA and CD45RO versus CCR 7 were shown on gated CD8 T cells. (21B) The large selective increase in CD8 T cells 7 weeks after bi-specific antibody activation as measured by flow cytometry and cell counting. (21C) Effector cells from the experiments shown in FIG. 19 were expanded by weekly supplement of IL-15 (5 ng/ml) and IL-2 (10 U/ml) for 5 weeks, and cytotoxicity was measured against autologous tumor, SET-2 and HL-60 cells by standard $^{51}$Cr-release assay. The data represent the average of triplicate wells.
Figure 21B:
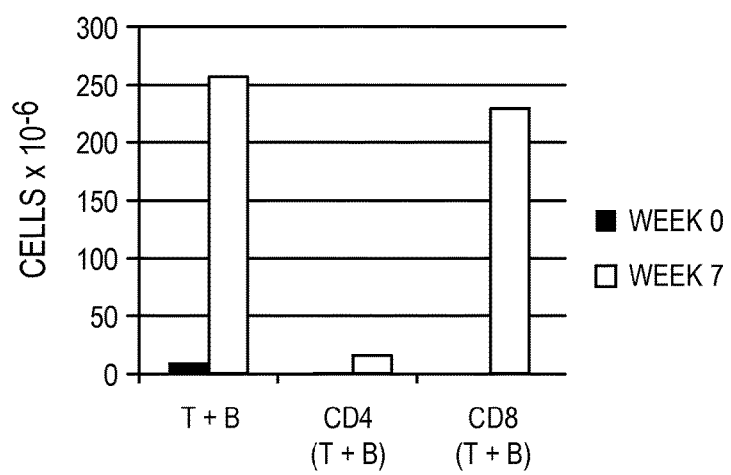
Figure 21C:
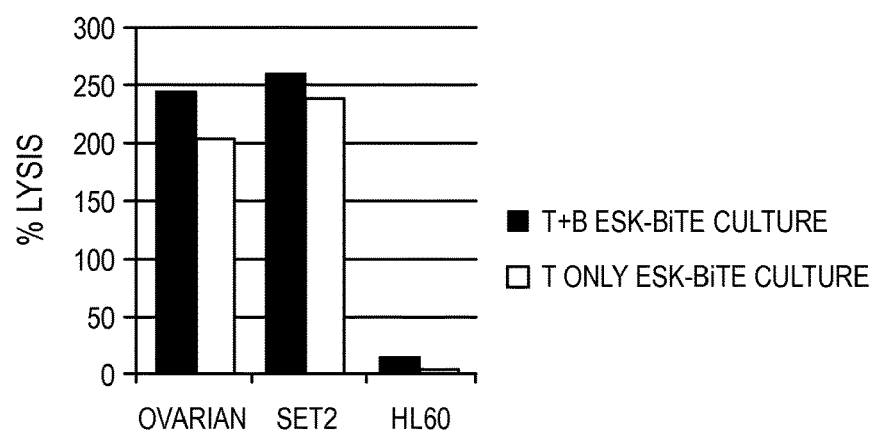

To test if ESK-bi-specific antibody had any long-term effect on the T cell population, T cells were expanded in vitro in low-dose IL-15 and IL-2, after the first activation by ESK-bi-specific antibody. While T cells in control groups did not survive more than one week in culture, T cells activated by ESK-bi-specific antibody continued to grow for 2 months, without further activation. Phenotype analysis revealed that seven weeks after activation by ESK-bi-specific antibody and tumor, CD8+ T cells increased to 89% of the population and CD4+ T cells decreased to 6% (FIG. 21A-B). Interestingly, among the CD8+/CCR7− cells, CD45RA−/CD45RO+ cells increased, indicative of effector memory phenotype. Importantly, even at this late time point, these T cells still retained their original specificity to autologous tumor and SET-2 AML cells (FIG. 21C). These results indicated that ESK-Bi-specific antibody could induce a long-lasting secondary specific CD8 T cell responses.

Discussion

The present disclosure provides the first bi-specific antibody construct derived from a TCR-like mAb. The ESK-bi-specific antibody was specific for the WT1 RMF epitope presented by HLA-A0201 molecule. The ESK-bi-specific antibody showed a potent anti-tumor activity against multiple cancers, including ALL, AML, mesothelioma and primary ovarian cancer cells, both in vitro and in vivo. The study presented here is distinguished from previous studies, in that: 1) the mAb is a TCR-like mAb allowing recognition of an intracellular tumor-specific target; 2) the target density on tumor cells is extremely low, providing a proof-of-concept that could open the application of bi-specific antibodies to a much larger universe of targets; 3) the mechanisms of the ESK-bi-specific antibody activity in vivo with simultaneous dual effector cell and target cell tracing were demonstrated (previous bi-specific antibody studies have not shown this because in most animal studies, the effector T cells and target cells were mixed before injection; 4) Using an autologous system, it was demonstrated that the ESK-bi-specific antibody could break T cell tolerance to kill primary ovarian cancer cells; 5) the ESK-bi-specific antibody induced long-lived secondary, specific T cell responses against other tumor antigens, such as HER2-neu. Further, the secondary T cell responses were not mediated by cross-presentation effected by classical APCs, but rather was a result of the direct and physically close interaction between T cells and tumor cells, fostered by the bi-specific antibody.

All the bi-specific antibody constructs that are currently in development target cell surface proteins, such as CD19, CD33, prostate specific membrane antigen (PSMA) or epidermal growth factor (EGF) receptor, that are lineage or differentiation antigens found on normal cells. In contrast, the present disclosure demonstrates for the first time that a TCR-like bi-specific antibody construct is capable of recognizing a low density epitope of a peptide/MHC complex from a tumor-specific target. This argues against a traditional view that a scFv bi-specific antibody construct might not be suitable for targeting a low density Ag because the affinity would be too low or the ability to activate cytotoxicity by T cells would be insufficient. The present disclosure demonstrates for the first time that a TCR-mimic bi-specific antibody construct is capable of potent therapeutic activity in several mouse models of both hematopoietic and solid tumors, providing the proof of concept for vastly broadening the development of bi-specific antibodies targeting other cancer-specific intracellular tumor antigens. While it is known from assays in vitro that bi-specific antibodies bring T cells in contact with cancer cells, such a mechanism had not previously been observed in vivo. The present disclosure provides the proof of concept for future development of bi-specific mAbs targeting other intracellular tumor Ags. Thus, the ESK-bi-specific antibody described herein could broaden the therapeutic application of the platform.

In one embodiment, the ESK-bi-specific antibody induced fast and potent cytotoxic activity in vitro against lymphoid and myeloid leukemias, mesothelioma, and primary ovarian cancer cells, co-expressing WT1 and HLA-A0201. Lysis of the target cells by resting T cells or EBV-specific T cells could be detected in five hour co-incubation, compared to the studies with various other bi-specific antibody constructs that showed T cell killing after more than 16 hour of cultures. The cytolytic activity of ESK-bi-specific antibody could be further enhanced by longer period of incubation, shown by up to 80-90% of killing achieved with the SET-2 AML cells. This shared a similar feature with other bi-specific antibody mAbs specific for the CD33 and CD19, suggesting that ESK-bi-specific antibody engages T cell to targets in a serial fashion. IFN-g secretion further demonstrated the ESK-bi-specific antibody-mediated target-specific T cell activation. An important observation with clinical relevance is that ESK-bi-specific antibody could efficiently activate un-manipulated T cells from a patient with ovarian cancer to proliferate and kill the autologous tumor cells, suggesting that the presence of ESK-bi-specific antibody could force T cells to overcome the tolerance to self-tumor Ags. It has been known that T cell infiltration is frequently observed in solid tumors. The relatively low molecular weight of the bi-specific antibody would allow ESK-bispecific antibody better penetration into solid tumors to activate anergic or unresponsive T cells to kill the surrounding tumor cells.

The in vitro cytotoxicity of ESK-bi-specific antibody was evidenced in vivo as well, as shown by its remarkably potent therapeutic activity against Ph1+ALL, AML and mesothelioma in xenograft models. In both leukemia models, elimination of tumor cells was evident, especially in bone marrow. In addition, ESK-bi-specific antibody prevented and delayed CNS paralysis, a characteristic feature of leukemia caused by infiltration of vertebral bone marrow.

The ability of the ESK-bi-specific antibody to kill leukemia cells in vivo when the T cells were injected separately from the tumor cells (a schedule not typically used in preclinical bi-specific antibody experiments), raised questions about the mechanism of bi-specific antibody activity in vivo. The study with SET-2 cells further raised the question of whether ESK-bi-specific antibody actively recruits and retains T cell effectors at the target. These questions were addressed by simultaneously tracing effector T cells and SET-2 AML cells using dual bioluminescence imaging. There was approximately a three-fold increase in T cells in the bone marrow of the mice treated with ESK-bi-specific antibody. The T cell retention was well correlated with the tumor reduction. The present disclosure provides direct in vivo evidence that ESK-bi-specific antibody could efficiently engage T cells with targets and kill the tumor cells in situ.

The therapeutic activity of ESK-bi-specific antibody in a solid tumor model with a peritoneal human mesothelioma in NSG mice was investigated. The PK study showed that i.v. injection of the ESK-bi-specific antibody gave a higher level in the blood stream than i.p. injection but that the plasma half-life of the bi-specific antibody was characteristically short. Rapid and dramatic tumor inhibition was seen in the treated mice, suggesting that ESK-bi-specific antibody gained quick access to the peritoneal tumor cells. The PK studies confirmed the pharmacokinetic observations from other bi-specific antibody constructs, suggesting that continuous administration of ESK-bi-specific antibody may be necessary to achieve the best therapeutic efficacy.

Similar to other bi-specific antibody constructs, a limitation of ESK-bi-specific antibody is also the lack of a natural Fc region thus preventing interaction with the neonatal FcRn receptor, which is necessary for delaying mAb clearance and for longer blood PK. Engineering an alternative bi-specific form of mAb with dual target specificities yet maintaining its natural architecture could offer a longer half-life and could significantly improve its efficacy in clinical application. Interestingly, it was observed that the full length mAb ESK1 was more effective in eradicating disseminated leukemia BV173 cells in lung and liver in mice, while ESK-bi-specific antibody seemed to be more effective in bone marrow. This may reflect the content and types of effectors found in different organs in the body (e.g., macrophages in liver and T cells in the blood and bone marrow). This discrepancy also suggests that combinations of full length IgG and bi-specific antibody forms used together might provide additive effects, if the appropriate dose and schedule could be determined. Therapeutic TCR in mAb development is relatively recent and there are many unanswered questions regarding their possible applications. The development of bi-specific mAb approaches for TCRm mAbs will allow broadening of their scope to include not only tumor-specific antigens, but also intracellular targets and other important ultra-low density targets.

The mechanisms of bi-specific antibody action to date have been attributed to a direct interaction between T cells and the mAb-specified cellular target. An intriguing discovery was that ESK-bi-specific antibody specific for WT1 RMF epitope induced a secondary T cell response highly specific for other cancer antigens (and not the WT1 target), such as HER2-neu epitope 369, in an autologous ovarian cancer model. It was shown that such proximate contact between T cells and target cells could directly reactivate (without cross-presentation) tolerant or anergic T cells that existed in the patient, to react with other cancer antigens. Surprisingly, a robust and long-lasting HER2-neu epitope specific T cell response was detected, as well as other cancer-specific reactivities. There was an increase in CD8 T cells with effector memory phenotype, further supporting the observation of new epitope-specific T cell responses, because CD8 T cells must have been activated to proliferate in response to the HLA-A*02:01 restricted epitopes. The magnitude and duration of the single ESK-bi-specific antibody activation was far superior to the traditional peptide/APC-induced epitope-specific T cell response generally observed (Dao et al., supra). Interestingly, ESK-bi-specific antibody did not induce T cell responses against the original target epitope WT1-RMF, even though the patient had WT1 reactive T cells in her circulation as a consequence of prior adaptive cell therapy. These findings were consistent with the hypothesis that the bi-specific antibody is bringing the T cell's TCRs close to the tumor cell to recognize new MHC/peptide epitopes directly on the tumor and that the binding of the ESK-Bi-specific antibody to its peptide/MHC epitope during this T cell stimulation phase is blocking any recognition of the RMF/A0201 epitope from the cognate TCR of the T cells.

Expansion of T cells against various tumor antigens not present in the original vaccine have been detected in patients given vaccines or T cell infusions and has been associated with clinical responses; this phenomenon is referred to as "epitope spreading", and thought to be mediated by cross-presentation by APC's processing the apoptotic tumor cells (Corbiere, V. et al. Cancer Res. 71 (4), 1253-1262 (2011)). A vaccinal effect of mAb to CD20 has been reported; the effect also appears to be mediated by antibody mediated opsonization of the target cells into APCs (Hilchey et al. Blood 113 (16), 3809-3812 (2009)).

The discovery disclosed herein of a new mechanism of action for a bi-specific mAb may have particularly important implications for future therapy, as T cell infiltration in solid tumors is correlated with clinical responses. With its low molecular weight, bi-specific antibodies could penetrate into solid tumors to activate anergic or unresponsive T cells to kill tumor cells that express not only the known antigenic target of the bi-specific antibody, but also other undefined specific tumor antigens. The bi-specific antibody-mediated cytotoxic T cell clonal expansion for a variety of new epitopes should contribute greatly to its long-term therapeutic efficacy by preventing escape of cancer cell variants or low antigen density cells, as well as by promoting long-lived immunity. In addition, the vaccinal effect could be used for ex vivo expansion in advance of specific adoptive T cell therapy.

Although the foregoing invention has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims. All references cited herein are hereby incorporated in their entirety into the present application.

The invention claimed is:

1. A recombinant antibody comprising:
   (i) a first antigen-binding portion comprising:
   (A) a heavy chain (HC) variable region comprising HC-CDR1, HC-CDR2 and HC-CDR3, and a light chain (LC) variable region comprising LC-CDR1, LC-CDR2 and LC-CDR3, wherein:
   (1) the HC-CDR1, HC-CDR2 and HC-CDR3 comprises amino acid sequences set forth in SEQ ID NOs: 2, 3, and 4, respectively, and the LC-CDR1, LC-CDR2 and LC-CDR3 comprises amino acid sequences set forth in SEQ ID NOs: 8, 9, and 10, respectively;
   (2) the HC-CDR1, HC-CDR2 and HC-CDR3 comprises amino acid sequences set forth in SEQ ID NOs: 20, 21, and 22, respectively, and the LC-CDR1, LC-CDR2 and LC-CDR3 comprises amino acid sequences set forth in SEQ ID NOs: 26, 27, and 28, respectively;
   (3) the HC-CDR1, HC-CDR2 and HC-CDR3 comprises amino acid sequences set forth in SEQ ID NOs: 38, 39, and 40, respectively, and the LC-CDR1, LC-CDR2 and LC-CDR3 comprises amino acid sequences set forth in SEQ ID NOs: 44, 45, and 46, respectively;
   (4) the HC-CDR1, HC-CDR2 and HC-CDR3 comprises amino acid sequences set forth in SEQ ID NOs: 56, 57, and 58, respectively, and the LC-CDR1, LC-CDR2 and LC-CDR3 comprises amino acid sequences set forth in SEQ ID NOs: 62, 63, and 64, respectively;
   (5) the HC-CDR1, HC-CDR2 and HC-CDR3 comprises amino acid sequences set forth in SEQ ID NOs: 92, 93, and 94, respectively, and the LC-CDR1, LC-CDR2 and LC-CDR3 comprises amino acid sequences set forth in SEQ ID NOs: 80, 81, and 82, respectively; or
   (5) the HC-CDR1, HC-CDR2 and HC-CDR3 comprises amino acid sequences set forth in SEQ ID NOs: 74, 75, and 76, respectively, and the LC-CDR1, LC-CDR2 and LC-CDR3 comprises amino acid sequences set forth in SEQ ID NOs: 98, 99, and 100, respectively;

(B) a $V_H$ and a $V_L$ comprising first and second amino acid sequences as set forth in SEQ ID NOs: 14 and 16, 32 and 34, 50 and 52, 68 and 70, 86 and 88, or 104 and 106; or (C) an scFv comprising an amino acid sequence as set forth in SEQ ID NO: 18, 36, 54, 72, 90, or 108; and (ii) a second antigen-binding portion comprising an amino acid sequence set forth in SEQ ID NO: 111, 112, or 113.

2. The recombinant antibody of claim 1, wherein said first antigen-binding portion and/or said second antigen-binding portion is an antibody fragment selected from the group consisting of a Fab fragment; a monovalent fragment consisting of the VL, VH, CL and CH1 domains; a F(ab)2 fragment; a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment; an isolated CDR; and a scFv.

3. The recombinant antibody of claim 2, wherein said first antigen-binding portion and/or said second antigen-binding portion is a scFv.

4. The recombinant antibody of claim 1, wherein said first antigen-binding portion specifically binds to WT1/HLA and said second antigen-binding portion specifically binds to an immune effector cell surface antigen.

5. The recombinant antibody of claim 4, wherein said immune effector cell is selected from the group consisting natural killer (NK) cells, macrophages, and T cells.

6. The recombinant antibody of claim 4, wherein said immune effector cell is a $CD3^+$ cell and the recombinant antibody specifically binds to CD3.

7. The recombinant antibody of claim 1, comprising the amino acid sequence set forth in SEQ ID NO: 110.

8. A pharmaceutical composition comprising the recombinant antibody of claim 1.

* * * * *

SEQUENCE LISTING

<160> NUMBER OF SEQ ID NOS: 142

<210> SEQ ID NO 1
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1

Arg Met Phe Pro Asn Ala Pro Tyr Leu
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 2

Gly Gly Thr Phe Ser Ser Tyr Ala Ile Ser
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 3

Gly Ile Ile Pro Ile Phe Gly Thr Ala Asn Tyr Ala Gln Lys Phe Gln
1               5                   10                  15

Gly

<210> SEQ ID NO 4
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 4

Arg Ile Pro Pro Tyr Tyr Gly Met Asp Val
1               5                   10

<210> SEQ ID NO 5
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 5
ggaggcacct tcagcagcta tgctatcagc                                          30

<210> SEQ ID NO 6
<211> LENGTH: 51
<212> TYPE: DNA
<213> ORGANISM: Artificial Sequence
<220> FEATURE:

<223> OTHER INFORMATION: Synthetic Polynucleotide

<400> SEQUENCE: 6
gggatcatcc ctatctttgg tacagcaaac tacgcacaga agttccaggg c     51

<210> SEQ ID NO 7
<211> LENGTH: 30
<212> TYPE: DNA
<213> ORGANISM: Artificial Sequence
<220> FEATURE:
<223> OTHER INFORMATION: Synthetic Polynucleotidee

<400> SEQUENCE: 7
cggattcccc cgtactacgg tatggacgtc                             30

<210> SEQ ID NO 8
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 8

Ser Gly Ser Ser Ser Asn Ile Gly Ser Asn Tyr Val Tyr
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 9

Arg Ser Asn Gln Arg Pro Ser
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 10

Ala Ala Trp Asp Asp Ser Leu Asn Gly Val Val
1               5                   10

<210> SEQ ID NO 11
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 11
tctggaagca gctccaacat cggaagtaat tatgtatac                   39

<210> SEQ ID NO 12
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 12
aggagtaatc agcggccctc a                                               21

<210> SEQ ID NO 13
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 13
gcagcatggg atgacagcct gaatggtgtg gta                                  33

<210> SEQ ID NO 14
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ile Pro Pro Tyr Tyr Gly Met Asp Val Trp Gly Gln Gly
            100                 105                 110

Thr Thr Val Thr Val Ser Ser
        115

<210> SEQ ID NO 15
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 15
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagacggatt    300
cccccgtact acggtatgga cgtctggggc caagggacca cggtcaccgt ctcctca       357

<210> SEQ ID NO 16
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 16

```
Gln Thr Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Ser Asn Gln Arg Pro Ser Gly Val Pro Asp Arg Phe Ser
    50                  55                  60

Gly Ser Lys Ser Gly Thr Ser Ala Ser Leu Ala Ile Ser Gly Pro Arg
65                  70                  75                  80

Ser Val Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly
            100                 105                 110
```

<210> SEQ ID NO 17
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 17

```
cagactgtgg tgactcagcc accctcagcg tctgggaccc ccgggcagag ggtcaccatc     60
tcttgttctg gaagcagctc caacatcgga agtaattatg tatactggta ccaacagctc    120
ccaggaacgg cccccaaact cctcatctat aggagtaatc agcggccctc aggggtccct    180
gaccgattct ctggctccaa gtctggcacc tcagcctccc tggccatcag tgggccccgg    240
tccgtggatg aggctgatta ttactgtgca gcatgggatg acagcctgaa tggtgtggta    300
ttcggcggag ggaccaagct gaccgtccta ggt                                 333
```

<210> SEQ ID NO 18
<211> LENGTH: 250
<212> TYPE: PRT
<213> ORGANISM: Artificial Sequence
<220> FEATURE:
<223> OTHER INFORMATION: Synthetic Polypeptide

<400> SEQUENCE: 18

```
Gln Thr Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Ser Asn Gln Arg Pro Ser Gly Val Pro Asp Arg Phe Ser
    50                  55                  60

Gly Ser Lys Ser Gly Thr Ser Ala Ser Leu Ala Ile Ser Gly Pro Arg
65                  70                  75                  80

Ser Val Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Ser Leu
            115                 120                 125

Glu Met Ala Gln Val Gln Leu Val Gln Ser Gly Ala Glu Val Lys Lys
```

```
        130                 135                 140
Pro Gly Ser Ser Val Lys Val Ser Cys Lys Ala Ser Gly Thr Phe
145                 150                 155                 160

Ser Ser Tyr Ala Ile Ser Trp Val Arg Gln Ala Pro Gly Gln Gly Leu
                165                 170                 175

Glu Trp Met Gly Gly Ile Ile Pro Ile Phe Gly Thr Ala Asn Tyr Ala
            180                 185                 190

Gln Lys Phe Gln Gly Arg Val Thr Ile Thr Ala Asp Glu Ser Thr Ser
        195                 200                 205

Thr Ala Tyr Met Glu Leu Ser Ser Leu Arg Ser Glu Asp Thr Ala Val
    210                 215                 220

Tyr Tyr Cys Ala Arg Arg Ile Pro Pro Tyr Tyr Gly Met Asp Val Trp
225                 230                 235                 240

Gly Gln Gly Thr Thr Val Thr Val Ser Ser
                245                 250
```

<210> SEQ ID NO 19
<211> LENGTH: 750
<212> TYPE: DNA
<213> ORGANISM: Artificial Sequence
<220> FEATURE:
<223> OTHER INFORMATION: Synthetic Polynucleotide

<400> SEQUENCE: 19

```
cagactgtgg tgactcagcc accctcagcg tctgggaccc ccgggcagag ggtcaccatc      60
tcttgttctg gaagcagctc caacatcgga agtaattatg tatactggta ccaacagctc     120
ccaggaacgg cccccaaact cctcatctat aggagtaatc agcggccctc aggggtccct     180
gaccgattct ctggctccaa gtctggcacc tcagcctccc tggccatcag tgggccccgg     240
tccgtggatg aggctgatta ttactgtgca gcatgggatg acagcctgaa tggtgtggta     300
ttcggcggag ggaccaagct gaccgtccta ggttctagag gtggtggtgg tagcggcggc     360
ggcggctctg gtggtggatc cctcgagatg gcccaggtgc agctggtgca gtctggggct     420
gaggtgaaga agcctgggtc ctcggtgaag gtctcctgca aggcttctgg aggcaccttc     480
agcagctatg ctatcagctg ggtgcgacag gcccctggac aagggcttga gtggatggga     540
gggatcatcc ctatctttgg tacagcaaac tacgcacaga gttccaggg cagagtcacg      600
attaccgcgg acgaatccac gagcacagcc tacatggagc tgagcagcct gagatctgag     660
gacacggccg tgtattactg tgcgagacgg attcccccgt actacggtat ggacgtctgg     720
ggccaaggga ccacggtcac cgtctcctca                                      750
```

<210> SEQ ID NO 20
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 20

```
Gly Asp Ser Val Ser Ser Asn Ser Ala Ala Trp Asn
1               5                   10
```

<210> SEQ ID NO 21
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 21

Arg Thr Tyr Tyr Gly Ser Lys Trp Tyr Asn Asp Tyr Ala Val Ser Val
1               5                   10                  15
Lys Ser

<210> SEQ ID NO 22
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 22

Gly Arg Leu Gly Asp Ala Phe Asp Ile
1               5

<210> SEQ ID NO 23
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 23
ggggacagtg tctctagcaa cagtgctgct tggaac                                36

<210> SEQ ID NO 24
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 24
aggacatact acgggtccaa gtggtataat gattatgcag tatctgtgaa aagt            54

<210> SEQ ID NO 25
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 25
ggtcgcttag gggatgcttt tgatatc                                          27

<210> SEQ ID NO 26
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 26

Arg Ala Ser Gln Ser Ile Ser Ser Tyr Leu Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 27

Ala Ala Ser Ser Leu Gln Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 28

Gln Gln Ser Tyr Ser Thr Pro Leu Thr
1               5

<210> SEQ ID NO 29
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 29
cgggcaagtc agagcattag cagctattta aat                          33

<210> SEQ ID NO 30
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 30
gctgcatcca gtttgcaaag t                                       21

<210> SEQ ID NO 31
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 31
caacagagtt acagtacccc tctcact                                 27

<210> SEQ ID NO 32
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 32

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Gly Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val

```
                      85                  90                  95
Tyr Tyr Cys Ala Arg Gly Arg Leu Gly Asp Ala Phe Asp Ile Trp Gly
                100                 105                 110
Gln Gly Thr Met Val Thr Val Ser Ser
            115                 120

<210> SEQ ID NO 33
<211> LENGTH: 363
<212> TYPE: DNA
<213> ORGANISM: Artificial Sequence
<220> FEATURE:
<223> OTHER INFORMATION: Synthetic Polynucleotide

<400> SEQUENCE: 33
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg gaaggacat actacgggtc caagtggtat      180
aatgattatg cagtatctgt gaaaagtcga ataaccatca cccagacac atccaagaac      240 cagttctccc tgcagctgaa ctctgtgact cccgaggaca cggctgtgta ttactgtgca     300
agaggtcgct taggggatgc ttttgatatc tggggccaag gacaatggt caccgtctct     360 tca                                                                   363

<210> SEQ ID NO 34
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Asp Ile Lys Arg
            100                 105

<210> SEQ ID NO 35
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 35
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
```

```
aggttcagtg gcagtggatc tgggacagat ttcactctca ccatcagcag tctgcaacct    240
gaagattttg caacttacta ctgtcaacag agttacagta cccctctcac tttcggcgga    300
gggaccaaag tggatatcaa acgt                                          324
```

<210> SEQ ID NO 36
<211> LENGTH: 250
<212> TYPE: PRT
<213> ORGANISM: Artificial Sequence
<220> FEATURE:
<223> OTHER INFORMATION: Synthetic Polypeptide

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Asp Ile Lys Arg Ser Arg Gly Gly
            100                 105                 110

Gly Gly Ser Gly Gly Gly Gly Ser Gly Gly Gly Gly Ser Leu Glu Met
        115                 120                 125

Ala Gln Val Gln Leu Gln Gln Ser Gly Pro Gly Leu Val Lys Pro Ser
    130                 135                 140

Gln Thr Leu Ser Leu Thr Cys Ala Ile Ser Gly Asp Ser Val Ser Ser
145                 150                 155                 160

Asn Ser Ala Ala Trp Asn Trp Ile Arg Gln Ser Pro Ser Arg Gly Leu
                165                 170                 175

Glu Trp Leu Gly Arg Thr Tyr Tyr Gly Ser Lys Trp Tyr Asn Asp Tyr
            180                 185                 190

Ala Val Ser Val Lys Ser Arg Ile Thr Ile Asn Pro Asp Thr Ser Lys
        195                 200                 205

Asn Gln Phe Ser Leu Gln Leu Asn Ser Val Thr Pro Glu Asp Thr Ala
    210                 215                 220

Val Tyr Tyr Cys Ala Arg Gly Arg Leu Gly Asp Ala Phe Asp Ile Trp
225                 230                 235                 240

Gly Gln Gly Thr Met Val Thr Val Ser Ser
                245                 250
```

<210> SEQ ID NO 37
<211> LENGTH: 750
<212> TYPE: DNA
<213> ORGANISM: Artificial Sequence
<220> FEATURE:
<223> OTHER INFORMATION: Synthetic Polynucleotide

<400> SEQUENCE: 37

```
gacatccaga tgacccagtc tccatcctcc ctgtctgcat ctgtaggaga cagagtcacc    60
atcacttgcc gggcaagtca gagcattagc agctatttaa attggtatca gcagaaacca    120
gggaaagccc ctaagctcct gatctatgct gcatccagtt tgcaaagtgg ggtcccatca    180
```

```
aggttcagtg gcagtggatc tgggacagat ttcactctca ccatcagcag tctgcaacct    240
gaagattttg caacttacta ctgtcaacag agttacagta cccctctcac tttcggcgga    300
gggaccaaag tggatatcaa cgttctaga ggtggtggtg gtagcggcgg cggcggctct     360
ggtggtggtg gatccctcga gatggcccag gtacagctgc agcagtcagg tccaggactg    420
gtgaagccct cgcagaccct ctcactcacc tgtgccatct ccggggacag tgtctctagc    480
aacagtgctg cttggaactg gatcaggcag tccccatcga gaggccttga gtggctggga    540
aggacatact acgggtccaa gtggtataat gattatgcag tatctgtgaa aagtcgaata    600
accatcaacc cagacacatc caagaaccag ttctccctgc agctgaactc tgtgactccc    660
gaggacacgg ctgtgtatta ctgtgcaaga ggtcgcttag gggatgcttt tgatatctgg    720
ggccaaggga caatggtcac cgtctcttca                                     750
```

<210> SEQ ID NO 38
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 38

Gly Tyr Ser Phe Thr Asn Phe Trp Ile Ser
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 39

Arg Val Asp Pro Gly Tyr Ser Tyr Ser Thr Tyr Ser Pro Ser Phe Gln
1               5                   10                  15
Gly

<210> SEQ ID NO 40
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 40

Val Gln Tyr Ser Gly Tyr Tyr Asp Trp Phe Asp Pro
1               5                   10

<210> SEQ ID NO 41
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 41
ggatacagct tcaccaactt ctggatcagc                                     30

<210> SEQ ID NO 42
<211> LENGTH: 51
<212> TYPE: DNA
<213> ORGANISM: Artificial Sequence

```
<220> FEATURE:
<223> OTHER INFORMATION: Synthetic Polynucleotide

<400> SEQUENCE: 42
agggttgatc ctggctactc ttatagcacc tacagcccgt ccttccaagg c          51

<210> SEQ ID NO 43
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 43
gtacaatata gtggctacta tgactggttc gacccc                           36

<210> SEQ ID NO 44
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 44

Ser Gly Ser Ser Ser Asn Ile Gly Ser Asn Thr Val Asn
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 45

Ser Asn Asn Gln Arg Pro Ser
1               5

<210> SEQ ID NO 46
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 46

Ala Ala Trp Asp Asp Ser Leu Asn Gly Trp Val
1               5                   10

<210> SEQ ID NO 47
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 47
tctggaagca gctccaacat cggaagtaat actgtaaac                        39

<210> SEQ ID NO 48
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 48
```
agtaataatc agcggccctc a                                              21

<210> SEQ ID NO 49
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 49
gcagcatggg atgacagcct gaatggttgg gtg                                 33

<210> SEQ ID NO 50
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 50

Gln Met Gln Leu Val Gln Ser Gly Ala Glu Val Lys Glu Pro Gly Glu
1               5                   10                  15

Ser Leu Arg Ile Ser Cys Lys Gly Ser Gly Tyr Ser Phe Thr Asn Phe
            20                  25                  30

Trp Ile Ser Trp Val Arg Gln Met Pro Gly Lys Gly Leu Glu Trp Met
        35                  40                  45

Gly Arg Val Asp Pro Gly Tyr Ser Tyr Ser Thr Tyr Ser Pro Ser Phe
    50                  55                  60

Gln Gly His Val Thr Ile Ser Ala Asp Lys Ser Thr Ser Thr Ala Tyr
65                  70                  75                  80

Leu Gln Trp Asn Ser Leu Lys Ala Ser Asp Thr Ala Met Tyr Tyr Cys
                85                  90                  95

Ala Arg Val Gln Tyr Ser Gly Tyr Tyr Asp Trp Phe Asp Pro Trp Gly
            100                 105                 110

Gln Gly Thr Leu Val Thr Val Ser Ser
        115                 120

<210> SEQ ID NO 51
<211> LENGTH: 363
<212> TYPE: DNA
<213> ORGANISM: Artificial Sequence
<220> FEATURE:
<223> OTHER INFORMATION: Synthetic Polynucleotide

<400> SEQUENCE: 51
cagatgcagc tggtgcagtc cggagcagag gtgaaagagc ccggggagtc tctgaggatc    60
tcctgtaagg gttctggata cagcttcacc aacttctgga tcagctgggt gcgccagatg   120
cccgggaaag gcctggagtg gatggggagg gttgatcctg gctactctta tagcacctac   180
agcccgtcct tccaaggcca cgtcaccatc tcagctgaca gtctaccag cactgcctac    240 ctgcagtgga acagcctgaa ggcctcggac accgccatgt attactgtgc gagagtacaa   300
tatagtggct actatgactg gttcgacccc tggggccagg gaaccctggt caccgtctcc   360
tca                                                                 363

<210> SEQ ID NO 52
<211> LENGTH: 111
<212> TYPE: PRT
<213> ORGANISM: Artificial Sequence
<220> FEATURE:

<223> OTHER INFORMATION: Synthetic Polypeptide

<400> SEQUENCE: 52

```
Gln Ala Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly
            100                 105                 110
```

<210> SEQ ID NO 53
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 53

```
caggctgtgg tgactcagcc accctcagcg tctgggaccc ccggggcagag ggtcaccatc    60
tcttgttctg gaagcagctc caacatcgga agtaatactg taaactggta ccagcaggtc   120
ccaggaacgg cccccaaact cctcatctat agtaataatc agcggccctc agggtccct    180
gaccgattct ctggctccaa gtctggcacc tcagcctccc tggccatcag tgggctccag   240
tctgaggatg aggctgatta ttactgtgca gcatgggatg acagcctgaa tggttgggtg   300
ttcggcggag ggaccaagct gaccgtccta ggt                                333
```

<210> SEQ ID NO 54
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 54

```
Gln Ala Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
```

115                 120                 125
Leu Glu Met Ala Gln Met Gln Leu Val Gln Ser Gly Ala Glu Val Lys
        130                 135                 140

Glu Pro Gly Glu Ser Leu Arg Ile Ser Cys Lys Gly Ser Gly Tyr Ser
145                 150                 155                 160

Phe Thr Asn Phe Trp Ile Ser Trp Val Arg Gln Met Pro Gly Lys Gly
                165                 170                 175

Leu Glu Trp Met Gly Arg Val Asp Pro Gly Tyr Ser Tyr Ser Thr Tyr
            180                 185                 190

Ser Pro Ser Phe Gln Gly His Val Thr Ile Ser Ala Asp Lys Ser Thr
        195                 200                 205

Ser Thr Ala Tyr Leu Gln Trp Asn Ser Leu Lys Ala Ser Asp Thr Ala
    210                 215                 220

Met Tyr Tyr Cys Ala Arg Val Gln Tyr Ser Gly Tyr Tyr Asp Trp Phe
225                 230                 235                 240

Asp Pro Trp Gly Gln Gly Thr Leu Val Thr Val Ser Ser
                245                 250

<210> SEQ ID NO 55
<211> LENGTH: 759
<212> TYPE: DNA
<213> ORGANISM: Artificial Sequence
<220> FEATURE:
<223> OTHER INFORMATION: Synthetic Polynucleotide

<400> SEQUENCE: 55
caggctgtgg tgactcagcc accctcagcg tctgggaccc ccgggcagag ggtcaccatc      60
tcttgttctg gaagcagctc aacatcgga agtaatactg taaactggta ccagcaggtc     120
ccaggaacgg cccccaaact cctcatctat agtaataatc agcggccctc aggggtccct     180
gaccgattct ctggctccaa gtctggcacc tcagcctccc tggccatcag tgggctccag     240
tctgaggatg aggctgatta ttactgtgca gcatgggatg acagcctgaa tggttgggtg     300
ttcggcggag ggaccaagct gaccgtccta ggttctagag gtggtggtgg tagcggcggc     360
ggcggctctg gtggtggtgg atccctcgag atggcccaga tgcagctggt gcagtccgga     420
gcagaggtga aagagcccgg ggagtctctg aggatctcct gtaagggttc tggatacagc     480
ttcaccaact ctggatcag ctgggtgcgc cagatgcccg ggaaaggcct ggagtggatg     540
gggagggttg atcctggcta ctcttatagc acctacagcc cgtccttcca aggccacgtc     600
accatctcag ctgacaagtc taccagcact gcctacctgc agtggaacag cctgaaggcc     660
tcggacaccg ccatgtatta ctgtgcgaga gtacaatata gtggctacta tgactggttc     720 gaccctggg gccagggaac cctggtcacc gtctcctca                             759

<210> SEQ ID NO 56
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 56

Gly Tyr Asn Phe Ser Asn Lys Trp Ile Gly
1               5                   10

<210> SEQ ID NO 57
<211> LENGTH: 17
<212> TYPE: PRT

```
<213> ORGANISM: Artificial Sequence
<220> FEATURE:
<223> OTHER INFORMATION: Synthetic Polypeptide

<400> SEQUENCE: 57

Ile Ile Tyr Pro Gly Tyr Ser Asp Ile Thr Tyr Ser Pro Ser Phe Gln
1               5                   10                  15

Gly

<210> SEQ ID NO 58
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 58

His Thr Ala Leu Ala Gly Phe Asp Tyr
1               5

<210> SEQ ID NO 59
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 59
ggctacaact ttagcaacaa gtggatcggc                                    30

<210> SEQ ID NO 60
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 60
atcatctatc ccggttactc ggacatcacc tacagcccgt ccttccaagg c             51

<210> SEQ ID NO 61
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 61
cacacagctt tggccggctt tgactac                                       27

<210> SEQ ID NO 62
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 62

Arg Ala Ser Gln Asn Ile Asn Lys Trp Leu Ala
1               5                   10

<210> SEQ ID NO 63
<211> LENGTH: 7
<212> TYPE: PRT
<213> ORGANISM: Artificial Sequence
<220> FEATURE:
```

<223> OTHER INFORMATION: Synthetic Polypeptide

<400> SEQUENCE: 63

Lys Ala Ser Ser Leu Glu Ser
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 64

Gln Gln Tyr Asn Ser Tyr Ala Thr
1               5

<210> SEQ ID NO 65
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 65
cgggccagtc agaatatcaa taagtggctg gcc                                  33

<210> SEQ ID NO 66
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 66
aaggcgtcta gtttagaaag t                                               21

<210> SEQ ID NO 67
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 67
caacaatata atagttatgc gacg                                            24

<210> SEQ ID NO 68
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 68

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Ser Asn Lys
            20                  25                  30

Trp Ile Gly Trp Val Arg Gln Leu Pro Gly Arg Gly Leu Glu Trp Ile
        35                  40                  45

Ala Ile Ile Tyr Pro Gly Tyr Ser Asp Ile Thr Tyr Ser Pro Ser Phe
    50                  55                  60

Gln Gly Arg Val Thr Ile Ser Ala Asp Thr Ser Ile Asn Thr Ala Tyr

```
                65                  70                  75                  80
Leu His Trp His Ser Leu Lys Ala Ser Asp Thr Ala Met Tyr Tyr Cys
                        85                  90                  95

Val Arg His Thr Ala Leu Ala Gly Phe Asp Tyr Trp Gly Leu Gly Thr
                100                 105                 110

Leu Val Thr Val Ser Ser
            115
```

<210> SEQ ID NO 69
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 69

```
caggtgcagc tggtgcagtc tggagcagag gtgaaaaagc ccggagagtc tctgaagatc      60
tcctgtaagg gttctggcta caactttagc aacaagtgga tcggctgggt gcgccaattg     120
cccgggagag gcctggagtg gatagcaatc atctatcccg gttactcgga catcacctac     180
agcccgtcct tccaaggccg cgtcaccatc tccgccgaca cgtccattaa caccgcctac     240
ctgcactggc acagcctgaa ggcctcggac accgccatgt attattgtgt gcgacacaca     300
gctttggccg gctttgacta ctggggcctg gcaccctgg tcaccgtctc ctca            354
```

<210> SEQ ID NO 70
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 70

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Asn Lys Trp
            20                  25                  30

Leu Ala Trp Tyr Gln Gln Arg Pro Gly Lys Ala Pro Gln Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Tyr Asn Ser Tyr Ala Thr
                85                  90                  95

Phe Gly Gln Gly Thr Lys Val Glu Ile Lys Arg
            100                 105
```

<210> SEQ ID NO 71
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 71

```
gacatccaga tgacccagtc tccttccacc ctgtctgcat ctgtaggaga cagagtcaca      60
atcacttgcc gggccagtca gaatatcaat aagtggctgg cctggtatca gcagagacca     120
gggaaagccc ctcagctcct gatctataag gcgtctagtt tagaaagtgg ggtcccatct     180
```

```
aggttcagcg gcagtggatc tgggacagaa tacactctca ccatcagcag cctgcagcct    240
gatgattttg caacttatta ctgccaacaa tataatagtt atgcgacgtt cggccaaggg    300
accaaggtgg aaatcaaacg t                                              321
```

<210> SEQ ID NO 72  
<211> LENGTH: 246  
<212> TYPE: PRT  
<213> ORGANISM: Artificial Sequence  
<220> FEATURE:  
<223> OTHER INFORMATION: Synthetic Polypeptide

<400> SEQUENCE: 72

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Asn Lys Trp
            20                  25                  30

Leu Ala Trp Tyr Gln Gln Arg Pro Gly Lys Ala Pro Gln Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Tyr Asn Ser Tyr Ala Thr
                85                  90                  95

Phe Gly Gln Gly Thr Lys Val Glu Ile Lys Arg Ser Arg Gly Gly Gly
            100                 105                 110

Gly Ser Gly Gly Gly Ser Gly Gly Gly Ser Leu Glu Met Ala
        115                 120                 125

Gln Val Gln Leu Val Gln Ser Gly Ala Glu Val Lys Lys Pro Gly Glu
    130                 135                 140

Ser Leu Lys Ile Ser Cys Lys Gly Ser Gly Tyr Asn Phe Ser Asn Lys
145                 150                 155                 160

Trp Ile Gly Trp Val Arg Gln Leu Pro Gly Arg Gly Leu Glu Trp Ile
                165                 170                 175

Ala Ile Ile Tyr Pro Gly Tyr Ser Asp Ile Thr Tyr Ser Pro Ser Phe
            180                 185                 190

Gln Gly Arg Val Thr Ile Ser Ala Asp Thr Ser Ile Asn Thr Ala Tyr
        195                 200                 205

Leu His Trp His Ser Leu Lys Ala Ser Asp Thr Ala Met Tyr Tyr Cys
    210                 215                 220

Val Arg His Thr Ala Leu Ala Gly Phe Asp Tyr Trp Gly Leu Gly Thr
225                 230                 235                 240

Leu Val Thr Val Ser Ser
                245
```

<210> SEQ ID NO 73  
<211> LENGTH: 738  
<212> TYPE: DNA  
<213> ORGANISM: Artificial Sequence  
<220> FEATURE:  
<223> OTHER INFORMATION: Synthetic Polynucleotide

<400> SEQUENCE: 73

```
gacatccaga tgacccagtc tccttccacc ctgtctgcat ctgtaggaga cagagtcaca    60
atcacttgcc gggccagtca gaatatcaat aagtggctgg cctggtatca gcagagacca   120
```

```
gggaaagccc ctcagctcct gatctataag gcgtctagtt tagaaagtgg ggtcccatct    180
aggttcagcg gcagtggatc tgggacagaa tacactctca ccatcagcag cctgcagcct    240
gatgattttg caacttatta ctgccaacaa tataatagtt atgcgacgtt cggccaaggg    300
accaaggtgg aaatcaaacg ttctagaggt ggtggtggta gcggcggcgg cggctctggt    360
ggtggtggat ccctcgagat ggcccaggtg cagctggtgc agtctggagc agaggtgaaa    420
aagcccggag agtctctgaa gatctcctgt aagggttctg gctacaactt tagcaacaag    480
tggatcggct gggtgcgcca attgcccggg agaggcctgg agtggatagc aatcatctat    540
cccggttact cggacatcac ctacagcccg tccttccaag gccgcgtcac catctccgcc    600
gacacgtcca ttaacaccgc ctacctgcac tggcacagcc tgaaggcctc ggacaccgcc    660
atgtattatt gtgtgcgaca cacagctttg gccggctttg actactgggg cctgggcacc    720
ctggtcaccg tctcctca                                                  738
```

```
<210> SEQ ID NO 74
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 74
```

Gly Phe Thr Phe Asp Asp Tyr Gly Met Ser
1               5                   10

```
<210> SEQ ID NO 75
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 75
```

Gly Ile Asn Trp Asn Gly Gly Ser Thr Gly Tyr Ala Asp Ser Val Arg
1               5                   10                  15

Gly

```
<210> SEQ ID NO 76
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 76
```

Glu Arg Gly Tyr Gly Tyr His Asp Pro His Asp Tyr
1               5                   10

```
<210> SEQ ID NO 77
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 77
```

```
gggttcacct ttgatgatta tggcatgagc                                     30
```

```
<210> SEQ ID NO 78
<211> LENGTH: 51
<212> TYPE: DNA
```

<213> ORGANISM: Artificial Sequence
<220> FEATURE:
<223> OTHER INFORMATION: Synthetic Polynucleotide

<400> SEQUENCE: 78
ggtattaatt ggaatggtgg tagcacaggt tatgcagact ctgtgagggg c      51

<210> SEQ ID NO 79
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 79
gagcgtggct acgggtacca tgatccccat gactac      36

<210> SEQ ID NO 80
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 80

Gly Arg Asn Asn Ile Gly Ser Lys Ser Val His
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 81

Asp Asp Ser Asp Arg Pro Ser
1               5

<210> SEQ ID NO 82
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 82

Gln Val Trp Asp Ser Ser Ser Asp His Val Val
1               5                   10

<210> SEQ ID NO 83
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 83
gggagaaaca acattggaag taaaagtgtg cac      33

<210> SEQ ID NO 84
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 84
gatgatagcg accggccctc a                                              21

<210> SEQ ID NO 85
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 85
caggtgtggg atagtagtag tgatcatgtg gta                                 33

<210> SEQ ID NO 86
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 86

Glu Val Gln Leu Val Gln Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Glu Arg Gly Tyr Gly Tyr His Asp Pro His Asp Tyr Trp Gly
            100                 105                 110

Gln Gly Thr Leu Val Thr Val Ser Ser
        115                 120

<210> SEQ ID NO 87
<211> LENGTH: 363
<212> TYPE: DNA
<213> ORGANISM: Artificial Sequence
<220> FEATURE:
<223> OTHER INFORMATION: Synthetic Polynucleotide

<400> SEQUENCE: 87
gaagtgcagc tggtgcagtc tggggggaggt gtggtacggc ctggggggtc cctgagactc    60
tcctgtgcag cctctgggtt caccttttgat gattatggca tgagctgggt ccgccaagct   120
ccagggaagg ggctggagtg ggtctctggt attaattgga atggtggtag cacaggttat   180
gcagactctg tgaggggccg attcaccatc tccagagaca acgccaagaa ctccctgtat   240
ctgcaaatga acagtctgag agccgaggac acggccttgt attactgtgc gagagagcgt   300
ggctacgggt accatgatcc ccatgactac tggggccaag caccctggt gaccgtctcc    360 tca                                                                  363

<210> SEQ ID NO 88
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 88

Gln Ser Val Val Thr Gln Pro Pro Ser Val Ser Val Ala Pro Gly Lys
1               5                   10                  15

Thr Ala Arg Ile Thr Cys Gly Arg Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Val Val Phe Gly Gly Gly Thr Lys Leu Thr Val Leu Gly
            100                 105

<210> SEQ ID NO 89
<211> LENGTH: 327
<212> TYPE: DNA
<213> ORGANISM: Artificial Sequence
<220> FEATURE:
<223> OTHER INFORMATION: Synthetic Polypeptide

<400> SEQUENCE: 89
cagtctgtcg tgacgcagcc gccctcggtg tcagtggccc caggaaagac ggccaggatt      60
acctgtggga gaaacaacat tggaagtaaa agtgtgcact ggtaccagca gaagccaggc     120
caggcccctg tgctggtcgt ctatgatgat agcgaccggc cctcaggat ccctgagcga      180
ttctctggct ccaactctgg gaacacggcc accctgacca tcagcagggt cgaagccggg     240
gatgaggccg actattactg tcaggtgtgg gatagtagta gtgatcatgt ggtattcggc     300
ggagggacca agctgaccgt cctaggt                                         327

<210> SEQ ID NO 90
<211> LENGTH: 249
<212> TYPE: PRT
<213> ORGANISM: Artificial Sequence
<220> FEATURE:
<223> OTHER INFORMATION: Synthetic Polypeptide

<400> SEQUENCE: 90

Gln Ser Val Val Thr Gln Pro Pro Ser Val Ser Val Ala Pro Gly Lys
1               5                   10                  15

Thr Ala Arg Ile Thr Cys Gly Arg Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Ser Arg Gly
            100                 105                 110

Gly Gly Gly Ser Gly Gly Gly Ser Gly Gly Ser Leu Glu Met Ala
            115                 120                 125

Glu Val Gln Leu Val Gln Ser Gly Gly Val Val Arg Pro Gly Gly
    130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Arg Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Leu Tyr Tyr Cys
    210                 215                 220

Ala Arg Glu Arg Gly Tyr Gly Tyr His Asp Pro His Asp Tyr Trp Gly
225                 230                 235                 240

Gln Gly Thr Leu Val Thr Val Ser Ser
                245

<210> SEQ ID NO 91
<211> LENGTH: 747
<212> TYPE: DNA
<213> ORGANISM: Artificial Sequence
<220> FEATURE:
<223> OTHER INFORMATION: Synthetic Polynucleotide

<400> SEQUENCE: 91
cagtctgtcg tgacgcagcc gccctcggtg tcagtggccc caggaaagac ggccaggatt      60
acctgtggga gaaacaacat tggaagtaaa agtgtgcact ggtaccagca gaagccaggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgatcatgt ggtattcggc     300
ggagggacca agctgaccgt cctaggttct agaggtggtg gtggtagcgg cggcggcggc     360
tctggtggat ccctcgagat ggccgaagtg cagctggtgc agtctggggg aggtgtggta     420
cggcctgggg gatccctgag actctcctgt gcagcctctg gattcacctt tgatgattat     480
ggcatgagct gggtccgcca agctccaggg aaggggctgg agtgggtctc tggtattaat     540
tggaatggtg gtagcacagg ttatgcagac tctgtgaggg gccgattcac catctccaga     600
gacaacgcca agaactccct gtatctgcaa atgaacagtc tgagagccga ggacacggcc     660
ttgtattact gtgcgagaga gcgtggctac gggtaccatg atccccatga ctactggggc     720
caaggcaccc tggtgaccgt ctcctca                                          747

<210> SEQ ID NO 92
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 92

Gly Phe Ser Val Ser Gly Thr Tyr Met Gly
1               5                   10

<210> SEQ ID NO 93
<211> LENGTH: 16

```
<212> TYPE: PRT
<213> ORGANISM: Artificial Sequence
<220> FEATURE:
<223> OTHER INFORMATION: Synthetic Polypeptide

<400> SEQUENCE: 93

Leu Leu Tyr Ser Gly Gly Gly Thr Tyr His Pro Ala Ser Leu Gln Gly
1               5                   10                  15

<210> SEQ ID NO 94
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 94

Gly Gly Ala Gly Gly Gly His Phe Asp Ser
1               5                   10

<210> SEQ ID NO 95
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 95
gggttctccg tcagtggcac ctacatgggc                                    30

<210> SEQ ID NO 96
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 96
cttctttata gtggtggcgg cacataccac ccagcgtccc tgcagggc                 48

<210> SEQ ID NO 97
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 97 gagggcagg aggtggccac tttgactcc                                      29

<210> SEQ ID NO 98
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 98

Thr Gly Ser Ser Ser Asn Ile Gly Ala Gly Tyr Asp Val His
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Synthetic Polypeptide
```

<400> SEQUENCE: 99

Gly Asn Ser Asn Arg Pro Ser
1               5

<210> SEQ ID NO 100
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 100

Ala Ala Trp Asp Asp Ser Leu Asn Gly Tyr Val
1               5                   10

<210> SEQ ID NO 101
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 101
actgggagca gctccaacat cggggcaggt tatgatgtac ac                          42

<210> SEQ ID NO 102
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 102
ggtaacagca atcggccctc a                                                 21

<210> SEQ ID NO 103
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 103
gcagcatggg atgacagcct gaatggttat gtc                                    33

<210> SEQ ID NO 104
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 104

Glu Val Gln Leu Val Glu Thr Gly Gly Gly Leu Leu Gln Pro Gly Gly
1               5                   10                  15

Ser Leu Arg Leu Ser Cys Ala Ala Ser Gly Phe Ser Val Ser Gly Thr
            20                  25                  30

Tyr Met Gly Trp Val Arg Gln Ala Pro Gly Lys Gly Leu Glu Trp Val
        35                  40                  45

Ala Leu Leu Tyr Ser Gly Gly Gly Thr Tyr His Pro Ala Ser Leu Gln
    50                  55                  60

Gly Arg Phe Ile Val Ser Arg Asp Ser Ser Lys Asn Met Val Tyr Leu
65                  70                  75                  80

Gln Met Asn Ser Leu Lys Ala Glu Asp Thr Ala Val Tyr Tyr Cys Ala
                85                  90                  95

Lys Gly Gly Ala Gly Gly Gly His Phe Asp Ser Trp Gly Gln Gly Thr
            100                 105                 110

Leu Val Thr Val Ser Ser
        115

<210> SEQ ID NO 105
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 105
gaggtgcagc tggtggagac cggaggaggc ttgctccagc cggggggtc cctcagactc      60 tcctgtgcag cctctgggtt ctccgtcagt ggcacctaca tgggctgggt ccgccaggct    120
ccagggaagg gactggagtg gtcgcacttc tttatagtg gtggcggcac ataccaccca     180
gcgtccctgc agggccgatt catcgtctcc agagacagct ccaagaatat ggtctatctt    240
caaatgaata gcctgaaagc cgaggacacg gccgtctatt actgtgcgaa aggaggggca    300
ggaggtggcc actttgactc ctggggccaa ggcaccctgg tgaccgtctc ctca          354

<210> SEQ ID NO 106
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 106

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Asn Gly Tyr Val Phe Gly Thr Gly Thr Lys Leu Thr Val Leu Gly
            100                 105                 110

<210> SEQ ID NO 107
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 107
cagtctgtgt tgacgcagcc gccctcagtg tctggggccc cagggcagag ggtcaccatc      60
tcctgcactg ggagcagctc caacatcggg gcaggttatg atgtacactg gtaccagcag    120
cttccaggaa cagccccaa actcctcatc tatggtaaca gcaatcggcc ctcaggggtc      180
cctgaccgat tctctggctc caagtctggc acctcagcct ccctggccat cagtgggctc 240
cagtctgagg atgaggctga ttattactgt gcagcatggg atgacagcct gaatggttat 300
gtcttcggaa ctgggaccaa gctgaccgtc ctaggt 336

<210> SEQ ID NO 108
<211> LENGTH: 251
<212> TYPE: PRT
<213> ORGANISM: Artificial Sequence
<220> FEATURE:
<223> OTHER INFORMATION: Synthetic Polypeptide

<400> SEQUENCE: 108

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Asn Gly Tyr Val Phe Gly Thr Gly Thr Lys Leu Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Glu Thr Gly Gly Gly Leu
    130                 135                 140

Leu Gln Pro Gly Gly Ser Leu Arg Leu Ser Cys Ala Ala Ser Gly Phe
145                 150                 155                 160

Ser Val Ser Gly Thr Tyr Met Gly Trp Val Arg Gln Ala Pro Gly Lys
                165                 170                 175

Gly Leu Glu Trp Val Ala Leu Leu Tyr Ser Gly Gly Thr Tyr His
            180                 185                 190

Pro Ala Ser Leu Gln Gly Arg Phe Ile Val Ser Arg Asp Ser Ser Lys
        195                 200                 205

Asn Met Val Tyr Leu Gln Met Asn Ser Leu Lys Ala Glu Asp Thr Ala
    210                 215                 220

Val Tyr Tyr Cys Ala Lys Gly Gly Ala Gly Gly His Phe Asp Ser
225                 230                 235                 240

Trp Gly Gln Gly Thr Leu Val Thr Val Ser Ser
                245                 250

<210> SEQ ID NO 109
<211> LENGTH: 753
<212> TYPE: DNA
<213> ORGANISM: Artificial Sequence
<220> FEATURE:
<223> OTHER INFORMATION: Synthetic Polynucleotide

<400> SEQUENCE: 109
cagtctgtgt tgacgcagcc gccctcagtg tctggggccc cagggcagag ggtcaccatc 60
tcctgcactg ggagcagctc caacatcggg gcaggttatg atgtacactg gtaccagcag 120
cttccaggaa cagccccaa actcctcatc tatggtaaca gcaatcggcc ctcaggggtc 180

-continued

```
cctgaccgat tctctggctc caagtctggc acctcagcct ccctggccat cagtgggctc      240
cagtctgagg atgaggctga ttattactgt gcagcatggg atgacagcct gaatggttat      300
gtcttcggaa ctgggaccaa gctgaccgtc ctaggttcta gaggtggtgg tggtagcggc      360
ggcggcggct ctggtggtgg tggatccctc gagatggccg aggtgcagct ggtggagacc      420
ggaggaggct tgctccagcc ggggggtcc ctcagactct cctgtgcagc ctctgggttc       480
tccgtcagtg gcacctacat gggctgggtc cgccaggctc agggaaggg actggagtgg       540 gtcgcacttc tttatagtgg tggcggcaca taccacccag cgtccctgca gggccgattc      600
atcgtctcca gagacagctc caagaatatg gtctatcttc aaatgaatag cctgaaagcc      660
gaggacacgg ccgtctatta ctgtgcgaaa ggagggcag gaggtggcca ctttgactcc       720
tggggccaag gcaccctggt gaccgtctcc tca                                    753
```

<210> SEQ ID NO 110
<211> LENGTH: 523
<212> TYPE: PRT
<213> ORGANISM: Artificial Sequence
<220> FEATURE:
<223> OTHER INFORMATION: Synthetic Polypeptide

<400> SEQUENCE: 110

```
Met Gly Trp Ser Cys Ile Ile Leu Phe Leu Val Ala Thr Ala Thr Gly
1               5                   10                  15

Gln Ala Val Val Thr Gln Pro Pro Ser Ala Ser Gly Thr Pro Gly Gln
            20                  25                  30

Arg Val Thr Ile Ser Cys Ser Gly Ser Ser Ser Asn Ile Gly Ser Asn
        35                  40                  45

Thr Val Asn Trp Tyr Gln Gln Val Pro Gly Thr Ala Pro Lys Leu Leu
    50                  55                  60

Ile Tyr Ser Asn Asn Gln Arg Pro Ser Gly Val Pro Asp Arg Phe Ser
65                  70                  75                  80

Gly Ser Lys Ser Gly Thr Ser Ala Ser Leu Ala Ile Ser Gly Leu Gln
                85                  90                  95

Ser Glu Asp Glu Ala Asp Tyr Tyr Cys Ala Ala Trp Asp Asp Ser Leu
            100                 105                 110

Asn Gly Trp Val Phe Gly Gly Gly Thr Lys Leu Thr Val Leu Gly Ser
        115                 120                 125

Arg Gly Gly Gly Ser Gly Gly Gly Ser Gly Gly Gly Gly Ser
    130                 135                 140

Leu Glu Met Ala Gln Met Gln Leu Val Gln Ser Gly Ala Glu Val Lys
145                 150                 155                 160

Glu Pro Gly Glu Ser Leu Arg Ile Ser Cys Lys Gly Ser Gly Tyr Ser
                165                 170                 175

Phe Thr Asn Phe Trp Ile Ser Trp Val Arg Gln Met Pro Gly Lys Gly
            180                 185                 190

Leu Glu Trp Met Gly Arg Val Asp Pro Gly Tyr Ser Tyr Ser Thr Tyr
        195                 200                 205

Ser Pro Ser Phe Gln Gly His Val Thr Ile Ser Ala Asp Lys Ser Thr
    210                 215                 220

Ser Thr Ala Tyr Leu Gln Trp Asn Ser Leu Lys Ala Ser Asp Thr Ala
225                 230                 235                 240

Met Tyr Tyr Cys Ala Arg Val Gln Tyr Ser Gly Tyr Tyr Asp Trp Phe
                245                 250                 255
```

Asp Pro Trp Gly Gln Gly Thr Leu Val Thr Val Ser Ser Gly Gly Gly
            260                 265                 270

Gly Ser Asp Val Gln Leu Val Gln Ser Gly Ala Glu Val Lys Lys Pro
        275                 280                 285

Gly Ala Ser Val Lys Val Ser Cys Lys Ala Ser Gly Tyr Thr Phe Thr
    290                 295                 300

Arg Tyr Thr Met His Trp Val Arg Gln Ala Pro Gly Gln Gly Leu Glu
305                 310                 315                 320

Trp Ile Gly Tyr Ile Asn Pro Ser Arg Gly Tyr Thr Asn Tyr Ala Asp
                325                 330                 335

Ser Val Lys Gly Arg Phe Thr Ile Thr Thr Asp Lys Ser Thr Ser Thr
            340                 345                 350

Ala Tyr Met Glu Leu Ser Ser Leu Arg Ser Glu Asp Thr Ala Thr Tyr
        355                 360                 365

Tyr Cys Ala Arg Tyr Tyr Asp Asp His Tyr Cys Leu Asp Tyr Trp Gly
    370                 375                 380

Gln Gly Thr Thr Val Thr Val Ser Ser Gly Gly Gly Ser Thr Gly
385                 390                 395                 400

Ser Gly Gly Ser Gly Gly Ser Gly Ala Asp Asp Ile Val Leu Thr
            405                 410                 415

Gln Ser Pro Ala Thr Leu Ser Leu Ser Pro Gly Glu Arg Ala Thr Leu
        420                 425                 430

Ser Cys Arg Ala Ser Gln Ser Val Ser Tyr Met Asn Trp Tyr Gln Gln
    435                 440                 445

Lys Pro Gly Lys Ala Pro Lys Arg Trp Ile Tyr Asp Thr Ser Lys Val
450                 455                 460

Ala Ser Gly Val Pro Ala Arg Phe Ser Gly Ser Gly Ser Gly Thr Asp
465                 470                 475                 480

Tyr Ser Leu Thr Ile Asn Ser Leu Glu Ala Glu Asp Ala Ala Thr Tyr
                485                 490                 495

Tyr Cys Gln Gln Trp Ser Ser Asn Pro Leu Thr Phe Gly Gly Gly Thr
            500                 505                 510

Lys Val Glu Ile Lys His His His His His His
        515                 520

<210> SEQ ID NO 111
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 111

Asp Asp Ile Val Leu Thr Gln Ser Pro Ala Thr Leu Ser Leu Ser Pro
1               5                   10                  15

Gly Glu Arg Ala Thr Leu Ser Cys Arg Ala Ser Gln Ser Val Ser Tyr
            20                  25                  30

Met Asn Trp Tyr Gln Gln Lys Pro Gly Lys Ala Pro Lys Arg Trp Ile
        35                  40                  45

Tyr Asp Thr Ser Lys Val Ala Ser Gly Val Pro Ala Arg Phe Ser Gly
    50                  55                  60

Ser Gly Ser Gly Thr Asp Tyr Ser Leu Thr Ile Asn Ser Leu Glu Ala
65                  70                  75                  80

Glu Asp Ala Ala Thr Tyr Tyr Cys Gln Gln Trp Ser Ser Asn Pro Leu
                85                  90                  95

Thr Phe Gly Gly Gly Thr Lys Val Glu Ile Lys
            100                 105

<210> SEQ ID NO 112
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 112

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115

<210> SEQ ID NO 113
<211> LENGTH: 243
<212> TYPE: PRT
<213> ORGANISM: Artificial Sequence
<220> FEATURE:
<223> OTHER INFORMATION: Synthetic Polypeptide

<400> SEQUENCE: 113

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys

<210> SEQ ID NO 114
<211> LENGTH: 1503
<212> TYPE: DNA
<213> ORGANISM: Artificial Sequence
<220> FEATURE:
<223> OTHER INFORMATION: Synthetic Polynucleotide

<400> SEQUENCE: 114
caggctgtcg tgactcagcc tccttctgct tctggcaccc ctggccagag agtgaccatc        60
tcctgctccg gctcctcctc caacatcggc tccaacaccg tgaactggta tcagcaggtg       120
cccggcaccg cccccaagct gctgatctac tctaacaacc agcggccctc cggcgtgccc       180
gacagattct ctggctctaa gtccggcacc tccgcctccc tggctatctc tggcctgcag       240
tctgaggacg aggccgacta ctactgcgcc gcctgggacg attctctgaa cggctgggtg       300
ttcggcggag gcaccaagct gacagtgctg gaagtagaga gcgtggcgg atctggtggc       360 ggaggatctg gcggaggggg ctctctggaa atggcccaga tgcagctggt gcagtctggc       420
gccgaagtga agagcctgg cgagtccctg cggatctcct gcaagggctc cggctacagc       480
tttaccaact tctggatcag ctgggtgcga cagatgcccg gcaagggcct ggaatggatg       540
ggcagagtgg accccggcta ctcctactcc acctactccc ccagcttcca gggccacgtg       600
accatcagcg ccgacaagtc tacctccacc gcctacctgc agtggaactc cctgaaggcc       660
tccgacaccg ccatgtacta ctgtgcccgg gtgcagtaca gcggctacta cgattggttc       720
gaccccgtgg gccagggcac cctcgtgaca gtgtctagtg gcggggagg atccgacgtg       780 cagctggtgc agagcggagc tgaagtgaag aaacctggcg cctccgtgaa ggtgtcctgc       840
aaagctagcg gctataccct cacccggtac accatgcact gggtgcgcca ggcacctgga       900
cagggactgg aatggatcgg ctacatcaac ccctcccggg gctacaccaa ctacgccgac       960
tctgtgaagg gccggttcac catcaccacc gataagtcca ccagcaccgc ttacatggaa      1020
ctgtcctccc tgagatccga ggacaccgct acctactatt gcgcccggta ctacgacgac      1080
cactactgcc tggactactg gggacaggga accacagtga ccgtgtcctc tggcgagggc      1140
acctctactg gatctggggg aagtggtggt tctggcggcg ctgacgacat cgtgctgacc      1200
cagtctccag ccaccctgtc tctgagccca ggcgagagag ctaccctgtc ctgcagagcc      1260
tcccagtccg tgtcctacat gaattggtat cagcagaagc ctggcaaggc ccctaagcgg      1320
tggatctacg acacctccaa ggtggcctct ggcgtgccag cccggttttc cggatctggc      1380
tctggcaccg actactccct gaccatcaac agcctggaag ccgaggacgc tgccacctat      1440
tactgccagc agtggtcctc caacccctg acctttggag gcggcaccaa ggtggaaatc      1500
aag                                                                   1503

<210> SEQ ID NO 115

<211> LENGTH: 1575
<212> TYPE: DNA
<213> ORGANISM: Artificial Sequence
<220> FEATURE:
<223> OTHER INFORMATION: Synthetic Polynucleotide

<400> SEQUENCE: 115

```
atgggctggt cctgcatcat cctgtttctg gtggctaccg ccaccggcca ggctgtcgtg      60
actcagcctc cttctgcttc tggcacccct ggccagagag tgaccatctc ctgctccggc     120
tcctcctcca acatcggctc caacaccgtg aactggtatc agcaggtgcc cggcaccgcc     180
cccaagctgc tgatctactc taacaaccag cggccctccg gcgtgcccga cagattctct     240
ggctctaagt ccggcacctc cgcctccctg gctatctctg gcctgcagtc tgaggacgag     300
gccgactact actgcgccgc tgggacgat tctctgaacg ctgggtgtt cggcggaggc      360
accaagctga cagtgctggg aagtagaggc ggtggcggat ctggtggcgg aggatctggc     420
ggaggggct ctctggaaat ggcccagatg cagctggtgc agtctggcgc cgaagtgaaa      480
gagcctggcg agtccctgcg gatctcctgc aagggctccg gctacagctt taccaacttc     540
tggatcagct gggtgcgaca gatgcccggc aagggcctgg aatggatggg cagagtggac     600
cccggctact cctactccac ctactccccc agcttccagg ccacgtgac catcagcgcc      660
gacaagtcta cctccaccgc ctacctgcag tggaactccc tgaaggcctc cgacaccgcc     720
atgtactact gtgcccgggt gcagtacagc ggctactacg attggttcga cccctggggc     780
cagggcaccc tcgtgacagt gtctagtggc ggggaggat ccgacgtgca gctggtgcag      840
agcggagctg aagtgaagaa acctggcgcc tccgtgaagg tgtcctgcaa agctagcggc     900
tataccttca cccggtacac catgcactgg gtgcgccagg cacctggaca gggactggaa     960
tggatcggct acatcaaccc ctcccggggc tacaccaact acgccgactc tgtgaagggc    1020
cggttcacca tcaccaccga taagtccacc agcaccgctt acatggaact gtcctccctg    1080
agatccgagg acaccgctac ctactattgc gcccggtact acgacgacca ctactgcctg    1140
gactactggg gacagggaac cacagtgacc gtgtcctctg gcgagggcac ctctactgga    1200
tctgggggaa gtggtggttc tggcggcgct gacgacatcg tgctgaccca gtctccagcc    1260
accctgtctc tgagcccagg cgagagagct accctgtcct gcagagcctc ccagtccgtg    1320
tcctacatga attggtatca gcagaagcct ggcaaggccc ctaagcggtg gatctacgac    1380
acctccaagg tggcctctgg cgtgccagcc cggttttccg gatctggctc tggcaccgac    1440
tactccctga ccatcaacag cctggaagcc gaggacgctg ccacctatta ctgccagcag    1500
tggtcctcca ccccctgac ctttggaggc ggcaccaagg tggaaatcaa gcaccaccat     1560
catcaccact gatag                                                     1575
```

<210> SEQ ID NO 116
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 116

Gly Tyr Ser Phe Thr Asn Phe Trp Ile Ser
1               5                   10

<210> SEQ ID NO 117
<211> LENGTH: 16
<212> TYPE: PRT

<213> ORGANISM: Artificial Sequence
<220> FEATURE:
<223> OTHER INFORMATION: Synthetic Polypeptide

<400> SEQUENCE: 117

Arg Val Asp Pro Gly Tyr Ser Tyr Ser Thr Tyr Ser Pro Ser Phe Gln
1               5                   10                  15

<210> SEQ ID NO 118
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 118

Val Gln Tyr Ser Gly Tyr Tyr Asp Trp Phe Asp Pro
1               5                   10

<210> SEQ ID NO 119
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 119
ggatacagct tcaccaactt ctggatcagc                                    30

<210> SEQ ID NO 120
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 120
agggttgatc ctggctactc ttatagcacc tacagcccgt ccttccaagg c            51

<210> SEQ ID NO 121
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 121
gtacaatata gtggctacta tgactggttc gacccc                             36

<210> SEQ ID NO 122
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 122

Ser Gly Ser Ser Ser Asn Ile Gly Ser Asn Thr Val Asn
1               5                   10

<210> SEQ ID NO 123
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 123

Ser Asn Asn Gln Arg Pro Ser
1               5

<210> SEQ ID NO 124
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 124

Ala Ala Trp Asp Asp Ser Leu Asn Gly Trp Val
1               5                   10

<210> SEQ ID NO 125
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 125
tctggaagca gctccaacat cggaagtaat actgtaaac                                  39

<210> SEQ ID NO 126
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 126
agtaataatc agcggccctc a                                                     21

<210> SEQ ID NO 127
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 127
gcagcatggg atgacagcct gaatggttgg gtg                                        33

<210> SEQ ID NO 128
<211> LENGTH: 451
<212> TYPE: PRT
<213> ORGANISM: Artificial Sequence
<220> FEATURE:
<223> OTHER INFORMATION: Synthetic Polypeptide

<400> SEQUENCE: 128

Gln Met Gln Leu Val Gln Ser Gly Ala Glu Val Lys Glu Pro Gly Glu
1               5                   10                  15

Ser Leu Arg Ile Ser Cys Lys Gly Ser Gly Tyr Ser Phe Thr Asn Phe
            20                  25                  30

Trp Ile Ser Trp Val Arg Gln Met Pro Gly Lys Gly Leu Glu Trp Met
        35                  40                  45

Gly Arg Val Asp Pro Gly Tyr Ser Tyr Ser Thr Tyr Ser Pro Ser Phe
    50                  55                  60

Gln Gly His Val Thr Ile Ser Ala Asp Lys Ser Thr Ser Thr Ala Tyr
65                  70                  75                  80

```
Leu Gln Trp Asn Ser Leu Lys Ala Ser Asp Thr Ala Met Tyr Tyr Cys
                 85                  90                  95

Ala Arg Val Gln Tyr Ser Gly Tyr Tyr Asp Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 129
<211> LENGTH: 1356
<212> TYPE: DNA
<213> ORGANISM: Artificial Sequence
<220> FEATURE:
<223> OTHER INFORMATION: Synthetic Polynucleotide
```

<400> SEQUENCE: 129

```
cagatgcagc tggtgcagtc tggcgccgaa gtgaaagagc ctggcgagtc cctgcggatc      60
tcctgcaagg gctccggcta ctcctttacc aacttctgga tcagctgggt gcgacagatg     120
cccggcaagg gcctggaatg gatgggcaga gtggaccccg gctacagcta ctccacctac     180
tcccccagct ccagggcca cgtgaccatc tccgccgaca gtctacctc caccgcctac       240
ctgcagtgga actccctgaa ggcctccgac accgccatgt actactgcgc cagagtgcag    300
tacagcggct actacgattg gttcgacccc tggggccagg gcaccctcgt gacagtgtcc    360
tctgcttcca ccaagggccc atcggtcttc cccctggcac cctcctccaa gagcacctct     420
gggggcacag cggccctggg ctgcctggtc aaggactact ccccgaacc ggtgacggtg      480
tcgtggaact caggcgccct gaccagcggc gtgcacacct tcccggccgt cctacagtcc     540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
gccagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca agggcagcc ccgagaacca caggtgtaca ccctgccccc atcccgggat    1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaggc tcaccgtgga caagagcagg   1260
tggcagcagg ggaacgtctt ctcatgctcc gtgatgcatg aggctctgca caaccactac   1320
acgcagaaga gcctctccct gtctccgggt aaatga                             1356
```

<210> SEQ ID NO 130
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 130

```
Gln Ala Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly Gln
            100                 105                 110
```

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 131
<211> LENGTH: 651
<212> TYPE: DNA
<213> ORGANISM: Artificial Sequence
<220> FEATURE:
<223> OTHER INFORMATION: Synthetic Polynucleotide

<400> SEQUENCE: 131
caggctgtcg tgactcagcc tccttctgct tctggcaccc ctggccagag agtgaccatc     60
tcctgctccg gctcctcctc aacatcggc tccaacaccg tgaactggta tcagcaggtg    120
cccggcaccg cccccaagct gctgatctac tctaacaacc agcggccctc cggcgtgccc    180
gacagattct ctggctctaa gtccggcacc tccgcctccc tggctatctc tggcctgcag    240
tctgaggacg aggccgacta ctactgcgcc gcctgggacg attctctgaa cggctgggtg    300
ttcggcggag gcaccaagct gacagtgctg ggccagccta aggccaaccc taccgtgacc    360
ctgttccccc catcctccga ggaactgcag gctaacaagg ccaccctcgt gtgcctgatc    420
tccgacttct accctggcgc cgtgaccgtg gcctggaagg ctgatggatc tcctgtgaag    480
gccggcgtgg aaaccaccaa gccctccaag cagtccaaca acaaatacgc cgcctcctcc    540
tacctgtccc tgacccctga gcagtggaag tcccaccggt cctacagctg ccaagtgacc    600
cacgagggct ccaccgtgga aaagaccgtg gctcctaccg agtgctccta g            651

<210> SEQ ID NO 132
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 132

Gln Ala Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

| | | | | | | | | | | | |
|---|---|---|---|---|---|---|---|---|---|---|---|
|Ser|Glu|Asp|Glu|Ala|Asp|Tyr|Tyr|Cys|Ala|Ala|Trp|Asp|Asp|Ser|Leu|
| | | | |85| | | |90| | | |95| | | |

Asn Gly Trp Val Phe Gly Gly Thr Lys Leu Thr Val Leu Gly Ser
            100                 105                 110

Arg Gly Gly Gly Ser Gly Gly Gly Ser Gly Gly Gly Ser
        115                 120                 125

Leu Glu Met Ala Gln Met Gln Leu Val Gln Ser Gly Ala Glu Val Lys
130                 135                 140

Glu Pro Gly Glu Ser Leu Arg Ile Ser Cys Lys Gly Ser Gly Tyr Ser
145                 150                 155                 160

Phe Thr Asn Phe Trp Ile Ser Trp Val Arg Gln Met Pro Gly Lys Gly
                165                 170                 175

Leu Glu Trp Met Gly Arg Val Asp Pro Gly Tyr Ser Tyr Ser Thr Tyr
            180                 185                 190

Ser Pro Ser Phe Gln Gly His Val Thr Ile Ser Ala Asp Lys Ser Thr
        195                 200                 205

Ser Thr Ala Tyr Leu Gln Trp Asn Ser Leu Lys Ala Ser Asp Thr Ala
    210                 215                 220

Met Tyr Tyr Cys Ala Arg Val Gln Tyr Ser Gly Tyr Tyr Asp Trp Phe
225                 230                 235                 240

Asp Pro Trp Gly Gln Gly Thr Leu Val Thr Val Ser Ser
                245                 250

<210> SEQ ID NO 133
<211> LENGTH: 759
<212> TYPE: DNA
<213> ORGANISM: Artificial Sequence
<220> FEATURE:
<223> OTHER INFORMATION: Synthetic Polynucleotide

<400> SEQUENCE: 133

```
caggctgtgg tgactcagcc accctcagcg tctgggaccc ccgggcagag ggtcaccatc    60
tcttgttctg gaagcagctc caacatcgga agtaatactg taaactggta ccagcaggtc   120
ccaggaacgg ccccccaaact cctcatctat agtaataatc agcggccctc aggggtccct   180
gaccgattct ctggctccaa gtctggcacc tcagcctccc tggccatcag tgggctccag   240
tctgaggatg aggctgatta ttactgtgca gcatgggatg acagcctgaa tggttgggtg   300
ttcggcggag gaccaagct gaccgtccta ggttctagag gtggtggtgg tagcggcggc   360
ggcggctctg gtggtggtgg atccctcgag atgcccaga tgcagctggt gcagtccgga   420
gcagaggtga agagcccggg ggagtctctg aggatctcct gtaagggttc tggatacagc   480
ttcaccaact ctggatcag ctgggtgcgc cagatgcccg ggaaaggcct ggagtggatg   540
gggagggttg atcctggcta ctcttatagc acctacagcc cgtccttcca aggccacgtc   600
accatctcag ctgacaagtc taccagcact gcctacctgc agtggaacag cctgaaggcc   660
tcggacaccg ccatgtatta ctgtgcgaga gtacaatata gtggctacta tgactggttc   720
gacccctggg gccagggaac cctggtcacc gtctcctca                          759
```

<210> SEQ ID NO 134
<211> LENGTH: 449
<212> TYPE: PRT
<213> ORGANISM: Artificial Sequence
<220> FEATURE:
<223> OTHER INFORMATION: Synthetic Polypeptide

<400> SEQUENCE: 134

-continued

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Phe
            50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
            85                  90                  95

Ala Arg Tyr Tyr Asp Asp His Tyr Cys Leu Asp Tyr Trp Gly Gln Gly
            100                 105                 110

Thr Pro Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Leu Leu Tyr Ser Lys Leu Thr Val Asp Lys
            405                 410                 415

Ser Arg Trp Gln Gln Gly Asn Val Phe Ser Cys Ser Val Met His Glu 420                 425                 430
Ala Leu His Asn His Tyr Thr Gln Lys Ser Leu Ser Leu Ser Pro Gly
        435                 440                 445

Lys

<210> SEQ ID NO 135
<211> LENGTH: 1350
<212> TYPE: DNA
<213> ORGANISM: Artificial Sequence
<220> FEATURE:
<223> OTHER INFORMATION: Synthetic Polynucleotide

<400> SEQUENCE: 135

| | |
|---|---|
| caggtgcagc tggtgcagtc cggcggcggc gtggtgcagc ccggccggtc cctgcggctg | 60 |
| tcctgcaagg cctccggcta caccttcacc cggtacacca tgcactgggt gcggcaggcc | 120 |
| cccggcaagg gcctggagtg gatcggctac atcaaccccc ccggggcta caccaactac | 180 |
| aaccagaagt tcaaggaccg gttcaccatc tcccgggaca actccaagaa caccgccttc | 240 |
| ctgcagatgg actccctgcg gcccgaggac accggcgtgt acttctgcgc ccggtactac | 300 |
| gacgaccact actgcctgga ctactggggc cagggcaccc ccgtgaccgt gtcctccgcc | 360 |
| tccaccaagg gcccatcggt cttccccctg gcaccctcct ccaagagcac ctctggggc | 420 |
| acagcggccc tgggctgcct ggtcaaggac tacttccccg aaccggtgac ggtgtcgtgg | 480 |
| aactcaggcg ccctgaccag cggcgtgcac accttcccgg ccgtcctaca gtcctcagga | 540 |
| ctctactccc tcagcagcgt ggtgaccgtg ccctccagca gcttgggcac ccagacctac | 600 |
| atctgcaacg tgaatcacaa gcccagcaac accaaggtgg acaagagagt tgagcccaaa | 660 |
| tcttgtgaca aaactcacac atgcccaccg tgcccagcac ctgaactcct gggggaccg | 720 |
| tcagtcttcc tcttcccccc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacgccagc | 900 |
| acgtaccgtg tggtcagcgt cctcaccgtc ctgcaccagg actggctgaa tggcaaggag | 960 |
| tacaagtgca aggtctccaa caaagccctc ccagccccca tcgagaaaac catctccaaa | 1020 |
| gccaaagggc agccccgaga accacaggtg tacaccctgc ccccatcccg ggatgagctg | 1080 |
| accaagaacc aggtcagcct gacctgcctg gtcaaaggct tctatcccag cgacatcgcc | 1140 |
| gtggagtggg agagcaatgg gcagccggag aacaactaca agaccacgcc tcccgtgctg | 1200 |
| gactccgacg gctccttcct cctctacagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gggtaaatga | 1350 |

<210> SEQ ID NO 136
<211> LENGTH: 213
<212> TYPE: PRT
<213> ORGANISM: Artificial Sequence
<220> FEATURE:
<223> OTHER INFORMATION: Synthetic Polypeptide

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
            35                  40                  45

Asp Thr Ser Lys Leu Ala Ser Gly Val Pro Ser Arg Phe Ser Gly Ser
 50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 137
<211> LENGTH: 642
<212> TYPE: DNA
<213> ORGANISM: Artificial Sequence
<220> FEATURE:
<223> OTHER INFORMATION: Synthetic Polynucleotide

<400> SEQUENCE: 137
gacatccaga tgacccagtc ccctcctcc ctgtccgcct ccgtgggcga ccgggtgacc      60
atcacctgct ccgcctcctc ctccgtgtcc tacatgaact ggtaccagca gaccccccggc    120
aaggccccca gcggtggat ctacgacacc tccaagctgg cctccggcgt gccctcccgg     180
ttctccggct ccggctccgg caccgactac accttcacca tctcctccct gcagcccgag    240
gacatcgcca cctactactg ccagcagtgg tcctccaacc ccttcacctt cggccagggc    300
accaagctgc agatcacccg gaccgtggcc gcccctccg tgttcatctt ccccccctcc     360
gacgagcagc tgaagtccgg caccgcctcc gtggtgtgcc tgctgaacaa cttctacccc    420
cgggaggcca aggtgcagtg gaaggtggac aacgccctgc agtccggcaa ctcccaggag    480
tccgtgaccg agcaggactc caaggactcc acctactccc tgtcctccac cctgaccctg    540
tccaaggccg actacgagaa gcacaaggtg tacgcctgcg aggtgaccca ccagggcctg    600
tcctcccccg tgaccaagtc cttcaaccgg ggcgagtgct ag                       642

<210> SEQ ID NO 138
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 138

Lys Ile Phe Gly Ser Leu Ala Phe Leu

```
<210> SEQ ID NO 139
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 139

Leu Phe Glu Val Arg Val Cys Ala Cys
1               5

<210> SEQ ID NO 140
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 140

Ala Leu Tyr Val Asp Ser Leu Phe Phe Leu
1               5                   10

<210> SEQ ID NO 141
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 141

Asn Leu Thr His Val Leu Tyr Pro Val
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 142

Gln Leu Gln Asn Pro Ser Tyr Asp Lys
1               5
```